(12) United States Patent
Holers et al.

(10) Patent No.: US 10,239,937 B2
(45) Date of Patent: Mar. 26, 2019

(54) TREATMENT OF PAROXYSMAL NOCTURNAL HEMOGLOBINURIA, HEMOLYTIC ANEMIAS AND DISEASE STATES INVOLVING INTRAVASCULAR AND EXTRAVASCULAR HEMOLYSIS

(75) Inventors: V. Michael Holers, Denver, CO (US); Antonio M. Risitano, Naples (IT)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 13/505,150

(22) PCT Filed: Nov. 5, 2010

(86) PCT No.: PCT/US2010/055745
§ 371 (c)(1),
(2), (4) Date: Oct. 15, 2012

(87) PCT Pub. No.: WO2011/057158
PCT Pub. Date: May 12, 2011

(65) Prior Publication Data
US 2013/0029912 A1    Jan. 31, 2013

Related U.S. Application Data

(60) Provisional application No. 61/280,567, filed on Nov. 5, 2009.

(51) Int. Cl.
| | | |
|---|---|---|
| *C07K 16/18* | (2006.01) |
| *C07K 14/47* | (2006.01) |
| *C07K 14/705* | (2006.01) |
| *A61K 38/17* | (2006.01) |

(52) U.S. Cl.
CPC ............ *C07K 16/18* (2013.01); *A61K 38/178* (2013.01); *A61K 38/1709* (2013.01); *C07K 14/47* (2013.01); *C07K 14/70596* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,883,784 A | 11/1989 | Kaneko |
| 5,212,071 A | 5/1993 | Fearon et al. |
| 5,260,203 A | 11/1993 | Ladner et al. |
| 5,310,729 A | 5/1994 | Lernhardt |
| 5,328,470 A | 7/1994 | Nabel et al. |
| 5,331,090 A | 7/1994 | Lernhardt |
| 5,472,939 A | 12/1995 | Fearon et al. |
| 5,679,345 A | 10/1997 | Sanfilippo et al. |
| 5,679,546 A | 10/1997 | Ko et al. |
| 5,851,528 A | 12/1998 | Ko et al. |
| 5,981,481 A | 11/1999 | Fearon et al. |
| 6,140,472 A | 10/2000 | Rosengard et al. |
| 6,214,966 B1 | 4/2001 | Harris |
| 6,224,866 B1 | 5/2001 | Barbera-Guillem |
| 6,248,365 B1 | 6/2001 | Romisch et al. |
| 6,291,239 B1 | 9/2001 | Prodinger et al. |
| 6,355,245 B1 | 3/2002 | Evans et al. |
| 6,368,596 B1 | 4/2002 | Ghetie et al. |
| 6,432,679 B1 | 8/2002 | Mond et al. |
| 6,458,360 B1 | 10/2002 | Fearon et al. |
| 6,503,947 B1 | 1/2003 | Lipton et al. |
| 6,521,450 B1 | 2/2003 | Atkinson et al. |
| 6,572,856 B1 | 6/2003 | Taylor et al. |
| 6,820,011 B2 | 11/2004 | Chen et al. |
| 6,897,290 B1 | 5/2005 | Atkinson et al. |
| 6,962,903 B2 | 11/2005 | Allison |
| 7,407,475 B2 | 8/2008 | Allison |
| 7,423,128 B2 | 9/2008 | Gazit-Bornstein et al. |
| 7,439,331 B2 | 10/2008 | Fung et al. |
| 7,576,182 B1 | 8/2009 | Goddard et al. |
| 7,635,676 B2 | 12/2009 | Allison |
| 7,635,678 B2 | 12/2009 | Allison |
| 7,635,679 B2 | 12/2009 | Fumero et al. |
| 7,635,680 B2 | 12/2009 | Allison |
| 7,645,739 B2 | 1/2010 | Allison |
| 7,759,304 B2 * | 7/2010 | Gilkeson et al. ............. 514/1.1 |
| 7,964,705 B2 | 6/2011 | Emlen et al. |
| 7,999,082 B2 | 8/2011 | Holers et al. |
| 8,007,804 B2 | 8/2011 | Tomlinson et al. |
| 2002/0103346 A1 | 8/2002 | Vogel et al. |
| 2003/0077273 A1 | 4/2003 | Linnik et al. |
| 2003/0165509 A1 | 9/2003 | Ghetie et al. |

(Continued)

FOREIGN PATENT DOCUMENTS

| | | |
|---|---|---|
| EP | 0358130 A2 | 3/1990 |
| EP | 0402226 A1 | 12/1990 |

(Continued)

OTHER PUBLICATIONS

Sarnaik et al, Periodic transfusions for sickle cell anemia and CNS infarction, Am J Dis Child, Dec. 1979;133(12):1254-7.*
Fishelson et al, Regulation of the Alternative Pathway of Complement by pH, The Journal of Immunology, vol. 138, pp. 3392-3395, 1987.*
Ricklin et al, Complement-targeted therapeutics, Nature Biotechnology, vol. 25 No. 11, Nov. 2007.*
Mache et al, Complement Inhibitor Eculizumab in Atypical Hemolytic Uremic Syndrome, Clin J Am Soc Nephrol 4: 1312-1316, 2009.*
Hillmen et al, Effect of Eculizumab on Hemolysis and Transfusion Requirements in Patients with Paroxysmal Nocturnal Hemoglobinuria, N Engl J Med 2004;350:552-9.*
Razzaq, Hemolytic Uremic Syndrome: An Emerging Health Risk, American Family Physician, vol. 74, No. 6, Sep. 15, 2006.*

(Continued)

*Primary Examiner* — Sergio Coffa
(74) *Attorney, Agent, or Firm* — Clark & Elbing LLP

(57) ABSTRACT

Methods for treating subjects having complement-mediated hemolytic disorders, such as paroxysmal nocturnal hemoglobinuria (PNH) and other hemolytic anemias, the method comprising administering an effective amount of a composition that inhibits the activity of the complement alternative pathway.

33 Claims, 33 Drawing Sheets
Specification includes a Sequence Listing.

(56) References Cited

U.S. PATENT DOCUMENTS

| | | |
|---|---|---|
| 2003/0180292 A1 | 9/2003 | Hanna et al. |
| 2004/0005538 A1 | 1/2004 | Chen et al. |
| 2004/0191252 A1 | 9/2004 | Taylor et al. |
| 2004/0219156 A1 | 11/2004 | Goldenberg et al. |
| 2005/0002128 A1 | 1/2005 | Ito et al. |
| 2005/0032128 A1 | 2/2005 | Halperin |
| 2005/0232920 A1 | 10/2005 | Fung et al. |
| 2005/0260198 A1 | 11/2005 | Holers et al. |
| 2005/0265995 A1 | 12/2005 | Tomlinson et al. |
| 2006/0002944 A1 | 1/2006 | Ashkenazi et al. |
| 2006/0014681 A1 | 1/2006 | Chen et al. |
| 2006/0178308 A1 | 8/2006 | Schwaeble et al. |
| 2006/0263819 A1 | 11/2006 | Hageman et al. |
| 2006/0276388 A1 | 12/2006 | Christa et al. |
| 2006/0292141 A1 | 12/2006 | Holers et al. |
| 2007/0003544 A1 | 1/2007 | Hanna |
| 2007/0020647 A1 | 1/2007 | Hageman et al. |
| 2007/0134260 A1 | 6/2007 | Feger et al. |
| 2007/0172483 A1 | 7/2007 | Schwaeble et al. |
| 2007/0224197 A1 | 9/2007 | Chen et al. |
| 2008/0029911 A1 | 2/2008 | Jeon et al. |
| 2008/0118506 A1 | 5/2008 | An et al. |
| 2008/0221011 A1* | 9/2008 | Gilkeson et al. ............ 514/2 |
| 2008/0267980 A1 | 10/2008 | Tomlinson et al. |
| 2008/0299114 A1 | 12/2008 | Emlen et al. |
| 2009/0081211 A1 | 3/2009 | Campagne |
| 2009/0087907 A1 | 4/2009 | Pebay et al. |
| 2009/0175875 A1 | 7/2009 | Etemad-Gilbertson et al. |
| 2009/0304706 A1 | 12/2009 | Lu et al. |
| 2011/0014614 A1 | 1/2011 | Liew |
| 2011/0015127 A1 | 1/2011 | Gilkeson et al. |
| 2011/0286938 A1 | 11/2011 | Thurman et al. |
| 2012/0014952 A1 | 1/2012 | Tomlinson et al. |
| 2012/0015871 A1 | 1/2012 | Tomlinson et al. |
| 2012/0015872 A1 | 1/2012 | Tomlinson et al. |
| 2012/0135430 A1 | 5/2012 | Zhang et al. |
| 2012/0171206 A1 | 7/2012 | Tomlinson et al. |
| 2013/0029912 A1 | 1/2013 | Holers et al. |
| 2013/0129728 A1 | 5/2013 | Holers et al. |
| 2013/0190477 A1 | 7/2013 | Kovacs et al. |

FOREIGN PATENT DOCUMENTS

| | | |
|---|---|---|
| EP | 0402266 A2 | 12/1990 |
| WO | WO-91/16437 A1 | 10/1991 |
| WO | WO-96/12742 A1 | 5/1996 |
| WO | WO-98/07835 A2 | 2/1998 |
| WO | WO-99/44625 A1 | 9/1999 |
| WO | WO-00/34317 A2 | 6/2000 |
| WO | WO-00/34317 A3 | 8/2000 |
| WO | WO-00/67796 A1 | 11/2000 |
| WO | WO-02/068579 A2 | 9/2002 |
| WO | WO-2004/045520 A2 | 6/2004 |
| WO | WO-2004/103288 A2 | 12/2004 |
| WO | WO-2005/014618 A2 | 2/2005 |
| WO | WO-2005/044998 A2 | 5/2005 |
| WO | WO-2005/072479 A2 | 8/2005 |
| WO | WO-2005/077417 A1 | 8/2005 |
| WO | WO-2006/030220 A1 | 3/2006 |
| WO | WO-2006/062716 A2 | 6/2006 |
| WO | WO-2006/083533 A2 | 8/2006 |
| WO | WO-2006/088950 A2 | 8/2006 |
| WO | WO-2006/128006 A1 | 11/2006 |
| WO | WO-2007/029008 A2 | 3/2007 |
| WO | WO-2007/035857 A2 | 3/2007 |
| WO | WO-2007/056227 A2 | 5/2007 |
| WO | WO-2007/112403 A2 | 10/2007 |
| WO | WO-2007/129895 A2 | 11/2007 |
| WO | WO-2007/149567 A2 | 12/2007 |
| WO | WO-2008/154251 A2 | 12/2008 |
| WO | WO-2009/029669 A1 | 3/2009 |
| WO | WO-2009/056631 A2 | 5/2009 |
| WO | WO-2009/110918 A1 | 9/2009 |
| WO | WO-2010/015608 A1 | 2/2010 |
| WO | WO-2010/091183 A2 | 8/2010 |
| WO | WO-2010/136311 A2 | 12/2010 |
| WO | WO-2011/057158 A1 | 5/2011 |
| WO | WO-2011/143637 A1 | 11/2011 |
| WO | WO-2011/163412 A1 | 12/2011 |
| WO | WO-2013/177035 A2 | 11/2013 |

OTHER PUBLICATIONS

ClinicalTrials NCT00001964, Dec. 1999.*
Mastellos et al. (Expert Rev Hematol. Oct. 2014 ; 7(5): 583-598).*
Hillmen (Hematology Am Soc Hematol Educ Program. 2008:116-23) (Year: 2008).*
Dhaliwal et al. (American Family Physician, Jun. 1, 2004 / vol. 69, No. 11, pp. 2599-2606) (Year: 2004).*
Blank et al., "Hemoglobin interference from in vivo hemolysis," Clin Chem. 31(9):1566-9 (1985).
Brodsky, "How I treat paroxysmal nocturnal hemoglobinuria," Blood. 113(26):6522-7 (2009).
Holers et al., "The spectrum of complement alternative pathway-mediated diseases," Immunol Rev. 223:300-316 (2008).
Huang et al., "A novel targeted inhibitor of the alternative pathway of complement and its therapeutic application in ischemia/reperfusion injury," J Immunol. 181(11) (2008) (19 pages).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Paroxysmal nocturnal hemoglobinuria: pathophysiology, natural history and treatment options in the era of biological agents," Biologics. 2(2):205-222 (2008).
Risitano et al., "The complement receptor 2/factor H fusion protein TT30 protects paroxysmal nocturnal hemoglobinuria erythroctyes from complement-mediated hemolysis and C3 fragment," Blood. 119(26):6307-6316 (2012).
Rohrer et al., "A targeted inhibitor of the alternative complement pathway reduces angiogenesis in a mouse model of age-related macular degeneration," Invest Ophthalmol Vis Sci. 50(7):3056-3064 (2009).
Yang et al., "An engineered complement receptor 1 composed of two functional domains can protect against immune-mediated hemolysis," Protein Expr Purif. 66(1):28-34 (2009).
Extended European Search Report for European Application No. 10829204.6, dated Mar. 5, 2013 (9 pages).
International Search Report for International Application No. PCT/US2010/055745, dated Feb. 4, 2011 (3 pages).
"Monoclonal antibody to human C3(C3d), Catalog No. A207," Quidel Corporation Product Catalog, <http://www.quidel.com/products/product_detail.php?prod=73&group=2>, retrieved on Apr. 25, 2013 (2 pages).
"Monoclonal antibody to human C3d (neo), Catalog No. A250," Quidel Corporation Product Catalog, <http://www.quidel.com/products/product_detail.php?prod=160&group=2>, retrieved on Dec. 26, 2013 (2 pages).
Abrahmsén et al., "Engineering subtilisin and its substrates for efficient ligation of peptide bonds in aqueous solution," Biochemistry. 30:4151-4159 (1991).
Aguado et al., "Monoclonal antibodies against complement 3 neoantigens for detection of immune complexes and complement activation. Relationship between immune complex levels, state of C3, and numbers of receptors for C3b," J Clin Invest. 76:1418-26 (1985).
Ahearn et al., "Disruption of the Cr2 locus results in a reduction in B-1a cells and in an imparied B cell response to T-dependent antigen," Immunity. 4(3):251-262 (1996).
Ahearn et al., "Epstein-Barr virus (EBV) infection of murine L cells expressing recombinant human EBV/C3d receptor," Proc Natl Acad Sci USA. 85:9307-11 (1988).
Ahearn et al., "Structure and function of the complement receptors, CR1 (CD35) and CR2 (CD21)," Adv Immunol. 46:183-219 (1989).
Amsterdam et al., "Limitation of reperfusion injury by a monoclonal antibody to C5a during myocardial infarction in pigs," Am J Physiol. 268(1):H448-57 (1995).

(56) References Cited

OTHER PUBLICATIONS

Andrews et al., "Spontaneous murine Lupus-like syndromes. Clinical and immunopathological manifestations in several strains," J Exp Med. 148:1198-215 (1978).
Arumugam et al., "Complement mediators in ischemia-reperfusion injury," Clin Chim Acta. 374:33-45 (2006).
Arumugam et al., "Protective effect of a human C5a receptor antagonist against hepatic ischaemia-reperfusion injury to rats," J Hepatol. 40:934-41 (2004).
Aslam et al., "Folded-back solution structure of monomeric factor H of human complement by synchrotron X-ray and neutron scattering, analytical ultracentrifugation and constrained molecular modelling," J Mol Biol. 309(5):1117-1138 (2001).
Asokan et al., "Characterization of human complement receptor type 2 (CR2/CD21) as a receptor for IFN-alpha: a potential role in systemic lupus erythematosus," J Immunol. 177:383-94 (2006).
Atkinson et al., "Complement-dependent P-selectin expression and injury following ischemic stroke," J Immunol. 177:7266-74 (2006).
Atkinson et al., "Targeted complement inhibition by C3d recognition ameliorates tissue injury without apparent increase in susceptibility to infection," J Clin Invest. 115(9):2444-53 (2005).
Atkinson et al., "Targeted complement inhibitors protect against posttransplant cardiac ischemia and reperfusion injury and reveal an important role for the alternative pathway of complement activation," J Immunol. 185:7007-13 (2010).
Atkinson et al., "Targeted inhibition of the alternative complement pathway delays the onset of antibody-mediated rejection in a mouse heterotopic heart transplant model," Mol Immunol. 44:3944, Abstract No. P24 (2007).
Aubry et al., "CD21 is a ligand for CD23 and regulates IgE production," Nature. 358(6386):505-507 (1992).
Aubry et al., "CD23 interacts with a new functional extracytoplasmic domain involving N-linked oligosaccharides on CD21," J Immunol. 152:5806-13 (1994).
Author manuscript of Clark et al., "Evidence for non-traditional activation of complement factor C3 during murine liver regeneration," available in PMC Jun. 1, 2009, published in final edited form as: Mol Immunol. 45(11):3125-32 (2008) (15 pages).
Author manuscript of Habermann et al., "Increased serum levels of complement C3a anaphylatoxin indicate the presence of colorectal tumors," available in PMC Sep. 8, 2008, published in final edited form as: Gastroenterol. 131(4):1020-9 (2006) (17 pages).
Baechler et al., "Interferon-inducible gene expression signature in peripheral blood cells of patients with severe lupus," Proc Natl Acad Sci USA. 100:2610-5 (2003).
Bagshawe et al., "A cytotoxic agent can be generated selectively at cancer sites," Br J Cancer. 58:700-703 (1988).
Bagshawe, "Towards generating cytotoxic agents at cancer sites," Br J Cancer. 60:275-281(1989).
Baldo et al., "The adipsin-acylation stimulating protein system and regulation of intracellular triglyceride synthesis," J Clin Invest. 92:1543-47 (1993).
Banda et al., "Targeted inhibition of the complement alternative pathway with complement receptor 2 and factor H attenuates collagen antibody-induced arthritis in mice," J Immunol. 183:5928-37 (2009).
Baranyi et al., "Cell-surface bound complement regulatory activity is necessary for the in vivo survival of KDH-8 rat hepatoma," Immunology. 82(4):522-8 (1994).
Barlow et al., "Solution structure of a pair of complement modules by nuclear magnetic resonance," J Mol Biol. 232:268-284 (1993).
Battelli et al., "T lymphocyte killing by a xanthine-oxidase-containing immunotoxin," Cancer Immunol Immunother. 35:421-425 (1992).
Benvenuti et al., "Crystallization of soluble proteins in vapor diffusion for X-ray crystallography," Nat Protoc. 2(7):1633-1651 (2007).

Bergelson et al., "Decay-accelerating factor (CD55), a glycosylphosphatidylinositol-anchored complement regulatory protein, is a receptor for several echoviruses," Proc Nat Acad Sci USA. 91(13):6245-9 (1994).
Bohnsack et al., "CR2 ligands modulate human B cell activation," J Immunol. 141:2569-76 (1988).
Boross et al., "Boosting antibody therapy with complement," Blood. 119(25):5945-5947 (2012).
Brauer et al., "Functional activity of anti-C6 antibodies elicited in C6-deficient rats reconstituted by liver allografts. Ability to inhibit hyperacute rejection of discordant cardiac xenografts," Transplantation 61(4):588-94 (1996).
Brown et al., "Molecular and cellular mechanisms of receptor-mediated endocytosis," DNA Cell Biol. 10:399-409 (1991).
Bykov, "Complement system and alcoholic liver disease," University of Helsinki 1-69 (2008).
Camargo et al., "Interleukin-6 protects liver against warm ischemia/reperfusion injury and promotes hepatocyte proliferation in the rodent," Hepatology. 26:1513-20 (1997).
Cambier, "Signalling processes in haematopoietic cells: positive and negative signal co-operativity in the immune system: the BCR, Fc gamma RIIB, CR2 paradigm," Biochem Soc Trans. 25(2):441-445 (1997).
Caragine et al., "A tumor-expressed inhibitor of the early but not late complement lytic pathway enhances tumor growth in a rat model of human breast cancer," Cancer Res. 62(4):1110-5 (2002).
Cardarelli et al., "A nonfucosylated human antibody to CD19 with potent B-cell depletive activity for therapy of B-cell malignancies," Cancer Immunol Immunother. 59(2):257-65 (2010).
Carel et al., "Structural requirements for C3d,g/Epstein-Barr virus receptor (CR2/CD21) ligand binding, internalization, and viral infection," J Biol Chem. 265(21):12293-9 (1990).
Carroll, "The role of complement and complement receptors in induction and regulation of immunity," Annu Rev Immunol. 16:545-568 (1998).
Carroll, The role of complement in B cell activation and tolerance. *Advances in Immunology.* Dixon,74:61-88 (2000).
Carter et al., "CD19: lowering the threshold for antigen receptor stimulation of B lymphocytes," Science. 256:105-7 (1992).
Carter et al., "Polymeric C3dg primes human B lymphocytes for proliferation induced by anti-IgM," J Immunol. 143(6):1755-60 (1989).
Carter et al., "Synergistic interaction between complement receptor type 2 and membrane IgM on B lymphocytes," J Immunol. 141:457-63 (1988).
Casasnovas et al., "Crystal structure of two CD46 domains reveals an extended measles virus-binding surface," EMBO J. 18(11):2911-2922 (1999).
Chavez-Cartaya et al., "Regulation of the complement cascade by soluble complement receptor type 1. Protective effect in experimental liver ischemia and reperfusion," Transplantation. 59:1047-52 (1995).
Chen et al., "CD59 expressed on a tumor cell surface modulates decay-accelerating factor expression and enhances tumor growth in a rat model of human neuroblastoma," Cancer Res. 60(11):3013-8 (2000).
Chen et al., "Gene therapy for brain tumors: regression of experimental gliomas by adenovirus-mediated gene transfer in vivo," Proc Natl Acad Sci USA. 91:3054-3057 (1994).
Christiansen et al., "A functional analysis of recombinant soluble CD46 in vivo and a comparison with recombinant soluble forms of CD55 and CD35 in vitro," Eur J Immunol. 26(3):578-85 (1996).
Clavien et al., "Strategies for safer liver surgery and partial liver transplantation," N Engl J Med. 356:1545-59 (2007).
Clemenza et al., "Structure-guided identification of C3d residues essential for its binding to complement receptor 2 (CD21)," J Immunol. 165:3839-3848 (2000).
Colvin, "Antibody-mediated renal allograft rejection: diagnosis and pathogenesis," J Am Soc Nephrol. 18(4):1046-56 (2007).
Cooper et al., "Immunobiology of CR2, the B lymphocyte receptor for Epstein-Barr virus and the C3d complement fragment," Ann Rev Immunol. 6:85-113 (1988).

(56) References Cited

OTHER PUBLICATIONS

Crumm et al., "Adenine necleotide changes in the remnant liver: an early signal for regeneration after partial hepatectomy," Hepatology. 48:898-908 (2008).
Cudney, "Protein crystallization and dumb luck," The Rigaku Journal. 16(1):1-7 (1999).
Dahm et al., "Small-for-size syndrome after partial liver transplantation: definition, mechanisms of disease and clinical implications," Am J Transplant. 5:2605-10 (2005).
Davies et al., "CD59, a Ly-6-Like protein expressed in human lymphoid cells, regulates the action of the complement membrane attack complex on homologous cells," J Exp Med. 170(3):637-54 (1989).
De Córdoba et al., "The human complement factor H: functional roles, genetic variations and disease associations," Molec Immunol. 41:355-67 (2004).
Delaglio et al., "NMRPipe: a multidimensional spectral processing system based on UNIX pipes," J Biomol NMR. 6:277-93 (1995).
Delcayre et al., "Epstein Barr virus/complement C3d receptor is an interferon alpha receptor," EMBO J. 10:919-26 (1991).
Delcayre et al., "Inhibition of Epstein-Barr virus-mediated capping of CD21/CR2 by alpha interferon (IFN-alpha): immediate antiviral activity of IFN-alpha during the early phase of infection," J Virol. 67:2918-21 (1993).
Dempsey et al., "C3d of complement as a molecular adjuvant: bridging innate and acquired immunity," Science. 271:348-350 (1996).
Dev et al., "Electrochemotherapy—A novel method of cancer treatment," Cancer Treat Rev. 20:105-115 (1994).
Diefenbach et al., "Mutation of residues in the C3dg region of human complement component C3 corresponding to a proposed binding site for complement receptor type 2 (CR2, CD21) does not abolish binding of iC3b or C3dg to CR2," J Immunol. 154(5):2303-2320 (1995).
Dierich et al., "Structural and functional relationships among receptors and regulators of the complement system," Mol Immunol. 25(11):1043-1051 (1988).
Dilillo et al., "Selective and efficient inhibition of the alternative pathway of complement by a mAb that recognizes C3b/iC3b," Mol Immunol. 43:1010-9 (2006).
Dobbie et al., "Epitope specificities and quantitative and serologic aspects of monoclonal complement (C3c and C3d) antibodies," Transfusion. 27(6):453-459 (1987).
Dominguez et al., "HADDOCK: a protein-protein docking approach based on biochemical or biophysical information," J Am Chem Soc. 125:1731-7 (2003).
Drenth, Crystalling a Protein. *Principles of Protein X-Ray Crystallography.* Springer-Verlag, 1-21 (1999).
Duits et al., "Selective enhancement of Leu-Cam expression by Interleukin 6 during differentiation of human promonocytic U937 cells," Scand J Immunol. 33(2):151-9 (1991).
Duranski et al., "Cytoprotective effects of nitrite during in vivo ischemia-reperfusion of the heart and liver," J Clin Invest. 115(5):1232-40 (2005).
Dutkowski et al., "Novel short-term hypothermic oxygenated perfusion (HOPE) system prevents injury in rat liver graft from non-heart beating donor," Ann Surg. 244(6):968-76, discussion 976-7 (2006).
Dörig et al., "The human CD46 molecule is a receptor for measles virus (Edmonston strain)," Cell. 75(2):295-305 (1993).
EBI Accession No. CQ729676, <http://ibis/IBIS/exam/dbfetch.jsp?id=EM_PAT:CQ729676>retrieved on Jan. 3, 2011(1 page).
EBI Accession No. CQ729676. Retrieved on Jan. 3, 2011 (1 page).
Edberg et al., "Quantitative analyses of the binding of soluble complement-fixing antibody/dsDNA immune complexes to CR1 on human red blood cells," J Immunol. 139:3739-47 (1987).
Edwards et al., "Complement factor H polymorphism and age-related macular degeneration," Science. 308:421-4 (2005).
Elvington et al., "A targeted complement-dependent strategy to improve the outcome of mAb therapy, and characterization in a murine model of metastatic cancer," Blood. 119(25):6043-6051 (2012).
Extended European Search Report and Written Opinion for European Application No. 11781394.9, dated Sep. 19, 2013 (11 pages).
Fabrikant, "The kinetics of cellular proliferation in regenerating liver," J Cell Biol. 36(3):551-65 (1968).
Fausto, "Involvement of the innate immune system in liver regeneration and injury," J Hepatol. 45:347-9 (2006).
Fearon et al., "The CD19/CR2/TAPA-1 complex of B lymphocytes: Linking natural to acquired immunity," Annu Rev Immunol. 13:127-149 (1995).
Fearon, "The complement system and adaptive immunity," Semin Immunol. 10(5):355-361 (1998).
Ferreira et al., "Factor H-mediated cell surface protection from complement is critical for the survival of PNH erythrocytes," Blood. 110(6):2190-2 (2007).
Fingeroth et al., "Characterization of a T-lymphocyte Epstein-Barr virus/C3d receptor (CD21)," J Virol. 62:1442-7 (1988).
Fingeroth et al., "Epstein-Barr virus receptor of human B lymphocytes is the C3d receptor CR2," Proc Natl Acad Sci USA. 81(14):4510-4514 (1984).
Fingeroth et al., "Identification of murine complement receptor type 2," Proc Natl Acad Sci USA. 86(1):242-246 (1989).
Fiorini et al., "Development of an unbiased method for the estimation of liver steatosis," Clin Transplant. 18:700-6 (2004).
Fondevila et al., "The membrane attack complex (C5b-9) in liver cold ischemia and reperfusion injury," Liver Transpl. 14:1133-41 (2008).
Franco-Gou et al., "Protection of reduced-size liver for transplantation," Am J Transplant. 4(9):1408-20 (2004).
Fritzinger et al., "Functional characterization of human C3/cobra venom factor hybrid proteins for therapeutic complement depletion," Develop Comp Immunol. 33(1):105-16 (2009).
Fritzinger et al., "Molecular cloning and derived primary structure of cobra venom factor," Proc Natl Acad Sci USA. 91:12775-12779 (1994); correction 92: 7065 (1995).
Frémeaux-Bacchi et al., "Soluble CD21 induces activation and differentiation of human monocytes through binding to membrane CD23," Eur J Immunol. 28:4268-4274 (1998).
Fujisaku et al., "Genomic organization and polymorphisms of the human C3d/Epstein-Barr virus receptor," J Biol Chem. 264:2118-25 (1989).
Fukuoka et al., "Molecular cloning of murine decay accelerating factor by immunoscreening," International Immunology. 8:379-385 (1996).
Girardi et al., "Complement C5a receptors and neutrophils mediate fetal injury in the antiphospholipid syndrome," J Clin Invest. 112(11):1644-54 (2003).
Gomez et al., "Role of ischaemic preconditioning in liver regeneration following major liver resection and transplantation," World J Gastroenterol. 13(5):657-70 (2007).
Goodford, "A computational procedure for determining energetically favorable binding sites on biologically important macromolecules," *J. Med. Chem.* 28: 849-857, 1985.
Gordon, "B-cell signalling via the C-type lectins CD23 and CD72," Immunol Today. 15(9):411-417 (1994).
Greene et al., "Partial hepatectomy in the mouse: technique and perioperative management," J Invest Surg. 16:99-102 (2003).
Greenspan et al., "Defining epitopes: Its not as easy as it seems," Nat Biotechnol. 17:936-937 (1999).
Grzesiek et al., "Improved 3D triple-resonance NMR techniques applied to a 31-kDa protein," J Magn Reson. 96:432-40 (1992).
Guthridge et al., "Epitope mapping using the X-ray crystallographic structure of complement receptor type 2 (CR2)/CD21: Identification of a highly inhibitory monoclonal antibody that directly recognizes the CR2-C3d interface," J Immunol. 167:5758-5766 (2001).
Guthridge et al., "Structural studies in solution of the recombinant N-terminal pair of short consensus/complement repeat domains of complement receptor type 2 (CR2/CD21) and interactions with its ligand C3dg," Biochemistry. 40:5931-5941 (2001).

(56) References Cited

OTHER PUBLICATIONS

Haan et al., "Different functional domains in the cytoplasmic tail of glycoprotein B are involved in Epstein-Barr virus-induced membrane fusion," Virology. 290:106-14 (2001).
Haddad et al., "Depletion of glycoprotein gp85 from virosomes made with Epstein-Barr virus proteins abolishes their ability to fuse with virus receptor-bearing cells," J Virol. 63:4998-5005 (1989).
Hageman et al., "A common haplotype in the complement regulatory gene factor H (HF1/CFH) predisposes individuals to age-related macular degeneration," Proc Natl Acad Sci USA. 102(20):7227-32 (2005).
Haines et al., "Complement factor H variant increases the risk of age-related macular degeneration," Science. 308(5720):419-21 (2005).
Ham et al., "Studies on destruction of red blood cells. II. Chronic hemolytic anemia with paroxysmal nocturnal hemoglobinuria: certain immunological aspects of the hemolytic mechanism with special reference to serum complement," J Clin Invest. 18:657-72 (1939).
Hampton Research, Catalog, 5 & 7 (2001).
Hampton Research, Crystal Screen User Guide, 27632 El Lazo Road, Laguna Niguel, California, 1991 (4 pages).
Hannan et al., "Mutational analysis of the complement receptor type 2 (CR2/CD21)-C3d interaction reveals a putative charged SCR1 binding site for C3d," J Mol Biol. 346(3):845-58 (2005).
Hannan et al., "Structure of complement receptor (CR) 2 and CR2-C3d complexes," Biochem Soc Trans. 30:983-9 (2002).
Harada et al., "Antithrombin reduces ischemia/reperfusion injury of rat liver by increasing the hepatic level of prostacyclin," Blood. 93:157-64 (1999).
Harlow et al., Proteolytic Fragments of Antibodies. *Antibodies: A Laboratory Manual*. 626-629 (1988).
Harris et al., "Tailoring anti-complement therapeutics," Biochem Soc Trans. 30(6):1019-26 (2002).
Hautekeete et al., "Microvesicular steatosis of the liver," Acta Clin Belg. 45(5):311-326 (1990). Abstract Only.
He et al., "Delivery of antioxidative enzyme genes protects against ischemia/reperfusion-induced liver injury in mice," Liver Transpl. 12:1869-79 (2006).
Hebell et al., "Suppression of the immune response by a soluble complement receptor of B lymphocytes," Science. 254:102-105 (1991).
Heinen et al., "Factor H-related protein 1 (CFHR-1) inhibits complement C5 convertase activity and terminal complex formation," Blood. 114(12):2439-47 (2009).
Helling et al., "Partial hepatectomy with or without endotoxin does not promote apoptosis in the rat liver," J Surg Res. 116:1-10 (2004).
Helling, "Liver failure following partial hepatectomyn" HPB (Oxford). 8:165-74 (2006).
Heyman, "Regulation of antibody responses via antibodies, complement, and Fc receptors," Ann Rev Immunol. 18:709-737 (2000).
Higgins et al., "A soluble chimeric complement inhibitory protein that possesses both decay-accelerating and factor I cofactor activities," J Immunol. 158(6):2872-81 (1997).
Higgins et al., "Experimental pathology of the liver. 1. Restoration of the liver of the white rat following partial surgical removal," Arch Pathol. 12:186-202 (1931).
Hill et al., "Sustained response and long-term safety of eculizumab in paroxysmal nocturnal hemoglobinuria," Blood. 106:2559-65 (2005).
Hill, "Eculizumab for the treatment of paroxysmal nocturnal hemoglobinuria," Clin Adv Hematol Oncol. 3(11):849-50 (2005).
Holers et al., "The alternative pathway of complement in disease: Opportunities for therapeutic targeting," Mol. Immunol. 41:147-152 (2004).
Holers, Complement Receptors. *The Year in Immunology 1988. Cellular, Molecular and Clinical Aspects*. Cruse et al., 4:231-240 (1989).
Holers, Complement. *Clinical Immunology, Principles and Practice*. Mosby ed. 363-91 (1996).
Homeister et al., "Soluble complement receptor type 1 prevents human complement-mediated damage of the rabbit isolated heart," J Immunol. 150(3):1055-1064 (1993).
Hori et al., "Crry, a complement regulatory protein, modulates renal interstitial disease induced by proteinuria," Kidney Int. 56:2096-2106 (1999).
Hsu et al., "Chronic progression of tubulointerstitial damage in proteinuric renal disease is mediated by complement activation: a therapeutic role for complement inhibitors?" J Am Soc Nephrol. 14:S186-91 (2003).
Huang et al., "A novel targeted inhibitor of the alternative pathway of complement," Mol Immunol. 44(16):3947 (Abstract Only: No. P31) (2007).
Huang et al., "Insights into the human CD59 complement binding interface toward engineering new therapeutics," J Biol Chem. 280(40):34073-9 (2005).
Hughes et al., "Monoclonal antibody targeting of liposomes to mouse lung in vivo," Cancer Res. 49(22):6214-20 (1989).
Humar et al., "Liver regeneration after adult living donor and deceased donor split-liver transplants," Liver Transpl. 10(3):374-8 (2004).
Humblet et al., "3D database searching and docking strategies," Topics in Drug Design and Discovery. *Annual Reports in Medicinal Chemistry*. Bristol et al., 28:275-284 (1993).
Iida et al., "Identification of the membrane receptor for the complement fragment C3d by means of a monoclonal antibody," J Exp Med. 158:1021-33 (1983).
Iimuro et al., "NFkappaB prevents apoptosis and liver dysfunction during liver regeneration," J Clin Invest. 101(4):802-11 (1998).
Imai et al., "Enhancement of antibody-dependent mechanisms of tumor cell lysis by a targeted activator of complement," Cancer Res. 67(19):9535-9541 (2007).
International Preliminary Report on Patentability and Written Opinion for International Application No. PCT/US2011/041517, dated Dec. 28, 2012 (11 pages).
International Preliminary Report on Patentability and Written Opinion of the International Searching Authority for International Application No. PCT/US2007/014602, dated Dec. 22, 2008 (6 pages).
International Preliminary Report on Patentability and Written Opinion of the International Searching Authority for International Application No. PCT/US2010/040973, dated Jan. 4, 2012 (8 pages).
International Preliminary Report on Patentability and Written Opinion of the International Searching Authority for International Application No. PCT/US2010/055745, dated May 8, 2012 (6 pages).
International Preliminary Report on Patentability and Written Opinion of the International Searching Authority for International Application No. PCT/US2011/036552, dated Nov. 20, 2012 (9 pages).
International Search Report for International Application No. PCT/US2003/36459, dated Sep. 15, 2004 (2 pages).
International Search Report for International Application No. PCT/US2007/014602, dated Mar. 6, 2008 (5 pages).
International Search Report for International Application No. PCT/US2010/040973, dated Oct. 14, 2010 (5 pages).
International Search Report for International Application No. PCT/US2011/036552, dated Jul. 26, 2011 (7 pages).
International Search Report for International Application No. PCT/US2011/041517, dated Nov. 10, 2011 (8 pages).
Jackson et al., "PI3K/Akt activation is critical for early hepatic regeneration after partial hepatectomy," Am J Physiol Gastrointest Liver Physiol. 294:G1401-10 (2008).
Jacobson et al., "Clinical and immunologic features of transient cold agglutinin-hemolytic anemia," Am J Med. 54:514-21 (1973).
Janssen et al., "Structure of C3b reveals conformational changes that underlie complement activity," Nature. 444:213-216 (2006).
Janssen et al., "Structure of compstatin in complex with complement component C3c reveals a new mechanism of complement inhibition," J Biol Chem. 282:29241-7 (2007).
Janzi et al., "Serum microarrays for large scale screening of protein levels," Mol Cell Proteomics. 4(12):1942-7 (2005).
Jin et al., "Interleukin-6 inhibits oxidative injury and necrosis after extreme liver resection," Hepatology. 46:802-12 (2007).
Jin et al., "Paradoxical effects of short- and long-term interleukin-6 exposure on liver injury and repair," Hepatology. 43:474-84 (2006).

(56) References Cited

OTHER PUBLICATIONS

Johswich et al., "Ligand specificity of the anaphylatoxin C5L2 receptor and its regulation on myeloid and epithelial cell lines," J Biol Chem. 281(51):39088-95 (2006).

Jozsi et al., "Attachment of the soluble complement regulator factor H to cell and tissue surfaces: relevance for pathology," Histol Hitopathol. 19:251-8 (2004).

Juhl et al., "Complement killing of human neuroblastoma cells: A cytotoxic monoclonal antibody and its F(ab')2-cobra venom factor conjugate are equally cytotoxic," *Mol Immunol.* 27(10):957-964 (1990).

Kadry et al., "Liver regeneration after adult living donor and deceased donor split-liver transplants," Liver Transpl. 10(8):1078 (2004).

Kalant et al., "C5L2 is a functional receptor for acylation-stimulating protein," J Biol Chem 208(25):23936-44 (2005).

Kalant et al., "The chemoattractant receptor-like protein C5L2 binds the C3a des-Arg77/acylation-stimulating protein," J Biol Chem 278(13):11123-9 (2003).

Kalli et al., "Interaction of iC3b with recombinant isotypic and chimeric forms of CR2," J Immunol. 147(2):590-594 (1991).

Kaplan, "Eculizumab Alexion," Curr Opin Investig Drugs. 3(7):1017-23 (2002).

Khurana et al., "Crystal structure of 2,5-diketo-D-gluconic acid reductase A complexed with NADPH at 2.1-A resolution," Proc Natl Acad Sci 95:6768-6773 (1998).

Kildsgaard et al., "A critical evaluation of the putative role of C3adesArg (ASP) in lipid metabolism and hyperapobetalipoproteinemia," Mol Immunol. 36:869-76 (1999).

Klein et al., "Complement factor H polymorphism in age-related macular degeneration," Science. 308(5720):385-9 (2005).

Koski et al., "Cytolysis of nucleated cells by complement: cell death displays multi-hit characteristics," Proc Natl Acad Sci USA. 80:3816-3820 (1983).

Kovacs et al., "Biophysical investigations of complement receptor 2 (CD21 and CR2)-ligand interactions reveal amino acid contacts unique to each receptor-ligand pair," J Biol Chem. 285:27251-8 (2010).

Kovacs et al., "Mapping of the C3d ligand binding site on complement receptor 2 (CR2/CD21) using nuclear magnetic resonance and chemical shift analysis," J Biol Chem. 284(14):9513-20 (2009).

Kroshus et al., "A recombinant soluble chimeric complement inhibitor composed of human CD46 and CD55 reduces acute cardiac tissue injury in models of pig-to-human heart transplantation," Transplantation. 69(11):2282-9 (2000).

Kroshus et al., "Complement inhibition with an anti-C5 monoclonal antibody prevents acute cardiac tissue injury in an ex vivo model of pig-to-human xenotransplantation," Transplantation. 60(11):1194-202 (1995).

Krushkal et al., "Evolutionary relationships among proteins encoded by the regulator of complement activation gene cluster," Mol Biol Evol. 17(11):1718-30 (2000).

Kuby et al., Antigens. *Immunology (2nd edition).* W H Freeman and Company, 85-96 (1994).

Kundrot, "Which strategy for a protein crystallization project?" Cell Mol Life Science. 61(5):525-536 (2004).

Kuraya et al., "Expression of the complement regulatory proteins CD21, CD55, and CD59 on Burkitt lymphoma lines: Their role in sensitivity to human serum-meidated lysis," Eur J Immunol. 22(7):1871-1876 (1992).

La Flamme et al., "Lack of C3 affects Th2 response development and the sequelae of chemotherapy in schistosomiasis," J Immunol. 170:470-6 (2003).

Lambris et al., "Mapping of the C3d receptor (CR2)-binding site and a neoantigenic site in the C3d domain of the third component of complement," Proc Natl Acad Sci USA. 82(12):4235-4239 (1985).

Law et al., "Action of the C3b-inactivator of the cell-bound C3b," J Immunol. 122(3):759-65 (1979).

Law et al., Complement. *In Focus.* Male, vii-ix (1995).

Lehmann et al., "Complement inhibition by soluble complement receptor type 1 improves microcirculation after rat liver transplantation," Transplantation. 66:717-22 (1998).

Lehmann et al., "Impact of inhibition of complement by sCR1 on hepatic microcirculation after warm ischemia," Microvasc Res. 62:284-92 (2001).

Leivo et al., "C3d fragment of complement interacts with laminin and binds to basement membranes of glomerulus and trophoblast," J Cell Biol. 103:1091-100 (1986).

Lemoli et al., "Immunological effects of omalizumab in chronic urticaria: a case report," J Invest Allergol Clin Immunol. 20(3):252-4 (2010).

Leu et al., "Triggering of interferon γ-primed macrophages by various known complement activators for nonspecific tumor cytotoxicity," *Cell Immunol.* 106:114-121 (1987).

Linton et al., "therapeutic efficacy of a novel membrane-targeted complement regulator in antigen-induced arthritis in the rat," Arthritis Rheum. 43(11):2590-7 (2000).

Liszewski et al., "Complement inhibitors as therapeutic agents," Clin Immunol Newsletter. 17(12):168-73 (1997).

Litzinger et al., "Biodistribution and immunotargetability of ganglioside-stabilized dioleoylphosphatidylethanolamine liposomes," Biochimica et Biophysica Acta. 1104:179-87 (1992).

Lowell et al., "Mapping of the Epstein-Barr virus and C3dg binding sites to a common domain on complement receptor type 2," J Exp Med. 170(6):1931-1946 (1989).

Luqman et al., "The antileukemia activity of a human anti-CD40 antagonist antibody, HCD122, on human chronic lymphocytic leukemia cells," Blood. 112(3):711-20 (2008).

Luxembourg et al., "Modulation of signaling via the B cell antigen receptor by CD21, the receptor for C3dg and EBV," J Immunol. 153:4448-57 (1994).

Lyubarsky et al., "Recovery phase of the murine rod photoresponse reconstructed from electroretinographic recordings," J Neurosci. 16(2):563-571 (1996).

Lyubchenko et al., "Coligation of the B cell receptor with complement receptor type 2 (CR2/CD21) using its natural ligand C3dg: activation without engagement of an inhibitory signaling pathway," J Immunol. 174:3264-72 (2005).

MacLaren et al., "Adipokines and the immune system: an adipocentric view," Adv Exp Med Biol. 632:1-21 (2008).

Markiewski et al., "C3a and C3b activation products of the third component of complement (C3) are critical for normal liver recovery after toxic injury," J Immunol. 173:747-754 (2004).

Martin et al., "Determination of the role for CD21 during Epstein-Barr virus infection of B-lymphoblastoid cells," J Virol. 68(8):4716-4726 (1994).

Martin et al., "Determination of the structural basis for selective binding of Epstein-Barr virus to human complement receptor type 2," J Exp Med. 174:1299-1311 (1991).

Maslowska et al., "Novel roles for acylation stimulating protein/C3adesArg: a review of recent in vitro and in vivo evidence," Vitam Horm. 70:309-32 (2005).

Mastellos et al., "A novel role of complement: mice deficient in the fifth component of complement (C5) exhibit impaired liver regeneration," J Immunol. 166(4):2479-86 (2001).

Mastellos et al., "Novel monoclonal antibodies against mouse C3 interfering with complement activation: description of fine specificity and applications to various immunoassays," Mol Immunol. 40(16):1213-21 (2004).

Matsumoto et al., "Intersection of the complement and immune systems: A signal transduction complex of the B lymphocyte-containing complement receptor type 2 and CD19," J Exp Med. 173(1):55-64 (1991).

Matsuo et al., "Complement in renal tubulointerstitial injuries," Proceedings of the 35th Complement Symposium 21-22 (1998).

McPherson, "Current approaches to macromolecular crystallization," Eur J Biochem. 189(1):1-23 (1990).

Mendrick et al., "I. induction of proteinuria in the rat by a monoclonal antibody against SGP-115/107," Kidney Int. 33:818-30 (1988).

Mendrick et al., "Monoclonal antibodies against rat glomerular antigens: production and specificity," Lab Invest. 49(1):107-17 (1983).

(56) References Cited

OTHER PUBLICATIONS

Meri et al., "Structural composition and functional characterization of soluble CD59: heterogeneity of the oligosaccharide and glycophosphoinositol (GPI) anchor revealed by laser-desorption mass spectrometric analysis," Biochem J. 316(3):923-35 (1996).
Moir et al., "B cells of HIV-1-infected patients bind virions through CD21-complement interactions and transmit infectious virus to activated T cells," J Exp Med. 192(5):637-646 (2000).
Mold et al., "Activation of the alternative complement pathway by EBV and the viral envelope glycoprotein, gp350," J Immunol. 140(11):3867-3874 (1988).
Molesworth et al., "Epstein-Barr virus gH is essential for penetration of B cells but also plays a role in attachment of virus to epithelial cells," J Virol. 74(14):6324-32 (2000).
Molina et al., "Analysis of C3b/C3d binding sites and factor I cofactor regions within mouse complement receptor 1 and 2," J Immunol. 153(2):789-795 (1994).
Molina et al., "Analysis of Epstein-Barr virus-binding sites on complement receptor 2 (CR2/CD21) using human-mouse chimeras and peptides," J Biol Chem. 266(19-20):12173-9 (1991).
Molina et al., "Characterization of a complement receptor 2 (CR2, CD21) ligand binding site for C3. An initial model of ligand interaction with two linked short consensus repeat modules," J Immunol. 154:5426-5435 (1995).
Molina et al., "Markedly impaired humoral immune response in mice deficient in complement receptors 1 and 2," Proc Natl Acad Sci USA. 93:3357-3361 (1996).
Mollnes et al., "Identification of a human C5 beta-chain epitope exposed in the native complement component but concealed in the SC5b-9 complex," Scand J Immunol. 28:307-12 (1988).
Moongkarndi et al., "Immunological and functional properties of two monoclonal antibodies against human C5," Immunobiol. 165:323 (1983).
Moongkarndi et al., "Monoclonal antibodies against the fifth component of human complement," Immunobiol. 162:397 (1982).
Moore et al., "Hydrodynamic, electron microscopic, and ligand-binding analysis of the Epstein-Barr virus/C3dg receptor (CR2)," J Biol Chem. 264:20576-82 (1989).
Moore et al., "Inhibition of Epstein-Barr virus infection In Vitro and In Vivo by soluble CR2 (CD21) containing two short consensus repeats," J Virol. 65(7):3559-3565 (1991).
Moore et al., "Molecular cloning of the cDNA encoding the Epstein-Barr virus/C3d receptor (complement receptor type 2) of human B lymphocytes," Proc Natl Acad Sci USA. 84:9194-8 (1987).
Moran et al., "Human recombinant soluble decay accelerating factor inhibits complement activation in vitro and in vivo," J Immunol. 149:1736-1743 (1992).
Morgan, "Clinical complementology: recent progress and future trends," Eur J Clin Invest. 24(4):219-28 (1994).
Morikis et al., "The electrostatic nature of C3d-complement receptor 2 association," J Immunol. 172:7537-47 (2004).
Mullen et al., "Structure of the Epstein-Barr virus gp42 protein bound to the MHC class II receptor HLA-DR1," Mol Cell. 9:375-85 (2002).
Mulligan et al., "Endothelial targeting and enhanced antiinflammatory effects of complement inhibitors possessing sialyl Lewisx moieties," J Immunol 162(8):4952-9 (1999).
Murray et al., "Functional bioactive recombinant acylation stimulating protein is distinct from C3a anaphylatoxin," J Lipid Res. 38:2492-501 (1997).
Murray et al., "Mice lacking acylation stimulating protein (ASP) have delayed postprandial triglyceride clearance," J Lipid Res. 40:1671-6 (1999).
Murray et al., "Reduced body weight, adipose tissue, and leptin levels despite increased energy intake in female mice lacking acylation-stimulating protein," Endocrinology. 141(3):1041-9 (2000).
Müller-Eberhard, "Molecular organization and function of the complement system," Ann Rev Biochem. 57:321-47 (1988).
Nagar et al., "X-ray crystal structure of C3d: A C3 fragment and ligand for complement receptor 2," Science. 280(5367):1277-81 (1998).
NCBI Blast for Accession No. NP_001006659.1. Retrieved on Dec. 26, 2013 (5 pages).
NCBI Blast for Accession No. NP_031784.1. Retrieved on Dec. 26, 2013 (4 pages).
NCBI Blast for GenBank Accession No. U09969. Retrieved on Nov. 15, 2013 (3 pages).
NCBI Blast for UniProtKB/Swiss-Prot Accession No. O55186. Retrieved on Nov. 13, 2013 (5 pages).
NCBI Blast for UniProtKB/Swiss-Prot Accession No. P00746. Retrieved on Nov. 13, 2013 (14 pages).
NCBI Blast for UniProtKB/Swiss-Prot Accession No. P00751. Retrieved on Nov. 13, 2013 (1 page).
NCBI Blast for UniProtKB/Swiss-Prot Accession No. P01024. Retrieved on Nov. 13, 2013 (29 pages).
NCBI Blast for UniProtKB/Swiss-Prot Accession No. P01027. Retrieved on Nov. 13, 2013 (13 pages).
NCBI Blast for UniProtKB/Swiss-Prot Accession No. P03953. Retrieved on Nov. 13, 2013 (6 pages).
NCBI Blast for UniProtKB/Swiss-Prot Accession No. P04004. Retrieved on Nov. 13, 2013 (14 pages).
NCBI Blast for UniProtKB/Swiss-Prot Accession No. P04186. Retrieved on Nov. 13, 2013 (9 pages).
NCBI Blast for UniProtKB/Swiss-Prot Accession No. P05155. Retrieved on Nov. 13, 2013 (29 pages).
NCBI Blast for UniProtKB/Swiss-Prot Accession No. P06909. Retrieved on Nov. 13, 2013 (19 pages).
NCBI Blast for UniProtKB/Swiss-Prot Accession No. P08173. Retrieved on Nov. 13, 2013 (4 pages).
NCBI Blast for UniProtKB/Swiss-Prot Accession No. P08603. Retrieved on Nov. 13, 2013 (1 page).
NCBI Blast for UniProtKB/Swiss-Prot Accession No. P10909. Retrieved on Nov. 13, 2013 (21 pages).
NCBI Blast for UniProtKB/Swiss-Prot Accession No. P11680. Retrieved on Nov. 13, 2013 (5 pages).
NCBI Blast for UniProtKB/Swiss-Prot Accession No. P13987. Retrieved on Nov. 13, 2013 (16 pages).
NCBI Blast for UniProtKB/Swiss-Prot Accession No. P15529. Retrieved on Nov. 13, 2013 (30 pages).
NCBI Blast for UniProtKB/Swiss-Prot Accession No. P17927. Retrieved on Nov. 13, 2013 (1 page).
NCBI Blast for UniProtKB/Swiss-Prot Accession No. P27918. Retrieved on Nov. 13, 2013 (13 pages).
NCBI Blast for UniProtKB/Swiss-Prot Accession No. P29788. Retrieved on Nov. 13, 2013 (10 pages).
NCBI Blast for UniProtKB/Swiss-Prot Accession No. P58019. Retrieved on Nov. 13, 2013 (5 pages).
NCBI Blast for UniProtKB/Swiss-Prot Accession No. P97290. Retrieved on Nov. 13, 2013 (6 pages).
NCBI Blast for UniProtKB/Swiss-Prot Accession No. Q06890. Retrieved on Nov. 13, 2013 (9 pages).
NCBI Blast for UniProtKB/Swiss-Prot Accession No. Q61475. Retrieved on Nov. 13, 2013 (11 pages).
NCBI Blast for UniProtKB/Swiss-Prot Accession No. Q9P296. Retrieved on Nov. 13, 2013 (9 pages).
NCBI Protein Database Accession No. P08173. Retrieved Feb. 18, 2014 (4 pages).
NCBI Protein Database Accession No. P13987. Retrieved Feb. 18, 2014 (12 pages).
NCBI Protein Database Accession No. P15529. Retrieved Feb. 18, 2014 (21 pages).
NCBI Protein Database Accession No. P58019. Retrieved Feb. 18, 2014 (4 pages).
Nemerow et al., "Identification and characterization of the Epstein-Barr virus receptor on human B lymphocytes and its relationship to the C3d complement receptor (CR2)," J Virol. 55(2):347-51 (1985).
Nemerow et al., "Identification of an epitope in the major envelope protein of Epstein-Barr virus that mediates viral binding to the B lymphocyte EBV receptor (CR2)," Cell. 56:369-77 (1989).
Nemerow et al., "Identification of gp350 as the viral glycoprotein mediating attachment of Epstein-Barr virus (EBV) to the EBV/C3d

(56) References Cited

OTHER PUBLICATIONS receptor of B cells: sequence homology of gp350 and C3 complement fragment C3d," J Virol. 61(5):1416-20 (1987).
Ngo et al., Computational Complexity, Protein Structure Prediction, and the Levinthal Paradox. *The Protein Folding Problem and Tertiary Structure Prediction.* Merz et al., 491-495 (1994).
Niemann et al., "The use of monoclonal antibodies as probes of the three-dimensional structure of human complement factor D," J Immunol. 132(2):809-15 (1984).
Nozaki et al., "Drusen complement components C3a and C5a promote choroidal neovascularization," Proc Natl Acad Sci USA. 103(7):2328-2333 (2006).
Oglesby et al., "Membrane cofactor protein (CD46) protects cells from complement-mediated attack by an intrinsic mechanism," J Exp Med. 175:1547-51 (1992).
Okano, "Epstein-Barr virus infection and its role in the expanding spectrum of human diseases," Acta Paediatr. 87:11-18 (1998).
Paglialunga et al., "Reduced adipose tissue triglyceride synthesis and increased muscle fatty acid oxidation in C5L2 knockout mice," J Endocrinol. 194:293-304 (2007).
Paixao-Cavalcante et al., "Factor H facilitates the clearance of GBM bound iC3b by controlling C3 activation in fluid phase," Mol Immunol. 46:1942-50 (2009).
Pascual et al., "A monoclonal antibody which blocks the function of factor D of human complement," J Immunol Methods. 127:263-9 (1990).
Pascual et al., "Inhibition of complement alternative pathway in mice with Fab antibody to recombinant adipsin/factor D," Eur J Immunol. 23:1389-92 (1993).
Patel et al., "Pexelizumab: a novel therapy for myocardial ischemia-reperfusion," Drugs Today (Barc). 41(3):165-70 (2005).
Pervushin et al., "Attenuated T2 relaxation by mutual cancellation of dipole-dipole coupling and chemical shift anisotropy indicates an avenue to NMR structures of very large biological macromolecules in solution," Proc Natl Acad Sci USA. 94:12366-71 (1997).
Petersen et al., "The mannan-binding lectin pathway of complement activation: biology and disease association," Mol Immunol. 38:133-49 (2001).
Piatesi et al., "Immunological optimization of a generic hydrophobic pocket for high affinity hapten binding and Diels-Alder activity," Chembiochem. 5(4):460-466 (2004).
Pietersz et al., "Antibody conjugates for the treatment of cancer," Immunolog Reviews. 129:57-80 (1992).
Poznansky et al., "The difference between human C3F and C3S results from a single amino acid change from an asparagine to an aspartate residue at position 1216 on the α-chain of the complement component C3," J Immunol. 143(4):1254-1258 (1989).
Preissner, "Structure and biological role of vitronectin," Annu Rev Cell Biol. 7:275-310 (1991).
Prodeus et al., "A critical role for complement in maintenance of self-tolerance," Immunity. 9(5):721-731 (1998).
Prodinger et al., "Characterization of C3dg binding to to a recess formed between short consensus repeats 1 and 2 of complement receptor type 2 (CR2; CD21)," J Immunol. 161:4604-4610 (1998).
Prota et al., "The crystal structure of human CD21: Implications for Epstein-Barr virus and C3d binding," Proc Natl Acad Sci USA. 99:10641-6 (2002).
Quigg et al., "Blockade of antibody-induced glomerulonephritis with Crry-Ig, a soluble murine complement inhibitor," J Immunol. 160(9):4553-60 (1998).
Quigg et al., "Production and fuctional analysis of rat CD59 and chimeric CD59-Crry as active soluble proteins in Pichia pastoris," Immunol. 99(1):46-53 (2000).
Rabinovici et al., "Role of complement in endotoxin/platelet-activating factor-induced lung injury," J Immunol. 149(5):1744-50 (1992).
Ramm et al., "Transmembrane channel formation by complement: functional analysis of the number of C5b6, C7, C8, and C9 molecules required for a single channel," Pro Natl Acad Sci. 79(15):4751-5 (1982).

Rao et al., "OKB7, a monoclonal antibody that reacts at or near the C3d binding site of human CR2," Cell Immunol. 93(2):549-555 (1985).
Reeck et al., "Homology in proteins and nucleic acids: A terminology muddle and a way out of it," Cell. 50:667 (1987).
Rehrig et al., "Complement inhibitor, complement receptor 1-related gene/protein y-Ig attenuates intestinal damage after the onset of mesenteric ischemia/reperfusion injury in mice," J Immunol. 167:5921-7 (2001).
Rinder et al., "Blockade of C5a and C5b-9 generation inhibits leukocyte and platelet activation during extracorporeal circulation," J Clin Invest. 96(3):1564-72 (1995).
Rioux, "TP-10 AVANT immunotherapeutics," Curr Opin Invest Drugs 2(3):364-71 (2001).
Risitano et al., "TT30, a novel regulator of the complement alternative pathway (CAP), inhibits hemolysis of paroxysmal nocturnal hemoglobinuria (PNH) erythrocytes and prevents upstream C3 binding on their surface in an in vitro model," <https://ash.confex.com/ash/2009/webprogram/Paper19102.html>, retrieved on Dec. 26, 2013 (2 pages).
Rittershaus et al., "Recombinant glycoproteins that inhibit complement activation and also bind the selectin adhesion molecules," J Biol Chem. 274(16):11237-44 (1999).
Roffler et al., "Anti-neoplastic glucuronide prodrug treatment of human tumor cells targeted with a monoclonal antibody-enzyme conjugate," Biochem Pharmacol. 42:2062-2065 (1991).
Rohrer et al., "Eliminating complement factor D reduces photoreceptor susceptibility to light-induced damage," Invest Ophthalmol Vis Sci. 48(11):5282-9 (2007).
Rohrer et al., "Role of neurotrophin receptor TrkB in the maturation of rod photoreceptors and establishment of synaptic transmission to the inner retina," J Neurosci. 19(20):8919-8930 (1999).
Ross et al., "Macrophage cytoskeleton association with CR3 and CR4 regulates receptor mobility and phagocytosis of iC3b-opsonized erythrocytes," J Leukoc Biol. 51(20):109-117 (1992).
Rother et al., "Discovery and development of the complement inhibitor eculizumab for the treatment of paroxysmal nocturnal hemoglobinuria," Nat Biotechnol. 25(11):1256-64, 1488 (2007).
Rothlein et al., "The requirement for lymphocyte function-associated antigen 1 in homotypic leukocyte adhesion stimulated by phorbol ester," J Exp Med. 163(5):1132-49 (1986).
Rudikoff et al., "Single amino acid subsitution altering antigen-binding specificity," Proc Natl Acad Sci USA. 79(6):1979-19783 (1982).
Rushmere et al., "Production and functional characterization of a soluble recombinant form of mouse CD59," Immunol. 99(2):326-32 (2000).
Sahu et al., "Identification of multiple sites of interaction between heparin and the complement system," Mol Immunol. 30(7):679-84 (1993).
Salerno et al., "A soluble chimeric inhibitor of C3 and C5 convertases, complement activation blocker-2, prolongs graft survival in pig-to-rhesus monkey heart transplantation," Xenotransplantation. 9(2):125-34 (2002).
Santiago-Raber et al., "Type-I interferon receptor deficiency reduces lupus-like disease in NZB mice," J Exp Med. 197:777-88 (2003).
Satoh et al., "Energy metabolism regeneration in transgenic mouse liver expressing creatine kinase after major hepatectomy," Gastroenterology. 101:1166-74 (1996).
Schwarzenbacher et al., "Crystal structure of human b2-glycoprotein I: implications for phospholipid binding and the antiphospholipid syndrome," EMBO J. 18:6228-39 (1999).
Scola et al., "The human complement fragment receptor, C5L2, is a recycling decoy receptor," Mol Immunol. 46:1149-62 (2009).
Selzner et al., "Failure of regeneration of the steatotic rat liver: disruption at two different levels in the regeneration pathway," Hepatology. 31:35-42 (2000).
Senter et al., "Generation of 5-fluorouracil from 5-fluorocytosine by monoclonal antibody-cytosine deaminase conjugates," Bioconjugate Chem. 2:447-451 (1991).
Senter et al., "Generation of cytotoxic agents by targeted enzymes," Bioconjugate Chem. 4:3-9 (1993).

(56) References Cited

OTHER PUBLICATIONS

Seya et al., "Limited proteolysis of complement protein C3b by regulatory enzyme C3b inactivator: Isolation and characterization of a biologically active fragment, C3d,g," J Biochem. 97(1):373-382 (1985).
Sharkey et al., "Biodistribution and radiation dose estimates for yttrium- and iodine-labeled monoclonal antibody IgG and fragments in nude mice bearing human colonic tumor xenografts," Cancer Res. 50:2330-2336 (1990).
Sharkey et al., "Rapid blood clearance of immunoglobulin G2a and immunoglobulin G2b in nude mice," Cancer Res. 51:3102-3107 (1991).
Sharma et al., "Identification of three physically and functionally distinct binding sites for C3b in human complement Factor H by deletion mutagenesis," Proc Natl Acad Sci USA. 93(20):10996-11001 (1996).
Sheerin et al., "Leaked protein and interstitial damage in the kidney: is complement the missing link?" Clin Exp Immunol. 130(1):1-3 (2002).
Sigala et al., "Histological and lipid peroxidation changes after administration of 2-acetylaminofluorene in a rat liver injury model following selective periportal and pericentral damage," Toxicology. 196:155-63 (2004).
Skjodt et al., "MBL/Ficolin assocaited protein-1 (MAP-1) may function as a local lectin pathway specific complement inhibitor," Mol Immunol. 47:2229-30 (2010).
Smith et al., "Membrane-targeted complement inhibitors," Mol Immunol. 38:249-55 (2001).
Sokoloff et al., "Targeting of cancer cells with monoclonal antibodies specific for C3b(ii)," Cancer Immunol and Immunother. 49(10):551-62 (2000).
Song et al., "Complement receptor 2-mediated targeting of complement inhibitors to sites of complement activation," J Clin Invest. 111(12):1875-1885 (2003).
Spriggs et al., "The extracellular domain of the Epstein-Barr virus BZLF2 protein binds the HLA-DR beta chain and inhibits antigen presentation," J Virol. 70:5557-63 (1996).
Strey et al., "The proinflammatory mediators C3a and C5a are essential for liver regeneration," J Exp Med. 198(6):913-23 (2003).
Stryer et al., Levels of Structure in Protein Architecture. *Biochemistry (3rd edition)*. W H Freeman Company, 31-33 (1998).
Sugita et al., "Recombinant soluble CD59 inhibits reative haemolysis with complement," Immunol. 82(1):34-41 (1994).
Supplementary European Search Report for European Application No. 03796403.8, dated Jul. 3, 2006 (4 pages).
Supplementary European Search Report for European Application No. 10794833.3 , dated Nov. 28, 2013 (8 pages).
Supplementary European Search Report for European Patent Application No. EP11798880.8, dated Jan. 7, 2014 (13 pages).
Supplementary Partial European Search Report for European Application No. 03796403.8, dated Apr. 3, 2006 (3 pages).
Szakonyi et al., "Structure of complement receptor 2 in complex with its C3d ligand," Science. 292:1725-1728 (2001).
Szakonyi et al., "Structure of the Epstein-Barr virus major envelope glycoprotein," Nature Struct Mol Biol. 13:996-1001 (2006).
Takahashi et al., "Mouse complement receptors type 1 (CR1 ;CD35) and type 2 (CR2;CD21): expression on normal B cell subpopulations and decreased levels during the development of autoimmunity in MRL/lpr mice," J Immunol. 159:1557-69 (1997).
Takeda et al., "Number of hits necessary for complement-mediated hemolysis," Microbiol Immunol. 30(5):461-8 (1986).
Tamerius et al., "Detection of a neoantigen on human C3bi and C3d by monoclonal antibody," J Immunol. 135(3):2015-2019 (1985).
Tanhehco et al., "The anti-factor D antibody, MAb 166-32, inhibits the alternative pathway of the human complement system," Transplant Proc. 31(55):2168-71 (1999).
Tanner et al., "Epstein-Barr virus gp350/220 binding to the B lymphocyte C3d receptor mediates adsorption, capping, and endocytosis," Cell. 50:203-13 (1987).

Taub, "Liver regeneration: from myth to mechanism," Nat Rev Mol Cell Biol. 5:836-47 (2004).
Ten et al., "The signal transduction pathway of CD23 (FceRIIb) targets IkB kinase," J Immunol. 163(7):3851-7 (1999).
Teoh et al., "Dual role of tumor necrosis factor-alpha in hepatic ischemia-reperfusion injury: studies in tumor necrosis factor-alpha gene knockout mice," Hepatology. 39:412-21 (2004).
Thomas et al., "Inhibition of complement activity by humanized anti-C5 antibody and single-chain Fv," Mol Immunol. 33(17-18):1389-401 (1996).
Thurman et al., "Lack of functional alternative complement pathway ameliorates ischemic acute renal failure in mice," J Immunol. 170: 1517-1523, 2003.
Tian et al., "Kupffer cell-dependent TNF-alpha signaling mediates injury in the arterialized small-for-size liver transplantation in the mouse," Proc Natl Acad Sci USA. 103(12):4598-603 (2006).
Tolnay et al., "Complement receptor 2 in the regulation of the immune response," Clin Immunol Immunopathol. 88:123-32 (1998).
Tosic et al., "Preparation of monoclonal antibodies to C3b by immunization with C3b(i)-sepharose," J Immunol Methods. 120:241-9 (1989).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," Proc Natl Acad Sci USA. 97(15):8548-53 (2000).
Tuveson et al., "Molecular interactions of complement receptors on B lymphocytes: a CR1/CR2 complex distinct from the CR2/CD19 complex," J Exp Med. 173:1083-9 (1991).
Ueda et al., "Probing functional sites on complement protein B with monoclonal antibodies," J. Immunol. 138: 1143-1149, 1987.
Van der Elsen et al., "A crystal structure of the complex between human complement receptor 2 and its ligand C3d," Science. 332:608-611 (2011).
Van Harmelen et al., "Mechanisms involved in the regulation of free fatty acid release from isolated human fat cells by acylation-stimulating protein and insulin," J Biol Chem. 274(26):18243-51 (1999).
Vranken et al., "The CCPN data model for NMR spectroscopy: development of a software pipeline," Proteins. 59:687-96 (2005).
Wang et al., "Amelioration of Lupus-like autoimmune disease in NZB/W $F_1$ mice after treatment with a blocking monoclonal antibody specific for complement component C5," Proc Natl Acad Sci USA. 93(16):8563-8 (1996).
Wang et al., "Anti-C5 monoclonal antibody therapy prevents collagen-induced arthritis and ameoliorates established disease," Proc Natl Acad Sci USA. 92(19):8955-9 (1995).
Ward et al., "Decay-accelerating factor CD55 is identified as the receptor for echovirus 7 using CELICS, a rapid immuno-focal cloning method," EMBO J. 13(21):5070-4 (1994).
Watanabe et al., "Co-protective effect of Crry and CD59 in rat kidney against complement attack," Proceedings of the Joint Academic Meeting of the Complement Symposium and Japanese Society for Host Defense Research, 37(11):19-20 (2000).
Weis et al., "Identification of a 145,000 Mr membrane protein as the C3d receptor (CR2) of human B lymphocytes," Proc Natl Acad Sci USA. 81:881-5 (1984).
Weis et al., "Identification of a partial cDNA clone for the C3d/Epstein-Barr virus receptor of human B lymphocytes: homology with the receptor for fragments C3b and C4b of the third and fourth components of complement," Proc Natl Acad Sci USA. 83:5639-43 (1986).
Weis et al., "Structure of the human B lymphocyte receptor for C3d and the Epstein-Barr virus and relatedness to other members of the family of C3/C4 binding proteins," J Exp Med. 167:1047-66 (1988).
Weisman et al., "Soluble human complement receptor type 1: in vivo inhibitor of complement suppressing post-ischemic myocardial inflammation and necrosis," Science. 249(4965):146-151 (1990).
Whiss, "Pexelizumab Alexion," Curr Opin Investig Drugs. 3(6):870-7 (2002).
Wiles et al., "NMR studies of a viral protein that mimics the regulators of complement activation," J Mol Biol. 272(2):253-265 (1997).

(56) References Cited

OTHER PUBLICATIONS

Wiseman et al., "Rapid measurement of binding constants and heats of binding using a new titration calorimeter," Anal Biochem. 179:131-7 (1989).

Wittekind et al., "A high sensitivity 3D NMR experiment to correlate amide-proton and nitrogen resonances with the alpha-carbon and beta-carbon resonances in proteins," J Magn Reson. 101:201-5 (1993).

Wullaert et al., "Hepatic tumor necrosis factor signaling and nuclear factor-kappaB: effects on liver homeostasis and beyond," Endocr Rev. 28(4):365-86 (2007).

Xia et al., "Acylation-stimulating protein (ASP) deficiency induces obesity resistance and increased energy expenditure in ob/ob mice," J Biol Chem. 277:45874-9 (2002).

Yamaji et al., "Up-regulation of hepatic heme oxygenase-1 expression by locally induced interleukin-6 in rats administered carbon tetrachloride intraperitoneally," Toxicol Lett. 179:124-9 (2008).

Young et al., "Isolating the Epstein-Barr virus gp350/220 binding site on complement receptor type 2 (CR2/CD21)," J Biol Chem. 282(50):36614-25 (2007).

Young et al., "Molecular basis of the interaction between complement receptor type 2 (CR2/CD21) and Epstein-Barr virus glycoprotein gp350," J Virol. 82:11217-27 (2008).

Yu et al., "Protection of human breast cancer cells from complement-mediated lysis by expression of heterologous CD59," Clin Exp Immunol. 115(1):13-8 (1999).

Zhang et al., "Immunophysical exploration of C3d-CR2(CCP1-2) interaction using molecular dynamics and electrostatics," J Mol Biol. 369:567-83 (2007).

Zhang et al., "Targeting of functional antibody-CD59 fusion proteins to a cell surface," J Clin Invest. 103(1):55-61 (1999).

Zhang et al., "Targeting of functional antibody-decay-accelerating factor fusion proteins to a cell surface," J Biol Chem. 276(29):27290-5 (2001).

Zhong et al., "NIM811, a mitochondrial permeability transition inhibitor, prevents mitochondrial depolarization in small-for-size rat liver grafts," Am J Transplant. 7:1103-11 (2007).

Zhu et al., "Inhibition of tumor growth and metastasis by targeting tumor-associated angiogenesis with antagonists to the receptors of vascular endothelial growth factor," Invest New Drugs. 17(3):195-212 (1999).

Zipfel, "Complement factor H: physiology and pathophysiology," Semin Thromb Hemost. 27(3):191-9 (2001).

Zuiderweg et al., "Heteronuclear three-dimensional NMR spectroscopy of the inflammatory protein C5a," Biochemistry. 28:2387-91 (1989).

\* cited by examiner

FIGURE 5
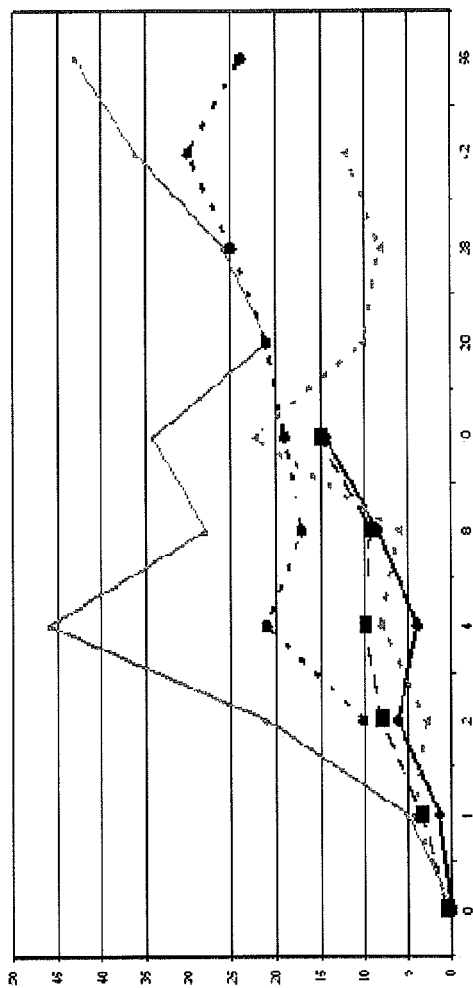
5a
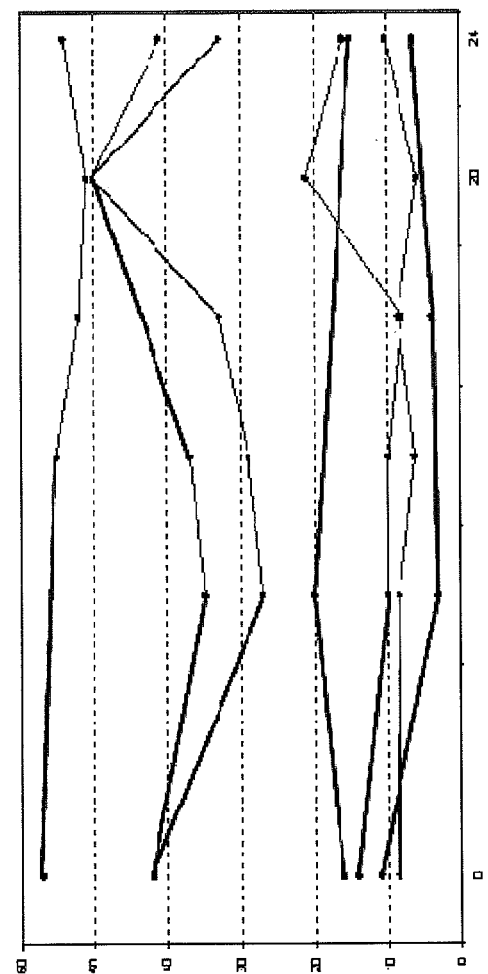
5b

The sequence of activation begins in the upper left corner and proceeds clockwise. See text for details.

The sequence of activation begins in the upper left corner and proceeds clockwise. See text for details.

The sequence of activation begins in the upper left corner and proceeds clockwise. See text for details.

Figure 27 (Time: 0)

Figure 28 (Time: 2 hr)

Figure 29 (Time: 4 hr)

Figure 30 (Time: 24 hr)

Figure 33

CR2 SCR1-4

```
   1     6    11    16    21    26    31    36    41    46    51    56    61
   ISCGS PPPIL NGRIS YYSTP IAVGT VIRYS CSGTF RLIGE KSLLC ITKDK VDGTW DKPAP KC
  63    68    73    78    83    88    93    98   103   108   113   118   123
   EYFNK YSSCP EPIVP GGYKI RGSTP YRHGD SVTFA CKTNF SMNGN KSVWC QANNM WGPTR LPTC
 127   132   137   142   147   152   157   162   167   172   177   182   187
   VSVFP LECPA LPMIH NGHHT SENVG SIAPG LSVTY SCESG YLLVG EKIIN CLSSG KWSAV PPTC
 191   196   201   206   211   216   221   226   231   236   241   246   251
   EEARC KSLGR FPNGK VKEPP ILRVG VTANF FCDEG YRLQG PPSSR CVIAG QGVAW TKMPV C
 252   257   262   267   272   277   282   287   292   297   302   307   312  317
   EEIFE DCNEL PPRRN TEILT GSWSD QTYPE GTQAI YKCRP GYRSL GNVIM VCRKG EWVAL NPLRK C
```

Factor H SCR1-5

```
 318   323   328   333   338   343   348   353   358   363   368   373   378
   QKRPC GHPGD TPFGT FTLTG GNVFE YGVKA VYTCN EGYQL LGEIN YRECD TDGWT NDIPI C
 379   384   389   394   399   404   409   414   419   424   429   434   439
   EVVKC LPVTA PENGK IVSSA MEPDR EYHFG QAVRF VCNSG YKIEG DEEMH CSDDG FWSKE KPKC
 443   448   453   458   463   468   473   478   483   488   493   498
   VEISC KSPDV INGSP ISQKI IYKEN ERFQY KCNMG YEYSE RGDAV CTESG WRPLP SC
 500   505   510   515   520   525   530   535   540   545   550   555   560
   EEKSC DNPYI PNGDY SPLRI KHRTG DEITY QCRNG FYPAT RGNTA KCTST GWIPA PRCTL K
```

TREATMENT OF PAROXYSMAL NOCTURNAL HEMOGLOBINURIA, HEMOLYTIC ANEMIAS AND DISEASE STATES INVOLVING INTRAVASCULAR AND EXTRAVASCULAR HEMOLYSIS

RELATED APPLICATION

This application is submitted under 35 U.S.C. § 371 as a U.S. national stage application of International Application No. PCT/US2010/055745, having an International Filing Date of Nov. 5, 2010, and which claims priority benefit of U.S. Provisional Patent Application Ser. No. 61/280,567, filed Nov. 5, 2009, the content of which is incorporated herein by reference in its entirety.

FIELD OF THE INVENTION

The present invention relates to methods and materials for treatment of subjects suffering disorders that involve abnormal lysis of red blood cells, including intravascular and extravascular hemolysis, utilizing inhibitors of the complement alternative pathway and complement component C3 fragment activity. More particularly, the present invention relates to methods and materials for treatment of subjects with paroxysmal nocturnal hemoglobinuria, aHUS, hemolytic anemias and other disorders that involve complement-mediated hemolysis, and which may involve an extravascular component which is not adequately treated by terminal inhibitors of complement, such as inhibitors of C5 activity.

BACKGROUND OF THE INVENTION

Complement-mediated hemolytic anemia is a significant health problem, and contributes to numerous disorders of the red blood cells, such as paroxysmal nocturnal hemoglobinuria (PNH). PNH is a hematological disorder characterized by the clonal expansion of one or a few hematopoietic stem cells which are incapable of glycosylphosphatidylinositol (GPI)-anchor biosynthesis, due to an acquired somatic mutation in the phosphatidylinositol glycan class A (PIG-A) gene. Affected progeny cells are deficient in all GPI-anchored surface proteins, including complement regulators CD55 and CD59. Thus, PNH red blood cells (RBCs) are vulnerable to activated complement, and particularly to the membrane attack complex (MAC), resulting in chronic intravascular hemolysis with recurrent exacerbations. Other complement-mediated disorders that affect red blood cells include atypical hemolytic uremic syndrome (aHUS); chronic hemolytic anemia; antibody-mediated autoimmune hemolytic anemia; anemia caused by hemoglobinopathies such as sickle cell disease; anemia caused by infection such as malaria; anemia due to transfusion reaction; and cold agglutinin disease (CAD).

Treatment with eculizumab, a monoclonal antibody (Mab) directed against complement component 5 (C5), has been partially effective in PNH and other hematological disorders. However, a significant subpopulation of patients with PNH exhibit suboptimal hematological response to treatment with anti-C5 Mab. In this subpopulation, little improvement of anemia is observed, and some still require blood transfusion, with continuing signs of persistent hemolysis (reticulocytosis, elevated unconjugated bilirubin). Risitano and Rotoli, Biologics, 2:205-222 (2008). The recurrence may be characterized as "breakthroughs" where hemolytic activity may persist despite treatment with terminal complement inhibitors. Hill et al., Blood, 106:2559-65 (2005). For these subjects, a need remains for additional methods and materials for the effective treatment of PNH.

Complement inhibitors are known in the art, and a new class of targeted complement inhibitors has been developed, which allows treatment in a fashion which results in high localized concentrations of inhibitor at the tissue sites where complement is activated, while minimizing potentially adverse systemic effects. This class of inhibitors includes, for example, TT30 (SEQ ID NO:3), TT31 and TT32. TT30 is an immunomodulatory compound which inhibits the complement alternative pathway. TT30 comprises a complement alternative pathway inhibitory portion of Factor H protein, which is targeted to sites of complement activation and inflammation through fusion with a portion of the complement receptor 2 protein (CR2 or CD21) which is known to bind to tissue/cell-fixed fragments of the complement component 3 (C3). TT31 is similar to TT30, but contains an additional copy of the complement alternative pathway inhibitory portion of Factor H protein. TT32 comprises a complement inhibitory portion of complement receptor 1 (CR1), targeted through fusion with the same portion of the CR2 protein. CR1 is known to be a broader inhibitor of complement than is Factor H. TT32 will therefore inhibit not only the complement alternative pathway, but will locally inhibit both the classic and lectin pathways of complement as well. Suitable targeted inhibitors are described in Gilkeson et al., US Patent Publication 2008/0221011, the disclosure of which is hereby specifically incorporated herein by reference.

SUMMARY OF THE INVENTION

Modulation of the complement system represents a therapeutic modality for numerous pathologic conditions associated with complement activation. As summarized above, however, a significant subpopulation of subjects with PNH and other forms of anemia do not optimally respond to treatment with treatment with terminal complement inhibitors, such as the anti-C5 Mab, eculizumab, due in whole or in part to extravascular hemolysis.

The present inventors have found that subjects suffering from complement-mediated disorders that affect red blood cells, such as PNH, that are not effectively or optimally treated with a terminal complement inhibitor surprisingly may be effectively treated with a composition that inhibits the complement alternative pathway, and through this activity block the formation and activity of amplifying C3 convertase on the surface of PNH red blood cells. In certain embodiments, the compositions of the present invention which inhibit the activation of complement component C3 may thereby inhibit not only the amplification loop of the complement alternative pathway, but may also partially inhibit alternative pathway activation via spontaneous C3 'tickover.' In certain, embodiments, in addition to inhibition of the complement alternative pathway, the compositions of the present invention may further exhibit inhibitory effects on other complement pathways, such as the classical and lectin activation pathways.

The present inventors have discovered that subjects with suboptimal hematological response to terminal complement inhibitors, such as eculizumab, may exhibit extravascular hemolysis mediated by complement effector mechanisms other than MAC. Based on flow cytometric analysis of complement fraction 3 (C3) on RBCs, we provide evidence of selective C3 opsonization of GPI-negative red cells. The extent of this phenomenon tends to correlate with the clinical response to eculizumab, and may be the manifestation of a novel phenomenon in the pathophysiology of PNH.

While not being bound by any one theory, targeting the terminal complement at the level of C5 may not protect red blood cells from damage through the early complement components (i.e., C3), which may lead to extravascular hemolysis. It is also believed that treatment with terminal complement inhibitors, such as eculizumab, may allow low-level intravascular hemolysis to continue, sufficient to keep LDH in the high normal range and HgB low normal, possibly by a mechanism that involves accumulation of C5 convertases that eventually can out-compete the terminal complement inhibitor for C5 during normal on-off cycling of the monoclonal antibody. This is supported by the occurrence of pharmacokinetic 'breakthroughs' of hemolysis, which have been reported to occur in patients whose blood level of eculizumab dips below 'trough' concentrations of 35 ug/mL. The inventors believe that breakthroughs may also be caused by other crisis circumstances, such as viral infection or other causes of increased complement activation, which may lead to a disturbance of the balance between eculizumab, C5 and C5 convertase. The inventors believed that the accumulation of C3 fragments on PNH red blood cells contributes to viral-associated breakthrough through activation of cells in the reticuloendothelial system. In addition, though, by binding to C5 at the cell surface interface, treatment with terminal complement inhibitors of hemolytic anemias such as PNH may contribute to the accumulation of C3, C3 convertases, C3 fragments and C5 convertases, which can contribute to the inability of subjects to achieve and stably maintain fully normal serum LDH and HgB levels. Accordingly, the present invention provides methods for the treatment of subjects with complement-mediated hemolysis such as those suffering from PNH. Such methods target early complement activation, and are able to control intravascular hemolysis, as well as reduce or avoid possible extravascular hemolysis resulting from uncontrolled C3 activation and opsonization. The methods and compositions of the present invention may therefore be more effective in treating patients suffering from PNH or other hemolytic anemias, can effectively achieve and maintain normal serum LDH and HgB levels and reduce or eliminate the occurrence of 'breakthrough' hemolytic crises that have been observed in patients treated with terminal complement inhibitors. Thus, the methods and compositions of the present invention may also be more effective for treatment of patients suffering from PNH, while reducing or avoiding the occurrence of such 'breakthrough' hemolytic crises.

In certain embodiments, the present invention comprises a method of treating a subject having paroxysmal nocturnal hemoglobinuria (PNH) or other complement-mediated hemolytic disorder affecting red blood cells, the method comprising administering an effective amount of a composition that inhibits (such as selectively inhibits) the activity of the complement alternative pathway, wherein the composition inhibits local activation of complement component C3 (C3), for example by inhibiting alternative pathway activation by initiation C3 convertase and/or by inhibiting formation and/or activity of amplifying C3 convertase and opsonization of red blood cells by fragments of C3.

In other embodiments, the invention comprises a method of treating a subject exhibiting extravascular hemolysis, which may be due to a complement-mediated hemolytic disorder affecting red blood cells, such as PNH, the method comprising administering an effective amount of a composition that inhibits (such as selectively inhibits) the activity of the complement alternative pathway, wherein the composition inhibits local activation of complement component (C3), for example by inhibiting alternative pathway activation by initiation C3 convertase and/or by inhibiting formation and/or activity of amplifying C3 convertase and opsonization of red blood cells by fragments of C3.

The terminal complement inhibitor selectively inhibits cleavage of complement protein C5, and may be for example, a humanized anti-C5 antibody or antigen-binding fragment thereof, such as eculizumab or pexelizumab. Thus, in certain embodiments, the present invention comprises treatment of a subject having paroxysmal nocturnal hemoglobinuria, wherein the subject has previously been treated with an anti-C5 antibody, such as eculizumab or pexelizumab, but whose PNH disease state and/or symptoms persist.

In certain embodiments, the methods of the present invention comprise treating a subject having a complement-mediated hemolytic disorder affecting red blood cells, such as paroxysmal nocturnal hemoglobinuria (PNH), atypical hemolytic uremic syndrome (aHUS); chronic hemolytic anemia; and cold agglutinin disease (CAD), wherein the subject exhibits at least one of the following characteristics, which characteristics may be symptoms of residual anemia and/or complement-mediated extravascular hemolysis and/or incomplete control of intravascular hemolysis:

a. the subject exhibits signs or symptoms continued loss of red blood cells by ongoing or intermittent intravascular hemolysis and/or extravascular hemolysis;
b. the subject has red blood cells opsonized by fragments of C3;
c. the subject requires periodic blood transfusions;
d. the subject has low normal or below normal levels of hemoglobin;
e. the subject has low normal or below normal levels of platelets;
f. the subject has high normal or above normal reticulocytes;
g. the subject has high normal or above normal bilirubin; or
h. the subject has iron overload or is at risk of iron overload.

The above characteristics can also be used to monitor the subject's progress in response to treatment with complement alternative pathway inhibitors in accordance with the present invention, and to modify the dosage regime if deemed clinically appropriate. In certain embodiments, the subject having a complement-mediated hemolytic disorder affecting red blood cells, such as PNH, has previously been treated with a terminal complement inhibitor, but persists in exhibiting at least one of the above characteristics. In such cases, the present invention provides methods and compositions for avoiding or reducing the occurrence and/or severity of at least one of the above characteristics.

In another aspect, the present invention comprises methods of rendering transfusion independent a subject having a complement-mediated hemolytic disorder affecting red blood cells, such as PNH, where that subject exhibits a suboptimal response to treatment with a terminal complement inhibitor. Such suboptimal response may include the subject exhibiting at least one of the above characteristics of residual anemia and/or complement-mediated extravascular hemolysis. The method comprises administering an effective amount of a composition that inhibits the activity of the complement alternative pathway, wherein the composition inhibits activation of complement component C3 (C3), for example by inhibiting alternative pathway activation by initiation C3 convertase and/or by inhibiting formation and/or activity of amplifying C3 convertase and opsonization of red blood cells by fragments of C3.

In another aspect, the present invention comprises methods of reducing hemolysis in a subject having PNH, the method comprising administering an effective amount of a composition that inhibits activation of complement component C3 (C3), for example by inhibiting alternative pathway activation by initiation C3 convertase and/or by inhibiting formation and/or activity of amplifying C3 convertase, and opsonization of PNH red blood cells by fragments of C3.

In yet another aspect, the present invention comprises methods of reducing residual anemia in a subject having PNH, the method comprising administering an effective amount of a composition that inhibits the activity of the complement alternative pathway, wherein the composition inhibits activation of complement component C3 (C3), for example by inhibiting alternative pathway activation by initiation C3 convertase and/or by inhibiting formation and/or activity of amplifying C3 convertase, and opsonization of red blood cells by fragments of C3.

In yet another aspect, the present invention provides methods of increasing the proportion of PNH red blood cells which are able to survive complement attack, the method comprising administering an effective amount of a composition that inhibits activation of complement component C3 (C3), for example by inhibiting alternative pathway activation by initiation C3 convertase and/or by inhibiting formation and/or activity of amplifying C3 convertase, and opsonization of PNH red blood cells by fragments of C3.

In certain aspects of the present invention, in addition to inhibiting the complement alternative pathway, the composition may also inhibit one or more of the classical and lectin complement pathways. For example, complement receptor 1 (CR1), is expected to have inhibitory effects on all three of the complement pathways. While not directly an inhibitor of the complement alternative pathway, antibodies to MASP-1 may also be useful in the present invention. This is because removing MASP-1 from the system can reduce the amount of C3b that is produced via the classical and lectin pathways. With less C3b available, the amplification loop of the complement alternative pathway may be at least partially inhibited. Accordingly, for purposes of the present invention MAP1 and antibodies to MASP-1 are considered to be complement alternative pathway inhibitors that may be useful in certain embodiments of the invention. See, Skjodt et al., Molecular Immunology, 47:2229-30 (2010); and Petersen et al., Molecular Immunology 38:133-149 (2001).

In yet another aspect, the present invention provides methods of reducing or avoiding the occurrence of 'breakthrough' hemolytic crises in subjects who are treated for hemolysis using terminal complement inhibitors.

As preferred embodiments useful to accomplish the above methods, the present invention provides agents and compositions that inhibit the activity of the complement alternative pathway. Such agents and compositions may comprise fusion proteins comprising a complement receptor 2 (CR2) protein or biologically active fragment thereof; and modulator of complement activity which acts by modulating the presence of complement component C3 or its cleavage fragments, and/or C3 convertases, for example by inhibiting alternative pathway activation by initiation C3 convertase and/or by inhibiting formation and/or activity of amplifying C3 convertase, halting further progression of the complement cascade to form the membrane attack complex, and preventing or reducing the binding of such C3 molecules or fragments thereof to red blood cells, and in particular, preventing or reducing the opsonization of PNH red blood cells by fragments of C3.

In preferred embodiments, the inhibitor of the complement alternative pathway may comprise a fusion of the CR2 protein, or a fragment comprising at least the first two amino terminal short consensus repeat (SCR) domains of CR2, fused to factor H (FH) protein, or a biologically active fragment thereof. The biologically active fragment of FH protein may comprise at least the first four amino terminal SCR domains of FH. One such complement inhibitor is TT30 (SEQ ID NO:3), a fusion protein that comprises the first four amino-terminal short consensus repeat (SCR) domains of CR2 fused to the first five amino-terminal SCR domains of FH. Another such complement inhibitor comprises the first two amino terminal SCR domains of CR2 fused to the first four amino-terminal SCR domains of FH. The linkage can be at either end of the domains, such that the fusion protein may be described, proceeding from amino to carboxy termini, as either CR2-FH or FH-CR2.

In other preferred embodiments, the inhibitor of the complement alternative pathway may comprise a fusion of the CR2 protein, or a targeting fragment thereof comprising at least the first two amino terminal short consensus repeat (SCR) domains of CR2, fused to a complement inhibitor selected from the group consisting of Crry, DAF, MCP, complement factor I, compstatin or CR1, or biologically active fragments thereof. In other preferred embodiments, the inhibitory portion of the fusion protein may comprise an antibody to a factor selected from the group consisting of Factor B, Factor D or properdin; or an antigen-binding fragment thereof. As mentioned above, although not direct inhibitors of the complement alternative pathway, inhibitors of MASP-1 may effectively reduce the amount of C3b present, thereby at least partially inhibiting the amplification loop of the complement alternative pathway. Accordingly, inhibitos of MASP1 protein, such as antibodies to MASP1 and the endogenous MASP1 inhibitor MAP1 may be useful in certain embodiments of the present invention.

In a preferred embodiment, the inhibitor of the complement alternative pathway comprises a fusion of the CR2 protein, or a targeting fragment thereof comprising at least the first two amino terminal short consensus repeat (SCR) domains of CR2, fused to an antibody to Factor B within the third SCR domain and prevents formation of the C3bBb complex, or an antigen-binding fragment thereof. Suitable antibodies are described, for example, in Holers et al., US Patent Publication 2005/0260198 and in Emblen et al., US Patent Publication 2008/0299114. The disclosure of these documents is hereby specifically incorporated herein by reference. The linkage can be at either end of the domains, such that the fusion protein may be described, proceeding from amino to carboxy termini, as either CR2-complement inhibitor or complement inhibitor-CR2.

In additional embodiments, the inhibitor of the complement alternative pathway may comprise a fusion of a monoclonal antibody portion fused to a complement inhibitory portion. The monoclonal antibody portion comprises a monoclonal antibody, or a binding fragment thereof, which is directed toward complement component 3 (C3) or which will bind to the C3 fragment comprising one or more binding domains selected from the group consisting of C3b, iC3b, C3dg and C3d. The complement inhibitory portion comprises a complement inhibitor, or a biologically active fragment thereof, selected from the group consisting of Factor H protein, the group consisting of Crry, DAF, MCP, complement factor I, compstatin or CR1, or biologically active fragments thereof. In other preferred embodiments, the inhibitory portion of the fusion protein may comprise an antibody to a factor selected from the group consisting of Factor B, Factor D, MASP1, or the endogenous MASP1 inhibitor MAP1; or an antigen-binding fragment thereof. The linkage can be at either end of the domains, such that the fusion protein may be described, proceeding from amino to carboxy termini, as either antiC3-complement inhibitor or complement inhibitor-antiC3.

In further embodiments, the present invention comprises methods and materials for the treatment of subjects with a complement-mediated hemolytic disorder that affects red blood cells, such as PNH, wherein the method comprises administering to a subject afflicted with such disorder both a terminal complement inhibitor and an inhibitor of the complement alternative pathway. In this method, the complement inhibitors may be administered simultaneously or sequentially in either order. The terminal complement inhibitor may comprise an anti-C5 monoclonal antibody, such as eculizumab or pexelizumab, or another terminal complement inhibitor which inhibits C5 or other components of the Membrane Attack Complex (MAC), which comprises C6 through C9. For example, CD59, or TT33, which is a targeted CD59 fusion protein is useful as a terminal complement inhibitor. In certain embodiments, the inhibitor of the complement alternative pathway may inhibit the activity of the complement alternative pathway, wherein the composition inhibits activation of complement component C3 (C3), C3 fragments and/or C3 convertases, for example by inhibiting alternative pathway activation by initiation C3 convertase and/or by inhibiting formation and/or activity of amplifying C3 convertase, and opsonization of PNH red blood cells by fragments of C3. In other embodiments, the inhibitor of the complement alternative pathway may additionally inhibit other complement pathways, such as the classical and lectin mediated pathways.

In another aspect, the present invention provides compositions for the treatment of PNH, or of other diseases which involve a complement-mediated extravascular hemolysis component, which compositions comprise a combination of:
a) a terminal complement inhibitor; and
b) an inhibitor of the complement alternative pathway.

The terminal complement inhibitor may preferably comprise an anti-C5 antibody, such as eculizumab or pexelizumab. The inhibitor of the complement alternative pathway may preferably comprise fusion proteins comprising a complement receptor 2 (CR2) protein or biologically active fragment thereof; and modulator of complement activity which acts by modulating the presence of complement component C3, its cleavage fragments and/or C3 convertases and preventing or reducing the binding of such C3 molecules or fragments thereof to red blood cells, and in particular, preventing or reducing the opsonization of red blood cells by fragments of C3. In particularly preferred embodiments, the inhibitor of the complement alternative pathway may comprise a fusion of the CR2 protein, or a fragment comprising at least the first two amino terminal SCR domains of CR2, fused to factor H protein, or a biologically active fragment of FH. One such complement alternative inhibitor comprises a CR2 targeting domain portion fused to a complement inhibitory portion of factor H comprising the first four N-terminal SCR domains of human Factor H. In a particular preferred embodiment, the inhibitor of the complement alternative pathway is TT30 (SEQ ID NO:3), which comprises the first four N-terminal SCR domains of CR2 fused to the first five N-terminal SCR domains of FH. In another preferred embodiment, the inhibitor of the complement alternative pathway is TT31, which comprises the first four N-terminal SCR domains of CR2 fused to two copies of the first five N-terminal SCR domains of FH.

In other preferred embodiments, the inhibitor of the complement alternative pathway may comprise the CR2 protein, or a fragment comprising at least the first two amino terminal short consensus repeat (SCR) domains of CR2, fused to a complement inhibitory portion selected from the group consisting of Anti-Factor B antibody, Anti-Properdin antibody, Anti-Factor D antibody, Factor I protein, compstatin, Crry, DAF, MCP or CR1, or biologically active fragments thereof. One such preferred embodiment is TT32, which comprises the first four SCR domains of CR2 fused to the first ten SCR domains of CR1. Because of CR1's ability to inhibit not only the complement alternative pathway, but also the classical and lectin mediated complement pathways, inhibitors such as TT32 may find more wide-ranging use in other disease states which involve both an intravascular and extravascular component of hemolysis, as well as in autoimmune diseases and related conditions.

In other preferred embodiments, the inhibitor of the complement alternative pathway may comprise a fusion of a monoclonal antibody portion fused to a complement inhibitory portion. The monoclonal antibody portion comprises a monoclonal antibody, or a binding fragment thereof, which is directed toward complement component 3 (C3) or which will bind to the C3 fragment comprising one or more binding domains selected from the group consisting of C3b, iC3b, C3dg and C3d. The complement inhibitory portion comprises a complement inhibitor, or a biologically active fragment thereof, selected from the group consisting of Factor H protein, Anti-Factor B antibody, Anti-Properdin antibody, Anti-Factor D antibody, Factor I protein, compstatin, Anti-MASP1 antibody, anti-MAP1 antibody, Crry, DAF, MCP or CR1, or biologically active fragments thereof. In preferred embodiments, the complement inhibitory portion comprises (a) the first four SCR domains of human Factor H protein; (b) the first five N-terminal SCR domains of Crry; or (c) the first ten SCR domains of CR1; or; (d) MCP, comprising the first three N-terminal SCR domains; soluble DAF, comprising SCR domains 2-4, with or without the serine-threonine rich region, but without the glycophosphatidyl anchor.

The present invention provides in one aspect a method of treating a subject having a complement-mediated hemolytic disorder affecting blood cells, the method comprising administering an effective amount of a composition that inhibits activation of the complement alternative pathway, wherein the composition inhibits activation of complement component C3 (C3) and opsonization of red blood cells by fragments of C3.

In another aspect provided herein is a method of treating complement-mediated hemolysis in a subject, the method comprising administering an effective amount of a composition that inhibits activation of the complement alternative pathway, wherein the composition maintains normal serum levels of lactate dehydrogenase and hemoglobin.

In certain embodiments in any of the methods described herein, the composition selectively inhibits the complement alternative pathway. In certain embodiments in any of the methods described herein, the composition that inhibits the activity of the complement alternative pathway comprises a fusion protein comprising a complement receptor 2 (CR2) protein or biologically active fragment thereof; and a factor H (fH) protein or biologically active fragment thereof. In certain embodiments in any of the methods described herein, the fusion protein comprises the first four amino-terminal short consensus repeat (SCR) domains of CR2 fused to the first five amino-terminal SCR domains of fH.

In certain embodiments in any of the methods described herein, the method further comprises administering a terminal complement inhibitor to the subject. In certain embodiments in any of the methods described herein, the terminal complement inhibitor inhibits cleavage of complement protein C5 (C5). In certain embodiments in any of the methods described herein, the terminal complement inhibitor is a humanized anti-C5 antibody or antigen-binding fragment thereof. In certain embodiments in any of the methods described herein, the terminal complement inhibitor is eculizumab.

In certain embodiments in any of the methods described herein, the subject has paroxysmal nocturnal hemoglobinuria (PNH) and the subject's red blood cells are opsonized by fragments of C3 in the absence of the composition. In certain embodiments in any of the methods described herein, the subject has previously been treated with a terminal complement inhibitor. In certain embodiments in any of the methods described herein, the subject was not responsive, partially responsive, or has progressed on the treatment of the terminal complement inhibitor.

In certain embodiments of any of the methods described herein, the subject has one or more of the following characteristics:
a. the subject exhibits signs or symptoms continued loss of red blood cells by ongoing or intermittent intravascular hemolysis and/or extravascular hemolysis;
b. the subject has red blood cells opsonized by fragments of C3;
c. the subject requires periodic blood transfusions;
d. the subject has low normal or below normal levels of hemoglobin;
e. the subject has low normal or below normal levels of platelets;
f. the subject has high normal or above normal reticulocytes;
g. the subject has high normal or above normal bilirubin; or
h. the subject has iron overload or is at risk of iron overload, wherein the method comprising administering an effective amount of a composition that inhibits the activity of the complement alternative pathway.

In certain embodiments of any of the methods described herein, the subject requires periodic blood transfusions. In certain embodiments of any of the methods described herein, the subject is thereby rendered transfusion independent. In certain embodiments of any of the methods described herein, the subject has below normal levels of hemoglobin.

In certain embodiments of any of the methods described herein, the composition increases the survival of red blood cells in the subject. In certain embodiments of any of the methods described herein, the complement-mediated hemolytic disorder is sickle cell anemia.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

The term "subject" refers to a mammal, including humans. A subject includes, but is not limited to, human, bovine, horse, feline, canine, rodent, or primate.

BRIEF DESCRIPTION OF THE FIGURES

FIG. 1a illustrates the result for normal control subjects; FIG. 1b illustrates the result for subjects with cold agglutinin disease (CAD); FIG. 1c illustrates the results for PNH subjects who have not been treated with a terminal complement inhibitor; FIG. 1d illustrates the results for two PNH subjects who have been treated with the terminal complement inhibitor eculizumab, an antibody to C5.

FIG. 2a illustrates the result for normal control subjects; FIG. 2b illustrates the result for subjects with cold agglutinin disease (CAD); FIG. 2c illustrates the results for PNH subjects who have not been treated with a terminal complement inhibitor; FIG. 2d illustrates the results for four PNH subjects who have previously been treated with the terminal complement inhibitor eculizumab (Ecu), an antibody to C5.

FIG. 5 illustrates the kinetics of C3 binding on PNH RBCs. FIG. 5a illustrates the appearance of C3 binding after treatment with eculizumab. It can be noted that C3 binding appears a few weeks after starting anti-C5 antibody treatment. FIG. 5b illustrates the binding of C3 over long term (two years). It can be noted that C3 binding remains very stable over this time period.

(FIG. 17b): AcS+3000 nM TT30. Cells were characterized for lysis (red) and survival; surviving cells were further characterized for C3-coating: C3-positive (yellow) and C3-negative (green).

(FIG. 18b): AcS+3000 nM TT30. Cells were characterized for lysis (red) and survival; surviving cells were further characterized for C3-coating: C3-positive (yellow) and C3-negative (green).

(FIG. 19b): AcS+3000 nM TT30. Cells were characterized for lysis (red) and survival; surviving cells were further characterized for C3-coating: C3-positive (yellow) and C3-negative (green).

FIG. 33 shows the predicted amino acid sequence of TT30 (SEQ ID NO:3). Each SCR is in a separate line. SCRs from CR2 and Factor H are defined and connecting sequences between SCRs are underlined. Consensus glycosylation sites are Asn101, Asn107, and Asn454.

DETAILED DESCRIPTION OF THE INVENTION

Figure 1:
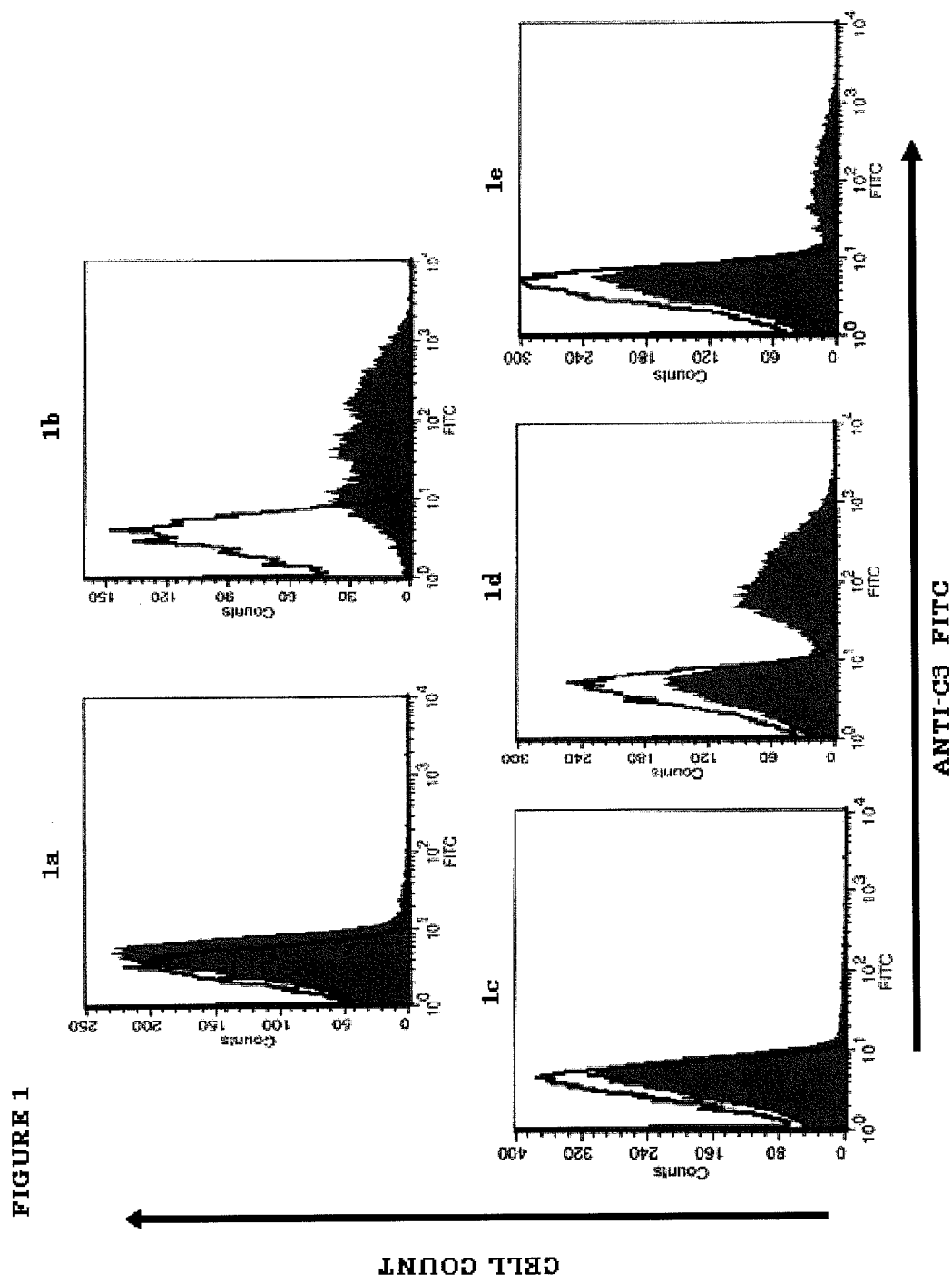
FIG. 1 illustrates the results of single color flow cytometry in measuring C3 binding on red blood cells in PNH subjects. Along the Y axis are plotted the red blood cell counts; along the X axis are plotted Anti-C3 fluorescent isothiocyanate (FITC) counts.

The present application relates to treatment of complement-mediated hemolytic disorders such as paroxysmal nocturnal hemoglobinuria (PNH). The application is based on the finding that modulation of the complement alternative pathway (CAP), specifically, with a targeted construct comprising CR2 and factor H (TT30; SEQ ID NO:3), is more effective than inhibition with a terminal complement inhibitor, namely, an anti-C5 antibody (eculizumab), at preventing hemolysis of PNH red blood cells (RBCs). Without being bound by a theory, it is hypothesized that the in vitro hemolysis of RBCs from PNH patients on anti-C5 antibody despite the presence of protective concentrations of the antibody may be related to increased susceptibility to lysis of C3 fragment coated RBCs.

Accordingly, the application in one aspect provides a method of treating a complement-mediated hemolytic disorders (such as hemolytic disorder affecting red blood cells for example PNH) in a subject, particularly in a subject who has hemolytic anemia, or who exhibits one or more of the following: symptoms of residual anemia and/or complement-mediated extravascular hemolysis and/or incomplete control of intravascular hemolysis. These features are referred to herein collectively as "hemolytic markers." In another aspect, there is provided a method of treating a complement-mediated hemolytic disorder (such as hemolytic disorder affecting red blood cells for example PNH) in a subject, wherein the subject has previously been treated with a terminal complement inhibitor (such as an anti-C5 antibody). The methods are carried out by administering an effective amount of a composition that inhibits (such as selectively inhibits) activation of the complement alternative pathway. Particularly suitable complement activation pathway inhibitors are targeted constructs (such as targeted constructs described herein) that comprise a targeting moiety which directs the construct to a site of complement activation and an active moiety which has complement inhibitory activity. In another aspect, there is provided a method of treating a complement-mediated hemolytic disorder (such as hemolytic disorder affecting red blood cells for example PNH) in a subject, comprising administering to the subject: a) an effective amount of a terminal complement inhibitor (such as an anti-C5 antibody) and b) an effective amount of a composition that inhibits (such as selectively inhibits) activation of the complement alternative pathway. "Terminal complement inhibitor" refers to an inhibitor of one or more complement pathways that inhibits the activity of a component that is downstream of the C3 convertase. These include, for example, inhibitor of the C3 convertase, blocking of C5 (for example an anti-C5 antibody), or an inhibitor that blocks the MAC (membrane attack complex) formation.

Accordingly, in some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has hemolytic anemia or exhibits one or more of the following: symptoms of residual anemia and/or complement-mediated extravascular hemolysis and/or incomplete control of intravascular hemolysis. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject exhibits signs or symptoms of continued loss of red blood cells by ongoing or intermittent intravascular hemolysis and/or extravascular hemolysis. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has red blood cells opsonized by fragments of C3. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject requires periodic blood transfusions. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has low normal or below normal levels of hemoglobin. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has low normal or below normal levels of platelets. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has high normal or above normal reticulocytes. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has high normal or above normal bilirubin. In some embodiments, there is provided a method of treating a complement-mediated hemolytic disorders (such as hemolytic disorder affecting red blood cells for example PNH) in a subject, comprising administering to the subject an effective amount of a composition that inhibits (such as selectively inhibits) activation of the complement alternative pathway, wherein the subject has iron overload or is at risk of iron overload. In some embodiments, the composition inhibits activation of complement component C3 (C3) and opsonization of red blood cells by fragments of C3. In some embodiments, the composition maintains normal serum levels of lactate dehydrogenase and hemoglobin. In some embodiments, the complement activation pathway inhibitors is a targeted construct (such as targeted constructs described herein) that comprise a targeting moiety which directs the construct to a site of complement activation and an active moiety which has complement inhibitory activity. In some embodiments, the targeted construct comprises a CR2 or a fragment thereof and a factor H or a fragment thereof. In some embodiments, the targeted construct comprises the first four SCR domains of CR2 and the first five SCR domains of factor H (such as TT30). In some embodiments, the targeted construct is selected from TT30, TT31, and TT32.

In some embodiments, there is provided a method of treating a complement-mediated hemolytic disorder (such as hemolytic disorder affecting red blood cells for example PNH) in a subject, comprising administering to the subject an effective amount of a composition that inhibits (such as selectively inhibits) activation of the complement alternative pathway, wherein the subject has previously been treated with a terminal complement inhibitor (such as an anti-C5 antibody). In some embodiments, the subject is non-responsive to the treatment of a terminal complement inhibitor (such as an anti-C5 antibody). In some embodiments, the subject is partially responsive to the treatment of a terminal complement inhibitor (such as an anti-C5 antibody). In some embodiments, the subject is initially responsive to the terminal complement inhibitor (such as an anti-C5 antibody) but becomes non-responsive after a certain period (such as a month, two months, three months, four months, six months) of treatment with the anti-C5 antibody. In some embodiments, the individual exhibits one or more of the hemolytic markers discussed above upon treatment with the terminal complement inhibitor (such as anti-C5 antibody). In some embodiments, the composition inhibits activation of complement component C3 (C3) and opsonization of red blood cells by fragments of C3. In some embodiments, the composition maintains normal serum levels of lactate dehydrogenase and hemoglobin. In some embodiments, the complement activation pathway inhibitors is a targeted construct (such as targeted constructs described herein) that comprise a targeting moiety which directs the construct to a site of complement activation and an active moiety which has complement inhibitory activity. In some embodiments, the targeted construct comprises a CR2 or a fragment thereof and a factor H or a fragment thereof. In some embodiments, the targeted construct comprises the first four SCR domains of CR2 and the first five SCR domains of factor H (such as TT30). In some embodiments, the targeted construct is selected from TT30, TT31, and TT32. In some embodiments, the subject was terminated with the treatment of the terminal complement inhibitor for at least 1, 2, 3, 4, 5, 6, 7, 8, 9, or 10 weeks prior to the treatment with the inhibitor of the alternative complement pathway.

In some embodiments, there is provided a method of treating a complement-mediated hemolytic disorder (such as hemolytic disorder affecting red blood cells for example PNH) in a subject, comprising administering to the subject: a) an effective amount of a terminal complement inhibitor (such as an anti-C5 antibody) and b) an effective amount of a composition that inhibits (such as selectively inhibits) activation of the complement alternative pathway. In some embodiments, there is provided a method of treating a complement-mediated hemolytic disorder (such as hemolytic disorder affecting red blood cells for example PNH) in a subject, comprising administering to the subject: a) an effective amount of an anti-C5 antibody (such as eculizumab) and b) an effective amount of a composition that inhibits (such as selectively inhibits) activation of the complement alternative pathway. In some embodiments, there is provided a method of treating a complement-mediated hemolytic disorder (such as hemolytic disorder affecting red blood cells for example PNH) in a subject, comprising administering to the subject: a) an effective amount of an inhibitor that prevents the formation of the MAC (such as CD59) and b) an effective amount of a composition that inhibits (such as selectively inhibits) activation of the complement alternative pathway. In some embodiments, the composition inhibits activation of complement component C3 (C3) and opsonization of red blood cells by fragments of C3. In some embodiments, the composition maintains normal serum levels of lactate dehydrogenase and hemoglobin. In some embodiments, the complement activation pathway inhibitors is a targeted construct (such as targeted constructs described herein) that comprise a targeting moiety which directs the construct to a site of complement activation and an active moiety which has complement inhibitory activity. In some embodiments, the targeted construct comprises a CR2 or a fragment thereof and a factor H or a fragment thereof. In some embodiments, the targeted construct comprises the first four SCR domains of CR2 and the first five SCR domains of factor H (such as TT30). In some embodiments, the targeted construct is selected from TT30, TT31, and TT32. TT30 comprises a complement alternative pathway inhibitory portion of Factor H protein, which is targeted to sites of complement activation and inflammation through fusion with a portion of the complement receptor 2 protein (CR2 or CD21) which is known to bind to tissue/cell-fixed fragments of the complement component 3 (C3). TT31 is similar to TT30, but contains an additional copy of the complement alternative pathway inhibitory portion of Factor H protein. TT32 comprises a complement inhibitory portion of complement receptor 1 (CR1), targeted through fusion with the same portion of the CR2 protein. CR1 is known to be a broader inhibitor of complement than is Factor H. TT32 will therefore inhibit not only the complement alternative pathway, but will locally inhibit both the classic and lectin pathways of complement as well. Other suitable targeted inhibitors are described in Gilkeson et al., US Patent Publication 2008/0221011, the disclosure of which is hereby specifically incorporated herein by reference.

The present invention provides methods and compositions for the treatment of subjects having any of a number of complement-mediated disease states which affect red blood cells. Among these are subjects having paroxysmal nocturnal hemoglobinuria (PNH), atypical hemolytic uremic syndrome (aHUS); chronic hemolytic anemia; antibody-mediated autoimmune hemolytic anemia; anemia caused by hemoglobinopathies such as sickle cell disease; anemia caused by infection such as malaria; anemia due to transfusion reaction; and cold agglutinin disease (CAD). In particular embodiments, the present invention provides methods and compositions for the treatment of subjects with hemolytic anemia, which may be caused by the above disease states, or who exhibit at least one characteristic, which characteristics may be symptoms of residual anemia and/or complement-mediated extravascular hemolysis and/or incomplete control of intravascular hemolysis:

a. the subject exhibits signs or symptoms continued loss of red blood cells by ongoing or intermittent intravascular hemolysis and/or extravascular hemolysis;

b. the subject has red blood cells opsonized by fragments of C3;

c. the subject requires periodic blood transfusions;

d. the subject has low normal or below normal levels of hemoglobin;
e. the subject has low normal or below normal levels of platelets;
f. the subject has high normal or above normal reticulocytes;
g. the subject has high normal or above normal bilirubin; or
h. the subject has iron overload or is at risk of iron overload.

The indications discussed above (also referred to as "hemolytic markers") can also be used to assess responsiveness to treatment, predict responsiveness to treatment, monitoring progress of treatment, determining suitability of the subject for treatment, determining non-suitability of the subject for treatment, selecting subject for treatment, and/or selecting subject for continued treatment. Thus, for example, in some embodiments, there is provided a method for assessing responsiveness, identifying subjects, and/or selecting subjects having paroxysmal nocturnal hemoglobinuria (PNH) or other complement-mediated hemolytic disorder affecting red blood cells for treatment comprising administering an effective amount of a composition that inhibits the activity of the complement alternative pathway.

In some embodiments, there is provided a method of assessing whether a subject having paroxysmal nocturnal hemoglobinuria (PNH) or other complement-mediated hemolytic disorder affecting red blood cells will likely respond to treatment comprising administering an effective amount of a composition that inhibits the activity of the complement alternative pathway, the method comprising assessing at least one hemolytic markers described herein, wherein presence of one or more of these characteristics indicate that the subject will likely be responsive to the treatment. In some embodiments, the method further comprises administering the effective amount of a composition that inhibits the activity of the complement alternative pathway to the subject who is likely to respond to the treatment.

In some embodiments, there is provided a method of identifying a subject suitable for treatment comprising administering an effective amount of a composition that inhibits the activity of the complement alternative pathway, wherein the subject has paroxysmal nocturnal hemoglobinuria (PNH) or other complement-mediated hemolytic disorder affecting red blood cells, the method comprising assessing at least one hemolytic markers described herein, wherein the presence of one or more of these characteristics identify the subject for being suitable for treatment. In some embodiments, the method further comprises administering the effective amount of a composition that inhibits the activity of the complement alternative pathway to the subject who may be suitable for treatment.

A subject who "may be suitable", which includes a subject who "is suitable" for treatment(s) described herein, is a subject who is more likely than not to benefit from administration of said treatments. Conversely, a subject who "may not be suitable" or "may be unsuitable", which includes a subject who is "unsuitable" for treatment(s) described herein, is a subject who is more likely than not to fail to benefit from administration of said treatments.

In addition, methods are provided herein of selecting or not selecting a subject with paroxysmal nocturnal hemoglobinuria (PNH) or other complement-mediated hemolytic disorder affecting red blood cells more likely suitable or less likely suitable for treatment comprising administering an effective amount of a composition that inhibits the activity of the complement alternative pathway, the method comprising (A) assessing at least one hemolytic markers described herein; and (B) selecting the subject having one or more of these characteristics. In some embodiments, the method further comprises administering the effective amount of a composition that inhibits the activity of the complement alternative pathway to the subject who may be suitable for treatment.

Provided herein are also methods for marketing a therapy described herein comprising informing a target audience about the use of the compositions described herein for such uses.

The present invention also provides methods of monitoring responsiveness of a subject with paroxysmal nocturnal hemoglobinuria (PNH) or other complement-mediated hemolytic disorder affecting red blood cells to treatment comprising administering an effective amount of a composition that inhibits the activity of the complement alternative pathway, the method comprising assessing at least one hemolytic marker described herein.

In certain embodiments, the subject has paroxysmal nocturnal hemoglobinuria (PNH). PNH is a consequence of clonal expansion of one or more hematopoietic stem cells with mutant PIG-A. The extent to which the PIG-A mutant clone expands varies widely among patients. In some embodiments, more than 90% of peripheral blood cells in the subject are GPI-AP deficient. In certain embodiments, more than any one of 80%, 70%, 60%, 50%, 40%, 30%, 20% or 10% of peripheral blood cells in the subject are GPI-AP deficient. In certain embodiments, less than 10% of peripheral blood cells in the subject are GPI-AP deficient. Another feature of PNH is its phenotypic mosaicism based on the PIG-A genotype that determines the degree of GPI-AP deficiency. For example, PNH III cells are completely deficient in GPI-APs, PNH II cells are partially (~90%) deficient, and PNH I cells, which are progeny of residual normal stem cells, express GPI-AP at normal density. In certain embodiments, the subject has only type I and type III cells. In certain embodiments, the subject has type I, type II, and type III cells. In certain embodiments, the subject has type I and type II cells.

In certain embodiments, the subject has classic PNH. Classic PNH is characterized by a large population of GPI-AP deficient PMNs, cellular marrow with erythorid hyperplasia and normal or near-normal morphology and frequent or persistent florid macroscopic hemoglobinuria. In certain embodiments, the subject has PNH in the setting of another bone marrow failure syndrome. PNH in the setting of another bone marrow failure is characterized by a relatively small percentage (<30%) of GPI-AP deficient PMNs, evidence of a concomitant bone marrow failure syndrome and intermittent or absent mild to moderate macroscopic hemoglobinuria. In certain embodiments, the subject has subclinical PNH. Subclinical or latent PNH is characterized by a small (<1%) population of GPI-AP deficient PMNs, evidence of a concomitant bone marrow failure syndrome and no clinical or biochemical evidence of intravascular hemolysis.

In certain embodiments, the subject has atypical hemolytic uremic syndrome (aHUS). In certain embodiments, the subject has chronic hemolytic anemia. In some embodiments, the subject has cold agglutinin disease (CAD). In certain embodiments, the subject exhibits signs or symptoms continued loss of red blood cells by ongoing or intermittent intravascular hemolysis and/or extravascular hemolysis. In certain embodiments, the subject has PNH red blood cells opsonized by fragments of C3. In certain embodiments, subject requires periodic blood transfusions. In some embodiments, the subject has any one of the following:

paroxysmal nocturnal hemoglobinuria (PNH), atypical hemolytic uremic syndrome (aHUS); chronic hemolytic anemia; antibody-mediated autoimmune hemolytic anemia; anemia caused by hemoglobinopathies such as sickle cell disease; anemia caused by infection such as malaria; anemia due to transfusion reaction; and cold agglutinin disease (CAD).

The methods described herein are also useful for treating complement-mediated hemolysis, reducing intravascular hemolysis, reducing extravascular hemolysis, and increasing survival of red blood cells in a subject.

In a particular embodiment of the present invention, the subject exhibits iron overload. Transfusions and other treatment of anemia may contribute to or exacerbate iron overload. In addition, treatment of PNH with a terminal complement inhibitor such as eculizumab or pexelizumab or another terminal complement inhibitor which inhibits C5 or other components of the Membrane Attack Complex (MAC), which comprises C6 through C9, leads to the accumulation of C3 fragments on the surface of PNH RBC, as well as subsequent EVH and iron accumulation by the liver. Accordingly, a subject having PNH or another complement-mediated red blood cell disorder who exhibits symptoms of iron overload or who is approaching iron overload may not be optimally treated by further transfusions. In such cases, treatment in accordance with the methods and compositions of the present invention may be especially beneficial in reducing or controlling anemia without contributing to or exacerbating iron overload. Alternatively, treatment in accordance with the methods and compositions of the present invention may be especially beneficial in treating subjects having complement-mediated hemolytic disorders, such as PNH, while preventing the iron overload that can be observed with treatment with a terminal complement inhibitor, or preventing iron overload and thus allowing for continued administration of the terminal complement inhibitor.

For purposes of the present invention, a subject is considered to be suffering from iron overload if their serum iron levels are in excess of about 350 ug/dL (mild iron toxicity); preferably in excess of about 500 ug/dL (serious iron toxicity). A subject is considered to be at risk of iron overload if their serum iron levels are high normal or above normal ranges. Normal iron range is considered to be from about 40 to about 220 ug/dL; and more preferably approximately from 50 to about 160 ug/dL for adult males. Normal iron ranges for adult females are approximately 5 to 10 percent lower than that for adult males. 'High normal' iron concentration is considered to be in the upper quarter (25%) of the normal range; preferably in the upper tenth (10%) of the normal range. See, Jacobs & DeMott, Laboratory Test Handbook, $5^{th}$ ed., (LexiComp Inc, Hudson, Ohio)(2001) at p. 203-205). As is known to one skilled in the art, 'normal ranges' of iron and iron binding capacity can vary depending upon the specific laboratory and test.

In some embodiments, the serum iron level of an adult male subject is higher than about 220 ug/dL. In some embodiments, the serum iron level of an adult male subject is higher than about 160 ug/dL. In some embodiments, the serum iron level of an adult male subject is between about 175 ug/dL and about 220 ug/dL. In some embodiments, the serum iron level of an adult male subject is between about 130 ug/dL and about 160 ug/dL. In some embodiments, the serum iron level of an adult male subject is between about 200 ug/dL and about 220 ug/dL. In some embodiments, the serum iron level of an adult male subject is between about 150 ug/dL and about 160 ug/dL. In some embodiments, the serum iron level of an adult female subject is higher than about 200 ug/dL. In some embodiments, the serum iron level of an adult female subject is higher than about 145 ug/dL. In some embodiments, the serum iron level of an adult female subject is between about 160 ug/dL and about 200 ug/dL. In some embodiments, the serum iron level of an adult female subject is between about 120 ug/dL and about 145 ug/dL. In some embodiments, the serum iron level of an adult female subject is between about 185 ug/dL and about 200 ug/dL. In some embodiments, the serum iron level of an adult female subject is between about 135 ug/dL and about 145 ug/dL.

In addition, the methods and compositions of the present invention may be useful for the treatment of other disorders involving complement-mediated extravascular hemolysis, and complement-related disorders which involve one or more of the above characteristics. These disorders may be characterized by high serum lactate dehydrogenase (LDH) levels and/or low serum hemoglobin (HgB) levels. Such disorders may include, for example, atypical hemolytic uremic syndrome (aHUS); chronic hemolytic anemia; and cold agglutinin disease (CAD). Jacobson et al., American J. Medicine, 54:514-21 (1973).

Because terminal complement inhibitors such as eculizumab, which is a monoclonal antibody that binds C5, must competitively bind to C5 and prevent the enzymatic cleavage of C5 by C5 convertase, it may be difficult, if not impossible, for terminal complement inhibitors to treat a subject experiencing red blood cell lysis to effectively achieve and stably maintain normal ranges of such markers of hemolytic lysis, such as LDH and HgB, with reduced risk of occurrence of breakthrough hemolytic lysis. The effect of such inhibitors depends upon the ability of the antibody to C5 to completely block the cleavage of C5 by C5 convertase. However, because antibodies typically achieve an equilibrium level of binding with their antigen, in this case C5, there will periodically or intermittently be some level unbound C5 present in the blood and at the red blood cell surface. Unbound C5 may be irreversibly cleaved by C5 convertase present on the red blood cells. The amount of unbound C5 present will increase if either (a) serum inhibitor concentration is reduced; or (b) serum C5 concentration in the blood is increased. Further, because the terminal complement inhibitor competes with C5 convertase, a natural ligand for C5, which will irreversibly cleave C5, the effectiveness of the terminal complement inhibitor in maintaining control of hemolysis and preventing breakthrough is affected by increases in serum concentrations of C5 convertase. As noted previously, the accumulation of C3 fragments and C3 convertase in the blood serum of subjects who are receiving terminal complement inhibitors will naturally tend to increase the serum levels of C5 convertase, limiting the efficacy of the inhibitor.

LDH and HgB:

With the targeted inhibitors of the present invention, the above situations leading to 'breakthrough' lysis may be reduced or avoided because the targeted inhibitors are tethered to C3d fragments, on the red blood cell surface, while the complement inhibitor end of the fusion protein is able to act locally at the red blood cell surface to inhibit activation of the complement alternative pathway. Accordingly, a more stable inhibition of complement may be achieved. Thus, in certain embodiments of the present invention, it is anticipated that a subject suffering from PNH, aHUS, CAD or other hemolytic anemia may be effectively treated such that serum concentration levels of lactate dehydrogenase (LDH) and hemoglobin (HgB) may be maintained within normal concentration ranges. In general, LDH in the serum is an indication of red blood cell lysis, and high levels are an indication for hemolysis. See, Kato et al., Blood, 107:2279-85 (2006). HgB is a measurement of hemoglobin in the serum, and low levels are an indicator for anemia. See Crosby and Ackroyd, Am. J. Medicine, 13:273-83 (1952); Dameshek, Am. J. Medicine, 18:315-25 (1955).

The presence of hemolytic anemias may be indicated by high serum levels of LDH concomitant with low serum levels of HgB. For purposes of the present invention, the 'normal range' of LDH serum concentration is considered to be up to approximately 350 IU/l; preferably from about 105 to 333 IU/l; preferably from approximately 140 to 280 IU/L; and in other embodiments, up to about 190 U/L. 'High normal' LDH concentrations would be the upper half (50%) of the normal range, preferably the upper quarter (25%) of the normal range, and most preferably, the upper tenth (10%) of the normal range. For purposes of the present invention, the 'normal range' of serum HgB concentration is considered to be within the range of approximately 13.5 to 18.0 gm/dL for adult males; preferably from about 13.8 to 18.0; and more preferably from about 14.0 to about 17.0 for males; and approximately 11.0 to 16.2 gm/dL for females; more preferably about 12.0 to 16.0 gm/dL for adult females. 'Low normal' HgB concentrations would be the lower half (50%) of the normal range, preferably the lower quarter (25%) of the normal range, and most preferably, the lower tenth (10%) of the normal range. As is known to one skilled in the art, 'normal ranges' of LDH and HgB can vary depending upon the specific laboratory and test. [See, WorldWideWeb at nlm.nih.gov; Jacobs & DeMott, Laboratory Test Handbook, 5$^{th}$ ed., (LexiComp Inc, Hudson, Ohio) (2001) at p. 206-208; 319-422].

In certain embodiments, the subject has low normal or below normal levels of hemoglobin. In some embodiments, the hemoglobin levels are below about 13.5 gm/dL in an adult male subject. In some embodiments, the hemoglobin levels are below about 13.8 gm/dL in an adult male subject. n some embodiments, the hemoglobin levels are below about 14 gm/dL in an adult male subject. In some embodiments, the hemoglobin levels are between about 13.5 gm/dL and about 15.75 gm/dL in an adult male subject. In some embodiments, the hemoglobin levels are between about 13.5 gm/dL and about 14.6 gm/dL in an adult male subject. In some embodiments, the hemoglobin levels are between about 13.5 gm/dL and about 13.9 gm/dL in an adult male subject. In some embodiments, the hemoglobin levels are between about 13.8 gm/dL and about 15.9 gm/dL in an adult male subject. In some embodiments, the hemoglobin levels are between about 13.8 gm/dL and about 14.9 gm/dL in an adult male subject. In some embodiments, the hemoglobin levels are between about 13.8 gm/dL and about 14.2 gm/dL in an adult male subject. In some embodiments, the hemoglobin levels are between about 14 gm/dL and about 15.5 gm/dL in an adult male subject. In some embodiments, the hemoglobin levels are between about 14 gm/dL and about 14.75 gm/dL in an adult male subject. In some embodiments, the hemoglobin levels are between about 14 gm/dL and about 14.3 gm/dL in an adult male subject.

In some embodiments, the hemoglobin levels are below about 11.0 gm/dL in an adult female subject. In some embodiments, the hemoglobin levels are below about 12.0 gm/dL in an adult female subject. In some embodiments, the hemoglobin levels are between about 11.0 gm/dL and about 13.6 gm/dL in an adult female subject. In some embodiments, the hemoglobin levels are between about 11.0 gm/dL and about 12.3 gm/dL in an adult female subject. In some embodiments, the hemoglobin levels are between about 11.0 gm/dL and about 11.5 gm/dL in an adult female. In some embodiments, the hemoglobin levels are between about 12.0 gm/dL and about 14.0 gm/dL in an adult female subject. In some embodiments, the hemoglobin levels are between about 12.0 gm/dL and about 13.0 gm/dL in an adult female subject. In some embodiments, the hemoglobin levels are between about 12.0 gm/dL and about 12.2 gm/dL in an adult female subject.

In some embodiments, the subject further has LDH levels higher than about 350 IU/l. In some embodiments, the subject further has LDH levels higher than about 280 IU/l. In some embodiments, the subject further has LDH levels between about 219 IU/l and 333 IU/l. In some embodiments, the subject further has LDH levels between about 276 IU/l and 333 IU/l. In some embodiments, the subject further has LDH levels between about 310 IU/l and 333 IU/l. In some embodiments, the subject further has LDH levels between about 210 IU/1 and 280 IU/l. In some embodiments, the subject further has LDH levels between about 245 IU/l and 280 IU/l. In some embodiments, the subject further has LDH levels between about 266 IU/l and 280 IU/1.

Platelets:

Another characteristic that may be indicative of hemolytic anemia is a serum platelet level below normal range. For purposes of the present invention, the 'normal range' of serum platelet concentration is considered to be within the range of approximately 130 to about 410 ($\times 10^9$/L); preferably within the range of approximately 150 to about 400 ($\times 10^9$/L); and more preferably from about 210 to about 330 ($\times 10^9$/L) for adult males. For adult females, the 'normal range' of serum platelet concentration may be considered to be about 5 to 10% higher than for adult males. 'Low normal' platelet concentrations would be the lower half (50%) of the normal range, preferably the lower quarter (25%) of the normal range, and most preferably, the lower tenth (10%) of the normal range. [See, WorldWideWeb at nlm.nih.gov and at questdiagnostics.com; Jacobs & DeMott, Laboratory Test Handbook, 5$^{th}$ ed., (LexiComp Inc, Hudson, Ohio)(2001) at p. 471-472]. As is known to one skilled in the art, 'normal ranges' of platelets can vary depending upon the specific laboratory and test.

In certain embodiments, the subject has low normal or below normal levels of platelets. In some embodiments, the serum platelet level is below about 130 ($\times 10^9$/L) in an adult male subject. In some embodiments, the serum platelet level is below about 150 ($\times 10^9$/L) in an adult male subject. In some embodiments, the serum platelet level is below about 210 ($\times 10^9$/L) in an adult male subject. In some embodiments, the serum platelet level is between about 130 ($\times 10^9$/L) and about 270 ($\times 10^9$/L) in an adult male subject. In some embodiments, the serum platelet level is between about 130 ($\times 10^9$/L) and about 200 ($\times 10^9$/L) in an adult male subject. In some embodiments, the serum platelet level is between about 130 ($\times 10^9$/L) and about 158 ($\times 10^9$/L) in an adult male subject. In some embodiments, the serum platelet level is between about 150 ($\times 10^9$/L) and about 275 ($\times 10^9$/L) in an adult male subject. In some embodiments, the serum platelet level is between about 150 ($\times 10^9$/L) and about 112.5 ($\times 10^9$/L) in an adult male subject. In some embodiments, the serum platelet level is between about 150 ($\times 10^9$/L) and about 175 ($\times 10^9$/L) in an adult male subject. In some embodiments, the serum platelet level is between about 210 ($\times 10^9$/L) and about 260 ($\times 10^9$/L) in an adult male subject. In some embodiments, the serum platelet level is between about 210 ($\times 10^9$/L) and about 240 ($\times 10^9$/L) in an adult male subject. In some embodiments, the serum platelet level is between about 210 (×10$^9$/L) and about 222 (×10$^9$/L) in an adult male subject.

In some embodiments, the serum platelet level is below about 140 (×10$^9$/L) in an adult female subject. In some embodiments, the serum platelet level is below about 165 (×10$^9$/L) in an adult female subject. In some embodiments, the serum platelet level is below about 230 (×10$^9$/L) in an adult female subject. In some embodiments, the serum platelet level is between about 140 (×10$^9$/L) and about 295 (×10$^9$/L) in an adult female subject. In some embodiments, the serum platelet level is between about 140 (×10$^9$/L) and about 220 (×10$^9$/L) in an adult female subject. In some embodiments, the serum platelet level is between about 140 (×10$^9$/L) and about 170 (×10$^9$/L) in an adult female subject. In some embodiments, the serum platelet level is between about 165 (×10$^9$/L) and about 300 (×10$^9$/L) in an adult female subject. In some embodiments, the serum platelet level is between about 165 (×10$^9$/L) and about 235 (×10$^9$/L) in an adult finale subject. In some embodiments, the serum platelet level is between about 165 (×10$^9$/L) and about 195 (×10$^9$/L) in an adult female subject. In some embodiments, the serum platelet level is between about 230 (×10$^9$/L) and about 295 (×10$^9$/L) in an adult female subject. In some embodiments, the serum platelet level is between about 230 (×10$^9$/L) and about 265 (×10$^9$/L) in an adult female subject. In some embodiments, the serum platelet level is between about 230 (×10$^9$/L) and about 245 (×10$^9$/L) in an adult female subject.

Reticulocytes:

Another characteristic that may be indicative of hemolytic anemia is a serum reticulocyte level above normal range. Reticulocytes are young red blood cells from which the nucleus has been extruded, but which retain some remnants of ribosomal RNA. Reticulocyte count rises when there is significant blood loss or red blood cells are destroyed prematurely, for instance, through lysis. For purposes of the present invention, the 'normal range' of serum reticulocyte concentration is considered to be within the range of about 0.5 to about 2.0 percent of total red blood cell count; preferably from about 0.5 to about 1.5%; most preferably from about 1.0% to about 1.5%. Reticulocyte counts as a percentage of red blood cells may be higher when hemoglobin levels are low. 'High normal' HgB concentrations would be the upper half (50%) of the normal range, preferably the upper quarter (25%) of the normal range, and most preferably, the upper tenth (10%) of the normal range. [See, WorldWideWeb at nlm.nih.gov and at questdiagnostics.com; Jacobs & DeMott, Laboratory Test Handbook, 5$^{th}$ ed., (LexiComp Inc, Hudson, Ohio)(2001) at p. 481-482]. As is known to one skilled in the art, 'normal ranges' of reticulocytes can vary depending upon the specific laboratory and test.

In some embodiments, the subject has increased reticulocytes. In some embodiments, the subject has a serum reticulocyte concentration of higher than about 1.5% of total red blood cell count. In some embodiments, the subject has a serum reticulocyte concentration of higher than about 2.00% of total red blood cell count. In some embodiments, the subject has a serum reticulocyte concentration between about 1.0% to 1.5% of total red blood cell count. In some embodiments, the subject has a serum reticulocyte concentration between about 1.25% to 1.5% of total red blood cell count. In some embodiments, the subject has a serum reticulocyte concentration between about 1.375% to 1.5% of total red blood cell count. In some embodiments, the subject has a serum reticulocyte concentration between about 1.4% to 1.5% of total red blood cell count. In some embodiments, the subject has a serum reticulocyte concentration between about 1.45% to 1.5% of total red blood cell count. In some embodiments, the subject has a serum reticulocyte concentration between about 1.25% to 2.0% of total red blood cell count. In some embodiments, the subject has a serum reticulocyte concentration between about 1.625% to 2.0% of total red blood cell count. In some embodiments, the subject has a serum reticulocyte concentration between about 1.85% to 2.0% of total red blood cell count.

Bilirubin:

Another characteristic that may be indicative of hemolytic anemia is a serum bilirubin level above normal range. For purposes of the present invention, the 'normal range' of serum bilirubin concentration is considered to be within the range of approximately 0.3 to 1.9 mg/dL; preferably within the range of approximately 0.3 to 1.0 mg/dL. 'High normal' bilirubin concentrations would be the upper half (50%) of the normal range, preferably the upper quarter (25%) of the normal range, and most preferably, the upper tenth (10%) of the normal range. [See, WorldWideWeb at nlm.nih.gov and at questdiagnostics.com; Jacobs & DeMott, Laboratory Test Handbook, 5$^{th}$ ed., (LexiComp Inc, Hudson, Ohio)(2001) at p. 471-472]. As is known to one skilled in the art, 'normal ranges' of bilirubin can vary depending upon the specific laboratory and test.

In certain embodiments, the subject has increased bilirubin. In some embodiments, the subject has a serum bilirubin level of higher than about 1.9 mg/dL. In some embodiments, the subject has a serum bilirubin level of higher than about 1.0 mg/dL. In some embodiments, the subject has a serum bilirubin level between about 1.1 mg/dL and 1.9 mg·dL. In some embodiments, the subject has a serum bilirubin level between about 1.5 mg/dL and 1.9 mg·dL. In some embodiments, the subject has a serum bilirubin level between about 1.75 mg/dL and 1.9 mg·dL. In some embodiments, the subject has a serum bilirubin level between about 0.65 mg/dL and 1.0 mg·dL. In some embodiments, the subject has a serum bilirubin level between about 0.825 mg/dL and 1.0 mg·dL. In some embodiments, the subject has a serum bilirubin level between about 0.93 mg/dL and 1.0 mg·dL.

In certain embodiments, the subject having a complement-mediated hemolytic disorder affecting red blood cells, such as PNH, has previously been treated with a terminal complement inhibitor, but persists in exhibiting at least one of the above characteristics of residual anemia and/or complement-mediated extravascular hemolysis. In such cases, the present invention provides methods and compositions for avoiding or reducing the occurrence and/or severity of at least one of the above characteristics.

In certain embodiments, the subject having a complement-mediated hemolytic disorder affecting red blood cells, such as PNH exhibits a suboptimal response to treatment with a terminal complement inhibitor. Such suboptimal response may include the subject exhibiting at least one of the above characteristics of residual anemia and/or complement-mediated extravascular hemolysis. The method comprises administering an effective amount of a composition that inhibits the activity of the complement alternative pathway, wherein the composition inhibits activation of complement component C3 (C3), for example by inhibiting alternative pathway activation by initiation C3 convertase and/or by inhibiting formation and/or activity of amplifying C3 convertase and opsonization of red blood cells by fragments of C3.

In some embodiments, the subject having a complement-mediated hemolytic disorder affecting red blood cells, such as PNH has previously been treated with a terminal complement inhibitor, being initially responsive to such treatment, and experiencing recurrence. In some embodiments, there is provided a method of treating a complement-mediated hemolytic disorder (such as hemolytic disorder affecting red blood cells for example PNH) in a subject, comprising administering to the subject an effective amount of a composition that inhibits (such as selectively inhibits) activation of the complement alternative pathway, wherein the subject has previously been treated with a terminal complement inhibitor (such as an anti-C5 antibody). In some embodiments, the subject is non-responsive to the treatment of a terminal complement inhibitor (such as an anti-C5 antibody). In some embodiments, the subject is partially responsive to the treatment of a terminal complement inhibitor (such as an anti-C5 antibody). In some embodiments, the subject is initially responsive to the terminal complement inhibitor (such as an anti-C5 antibody) but becomes non-responsive after a certain period (such as a month, two months, three months, four months, six months) of treatment with the anti-C5 antibody. In some embodiments, the individual exhibits one or more of the hemolytic markers discussed above upon treatment with the terminal complement inhibitor (such as anti-C5 antibody). In some embodiments, the complement activation pathway inhibitors is a targeted construct (such as targeted constructs described herein) that comprise a targeting moiety which directs the construct to a site of complement activation and an active moiety which has complement inhibitory activity. In some embodiments, the targeted construct comprises a CR2 or a fragment thereof and a factor H or a fragment thereof. In some embodiments, the targeted construct comprises the first four SCR domains of CR2 and the first five SCR domains of factor H (such as TT30). In some embodiments, the subject was terminated with the treatment of the terminal complement inhibitor for at least 1, 2, 3, 4, 5, 6, 7, 8, 9, or 10 weeks prior to the treatment with the inhibitor of the alternative complement pathway. In some embodiments, the subject has progressed on a prior therapy (for example progressed after any of about 3, 6, 9, or 12 months upon initiation of the prior therapy).

In another aspect, the invention provides for methods of treating a subject having paroxysmal nocturnal hemoglobinuria (PNH) or another disease which involves a complement-mediated extravascular hemolysis component, the method comprising administering a composition comprising a combination comprising (i) an effective amount of an inhibitor of the complement alternative pathway and (ii) an effective amount of a terminal complement inhibitor. Additional complement inhibitors (such as inhibitors of the complement alternative pathway can also be administered.

The composition comprising an inhibitor of the complement alternative pathway and a terminal complement inhibitor can be administered simultaneously. The term "simultaneous administration," as used herein, means that the composition comprising an inhibitor of the complement alternative pathway and terminal complement inhibitor in a combination therapy are administered with a time separation of no more than about 15 minutes, such as no more than about any of 10, 5, or 1 minutes. When the drugs are administered simultaneously, the composition comprising an inhibitor of the complement alternative pathway and the terminal complement inhibitor may be contained in the same composition (e.g., a composition comprising both the inhibitor of the complement alternative pathway and the terminal complement inhibitor) or in separate compositions (e.g., the composition comprising an inhibitor of the complement alternative pathway is contained in one composition and the terminal complement inhibitor is contained in another composition).

Alternatively, the inhibitor of the complement alternative pathway and the terminal complement inhibitor are administered sequentially, i.e., the composition comprising the inhibitor of the complement alternative pathway is administered either prior to or after the administration of the terminal complement inhibitor. As used herein, the term "sequential administration" means that the composition comprising an inhibitor of the complement alternative pathway and the terminal complement inhibitor are administered with a time separation of more than about 15 minutes, such as more than about any of 20, 30, 40, 50, 60, or more minutes. Either the composition comprising an inhibitor of the complement alternative pathway or the terminal complement inhibitor may be administered first. The composition comprising an inhibitor of the complement alternative pathway and the terminal complement inhibitor are contained in separate compositions, which may be contained in the same or different packages or kits. In some embodiments, the composition comprising the inhibitor of the complement alternative pathway is administered prior to the administration of the terminal complement inhibitor. In some embodiments, the composition comprising the inhibitor of the complement alternative pathway is administered after the administration of the terminal complement inhibitor.

In some embodiments, the administration of the composition comprising the inhibitor of the complement alternative pathway and the complement inhibitor are concurrent, i.e., the administration period of the composition comprising the inhibitor of the complement alternative pathway and that of the terminal complement inhibitor overlap with each other. In some embodiments, the composition comprising the inhibitor of the complement alternative pathway is administered for at least one cycle (for example, at least any of 2, 3, or 4 cycles) prior to the administration of the terminal complement inhibitor. In some embodiments, the terminal complement inhibitor is administered for at least any of one, two, three, or four weeks.

In some embodiments, the administrations of the composition comprising the inhibitor of the complement alternative pathway and the terminal complement inhibitor are non-concurrent. For example, in some embodiments, the administration of the composition comprising the inhibitor of the complement alternative pathway is terminated before the terminal complement inhibitor is administered. In some embodiments, the administration of the terminal complement inhibitor is terminated before the composition comprising the inhibitor of the complement alternative pathway is administered. In some embodiments, the time period between these two non-concurrent administrations can range from about one day to about eight weeks. In some embodiments, the time period between these two non-concurrent administrations is about one day. In some embodiments, the time period between these two non-concurrent administrations is more than about one day, such as about two, three, four, five, six days. In some embodiments, the time period between these two non-concurrent administrations is at least about one week. In some embodiments, the time period between these two non-concurrent administrations is at least about two weeks. In some embodiments, the time period between these two non-concurrent administrations is at least about four weeks. In some embodiments, the time period between these two non-concurrent administrations is at least about eight weeks.

The dosing frequency of the composition comprising the inhibitor of the complement alternative pathway and the terminal complement inhibitor may be adjusted over the course of the treatment, based on the judgment of the administering physician. When administered separately, the composition comprising the inhibitor of the complement alternative pathway and the terminal complement inhibitor can be administered at different dosing frequency or intervals. For example, the composition comprising the inhibitor of the complement alternative pathway can be administered weekly, while a terminal complement inhibitor can be administered more or less frequently. In some embodiments, sustained continuous release formulation of the composition comprising the inhibitor of the complement alternative pathway and/or terminal complement inhibitor may be used. Various formulations and devices for achieving sustained release are known in the art.

The composition comprising the inhibitor of the complement alternative pathway and the terminal complement inhibitor can be administered using the same route of administration or different routes of administration. In some embodiments (for both simultaneous and sequential administrations), the composition comprising the inhibitor of the complement alternative pathway and the terminal complement inhibitor are administered at a predetermined ratio.

Targeting to Complement Activated Tissue

The compositions described herein preferably are targeted for increased association to tissue which has been injured, damaged or has become inflamed by physical, chemical or other insult or injury. Targeting can be accomplished by tethering, fusing or otherwise associating an active agent to a targeting moiety. In some embodiments, the targeting moiety binds to a binding partner associated with complement activation. "A binding partner associated with complement association" refers to a molecule or epitope that is present at the site of complement activation. In some embodiments, the molecule or epitope is only present when a complement pathway is activated. In some embodiments, the molecule or epitope is available for binding to the targeting moiety only when a complement pathway is activated. In some embodiments, the targeting moiety binds to tissue-associated complement component 3 (C3) or one or more fragments of C3, including, but not limited to: C3b, iC3b, C3d and C3dg. In preferred embodiments, the targeting moiety will bind to complement component 3 (C3) or one or more fragments of C3, including, but not limited to: C3b, iC3b, C3d and C3dg. Preferred targeting moieties include, for example, complement receptor 2 (CR2) or fragments thereof that retain the ability to bind to one or more fragments of C3; monoclonal antibodies to C3, C3b, iC3b, C3d, C3dg, or other fragments of C3. It is also possible to use some of the non-regulatory fragments of Factor H that retain the ability to bind to one or more fragments of C3, including C3b, iC3b and C3d or other fragments of C3. These fragments potentially include fragments comprising SCR domains 5-8 and SCR domains 19-20. It should be noted that the term "CR2-targeted" may be used in the present invention to mean that a molecule will specifically bind to one or more fragments of C3, such as C3, C3b, iC3b, C3d and C3dg, in a manner analogous to the natural binding of CR2. Thus, for example, both a fusion protein that comprises either (a) a targeting moiety derived from CR2 or (b) an antibody to C3d; fused to complement Factor H may be referred to as a "CR2-targeted Factor H."

In some embodiments, the construct is a fusion protein comprising the targeting moiety and the active moiety. In some embodiments, the targeting moiety and the active moiety are fused through a peptide linker. In some embodiments, the targeting moiety and the active moiety are joined by a non-peptide linker. In some embodiments, the targeting moiety is fused to the N-terminus of the active moiety. In some embodiments, the targeting moiety is fused to the C-terminus of the active moiety. In some embodiments the targeting moiety is inserted in the middle of the active moiety.

Exemplary fusion proteins include, but are not limited to, polypeptides in which the C-terminal portion of a targeting moiety is fused to the N-terminal portion of the active moiety, the N-terminal portion of a targeting moiety is fused to the C-terminal portion of the active moiety, two or more targeting moieties fused to both the N-terminal and the C-terminal portions of the active moiety, the targeting moiety inserted in the middle of the active moiety, and the like.

In some embodiments, the molecule comprises two or more (such as any of two, three, four, five, or more) CR2 portions (or any other target moiety portion, or combinations thereof). These CR2 portions (or other target moiety portions) may be the same or different, for example in terms of amino acid sequences, structures, and/or functions.

In some embodiments, the molecule comprises two or more (such as any of two, three, four, five, or more) active moiety portions. These active moiety portions may be the same or different, for example in terms of amino acid sequences, structures, and/or functions.

In some embodiments, the molecule (such as a fusion protein) comprises: 1) two or more CR2 portions comprising a CR2 or a fragment thereof, and 2) two or more active moieties In some embodiments, the targeting moiety exhibits high avidity for its binding partner. In some embodiments, the targeting moiety exhibits high avidity but low affinity to its binding partner. Binding avidity is a measure of the strength of the initial process by which a targeting moiety, such as an antibody or ligand, will seek out, locate and bind with its binding partner, and is the initial process involved in binding affinity. Binding affinity, on the other hand, is a broader measure which also takes into account not only avidity, but other characteristics of binding such as strength of interaction and coefficients of dissociation.

Methods have been developed for the measurement and modification of binding attributes, such as avidity and affinity. For example, see Lee et al., Molecular Immunology, 47:816-24 (2010); Kaymakcalan et al., Clinical Immunology, 131:308-16 (2009); Konstandin et al., J. Immunol. Methods, 310:67-77 (2006); and Oda et al., Molecular Immunology, 37:1111-22 (2000). Accordingly, the present invention may include methods for assessing the binding avidity and affinity of a targeting moiety; mutating or modifying the targeting moiety and assessing the effects of such mutation or modification, in order to obtain targeting moieties with improved targeting characteristics, e.g., binding avidity.

Although certain sections herein discuss CR2-targeted constructs, it is understood that the same applies to other targeting moieties described herein. The different targeting moieties are described herein in more detail.

CR2 and CR2 Fragments.

The use of complement receptor 2 (CR2), or functional fragments thereof, to target complement modulators to tissue which exhibit or express C3, or fragments of C3 to which the CR2 is able to bind, including C3b, iC3b, C3d and C3dg, is described in US 2008/0267980, Tomlinson and Holers, the disclosure of which is hereby incorporated herein by reference. Such CR2 molecules, and functional fragments thereof, can be used in the present invention as the targeting moiety. In particularly preferred embodiments, the first two N-terminal short concensus repeat domains (SCRs), comprising an active binding site for C3dg, can be used in the present invention as the targeting moiety. The present inventors have found that, while red blood cells are normally privileged from complement attack, the complement-mediated blood disorders treatable by the present invention may lead to abnormal coating of the RBC surface with C3 and/or C3 fragments, rendering the affected RBCs vulnerable to complement attack and opsonization.

Human complement receptor 2, also referred to as CD21 (CR2/CD21) (SEQ ID NO:1 and SEQ ID NO:2), is a ~145 kD transmembrane protein of the C3 binding protein family comprising 15 or 16 short consensus repeat (SCR) domains, structural units characteristic of such proteins. CR2 is expressed on mature B cells and follicular dendritic cells, and plays an important role in humoral immunity. J. Hannan et al., Biochem. Soc. Trans. (2002) 30:983-989; K. A. Young et al., J. Biol. Chem. (2007) 282(50):36614-36625. CR2 protein does not bind intact C3 protein, but binds its breakdown products, including the C3b, iC3b, and C3d cleavage fragments, via a binding site located within the first two amino-terminal short consensus repeats ("SCRs 1-2") of the CR2 protein. Consequently, the SCR1-2 domain of CR2 discriminates between cleaved (i.e., activated) forms of C3 and intact circulating C3. As a targeting group, SCRs 1-2 of CR2 are therefore able to discriminate between circulating C3 and the C3 fragments generated during complement activation. While the affinity of CR2 for C3d is only 620-658 nM (J. Hannan et al., Biochem. Soc. Trans. (2002) 30:983-989; J. M. Guthridge et al., Biochem. (2001) 40:5931-5941), the avidity of CR2 for clustered C3d makes it an effective method of targeting molecules to sites of complement activation.

CR2 contains an extracellular portion having 15 or 16 repeating units known as short consensus repeats (SCR domains). The SCR domains typically have a framework of highly conserved residues including four cysteines, two prolines, one tryptophan and several other partially conserved glycines and hydrophobic residues. SEQ ID NO:1 represents the full-length human CR2 protein sequence having 15 SCR domains. Amino acids 1-20 of SEQ ID NO:1 comprise the leader peptide, amino acids 23-82 of SEQ ID NO:1 comprise SCR1, amino acids 91-146 of SEQ ID NO:1 comprise SCR2, amino acids 154-210 of SEQ ID NO:1 comprise SCR3, amino acids 215-271 of SEQ ID NO:1 comprise SCR4. The active site (C3d binding site) is located in SCR1-2 (the first two N-terminal SCR domains) (SEQ ID NO:2). These SCR domains are separated by short sequences of variable length that serve as spacers. It is understood that species and strain variations exist for the disclosed peptides, polypeptides, and proteins, and that the CR2 or a fragment thereof described herein encompasses all species and strain variations.

In certain embodiments, the CR2 portion comprises a polypeptide that contains some or all of the ligand binding sites of the CR2 protein, and includes, but is not limited to, full-length CR2 proteins (such as human CR2 as shown in SEQ ID NO:1), soluble CR2 proteins (such as a CR2 fragment comprising the extracellular domain of CR2), other biologically active fragments of CR2, a CR2 fragment comprising SCR1-2 (SEQ ID NO:2), or any homolog of a naturally occurring CR2 or fragment thereof, as described in detail below. In some embodiments, the CR2 portion has at least one of the following properties or CR2: (1) the ability to bind to C3d, (2) the ability to bind to iC3b, (3) the ability to bind to C3dg, (4) the ability to bind to C3d, and (5) the ability to bind to one or more cell-bound fragments of C3b that bind to the two N-terminal SCR domains of CR2.

In certain embodiments, the CR2 portion comprises the first two N-terminal SCR domains of CR2 (SEQ ID NO:2). In certain embodiments, the CR2 portion comprises the first three N-terminal SCR domains of CR2. In certain embodiments, the CR2 portion comprises the first four N-terminal SCR domains of CR2. In certain embodiments, the CR2 portion comprises (and in some embodiments consists of or consists essentially of) at least the first two N-terminal SCR domains of CR2, including for example at least any of the first 3, 4, 5, 6, 7, 8, 9, 10, 11, 12, 13, 14, or 15 SCR domains of CR2.

Cleavage of C3 results initially in the generation and deposition of C3b on the activating cell surface. The C3b fragment is involved in the generation of enzymatic complexes that amplify the complement cascade. On a cell surface, C3b is rapidly converted to inactive iC3b, particularly when deposited on a host surface containing regulators of complement activation (i.e., most host tissue). Even in the absence of membrane-bound complement regulators, substantial levels of iC3b are formed because of the action of serum factor H and serum factor I. iC3b is subsequently digested to the membrane-bound fragments C3dg and then C3d by factor I and other proteases and cofactors, but this process is relatively slow. Thus, the C3 ligands for CR2 are relatively long lived once they are generated and are present in high concentrations at sites of complement activation.

Antibodies to C3 and C3 Fragments. Antibodies to C3 and C3 Fragments.

In place of a targeting moiety derived from CR2, the targeting moiety may comprise antibodies which bind to C3 or C3 fragments such as C3b, iC3b, C3d and C3dg, or an antigen-binding fragment thereof. Antibodies that bind to C3 and to cleavage fragments C3b and C3d, are known. For example, see U.S. Pat. No. 6,572,856, Taylor; Tosic et al., J. Immunological Methods, 120:241-249 (1989); Sokoloff et al., Cancer Immunology and Immunotherapy, 49:551-562 (2000); Mastellos et al., Molecular Immunology, 40:1213-1221 (2004); Dilillo et al., Molecular Immunology, 43:1010-1019 (2006); Campagne, US 2009/0081211; Etemad-Gilbertson et al., US 2009/0175875; Aguado et al., J. Clin. Invest., 76:1418-1426 (1985). The disclosure of these documents is hereby incorporated herein by reference. Such antibodies, and functional fragments thereof, may be useful in the present invention as the targeting moiety for directing therapeutic fragments to tissue experiencing activated complement activity, and thus expressing C3 or its fragments. Functional fragments of antibodies may include, for example, single-chain variable fragments (scFvs) which preferably comprise of $V_H$ and $V_L$ domains, optionally joined by a flexible peptide linker. Such scFvs usually retain the specificity of the parental antibody and bind the target antigen in a monovalent manner. Conversion of antibodies to scFvs is well known process (see Nat. Biotechnol. 23:1126 (2005); Biomol Eng. 24:201 (2007); J Immunol Methods., 168:149 (1994); Arch Virol. 148:497 (2003). ScFvs can be constructed by either de novo gene synthesis, overlap extension polymerase chain reaction (PCR) or sequential ligation of the individual heavy ($V_H$) and light ($V_L$) chain variable gene segments. Sequential cloning of the individual $V_H$ and $V_L$ genes into a vector containing the synthetic linker sequence (e.g., (Gly$_4$Ser)$_3$) can be performed as well. The sequence can be either V$_H$-linker-V$_L$ or V$_L$-linker-V$_H$.

In particularly preferred embodiments, the targeting moiety may comprise an antibody which binds to C3d, such as those produced by: (1) hybridoma cell line 3d-9a/25, deposited on May 26, 2010, and designated as ATCC Patent Deposit PTA-10998; (2) hybridoma cell line 3d-8b/2, deposited on May 26, 2010, and designated as ATCC Patent Deposit PTA-10999; (3) hybridoma cell line 3d-29/5/2, deposited on May 26, 2010, and designated as ATCC Patent Deposit PTA-11000; (4) hybridoma cell line 3d-10/14/1, deposited on Jun. 2, 2010, and designated as ATCC Patent Deposit PTA-11010; (5) hybridoma cell line 3d-11/14, deposited on Jun. 2, 2010, and designated as ATCC Patent Deposit PTA-11011; (6) hybridoma cell line 3d-15A9, deposited on Jun. 2, 2010, and designated as ATCC Patent Deposit PTA-11012; (7) hybridoma cell line 3d-3/28/4, deposited on Jun. 9, 2010, and designated as ATCC Patent Deposit PTA-11025; (8) hybridoma cell line 3d-16/3/3, deposited on Jun. 9, 2010, and designated as ATCC Patent Deposit PTA-11026; and (9) hybridoma cell line 3d-31/A6/9, deposited on Jun. 9, 2010, and designated as ATCC Patent Deposit PTA-11027. Those antibodies are described in more detail in the U.S. Provisional Patent Application Ser. No. 61/357,499, filed on Jun. 22, 2010, entitled "Antibodies to the C3d Fragment of Complement Component 3," which is incorporated herein by reference in its entirety. The complete nucleotide and amino acid sequences of the monoclonal antibodies produced by those hybridoma cell lines can easily be determined with standard methods such as, for example, the polymerase chain reaction (PCR) and automated sequencing.

Conversion of Anti-C3d Monoclonal Antibodies into Single-Chain Variable Fragments (scFvs).

Conversion of antibodies to scFvs is well known process (see Nat. Biotechnol. 23:1126 (2005); Biomol Eng. 24:201 (2007); J Immunol Methods., 168:149 (1994); Arch Virol. 148:497 (2003). ScFvs can be constructed by either de novo gene synthesis, overlap extension polymerase chain reaction (PCR) or sequential ligation of the individual heavy (V$_H$) and light (V$_L$) chain variable gene segments. Sequential cloning of the individual V$_H$ and V$_L$ genes into a vector containing the synthetic linker sequence (e.g., (Gly$_4$Ser)$_3$) can be performed as well. The sequence can be either V$_H$-linker-V$_L$ or V$_L$-linker-V$_H$. Engineered anti-C3d-scFvs can be linked to complement inhibitors such as CFI. Single chain Fvs of the present invention preferably comprise of V$_H$ and V$_L$ domains joined by flexible peptide linker that prevents the dissociation. AntiC3d monoclonal antibody can be converted into single-chain variable fragments in an equivalent manner as described above. The scFvs usually retain the specificity of the parental antibody and bind the target antigen in a monovalent manner.

A series of linkers can be used to identify the optimal distance between antiC3d-scFv and CFI-related targeting moiety, ranging from no linker to linker of 40 amino acids, and the sequence chosen for the linker can be for example (GlyGlyGlyGlySer)n where n=0-8. The construction of the antiC3d-scFv linked to CFI-related moiety can be done by de novo gene synthesis, overlap PCR, sequential cloning or ligation. The N-terminal moiety of the final construct can be either CFI-related moiety or antiC3d-scFv.

Factor H and FH Fragments

Factor H has at least three distinct binding domains for C3b, which are located within SCRs 1-4; SCRs 5-8, and SCRs 19-20. Each site of Factor H binds to a distinct region within the C3b protein: N terminal sites bind to native C3b; the second site, located in the middle region of factor H, binds to the C3c fragment; and the site located within SCR19-20 binds to the C3d region. Factor H also contains binding sites for heparin, which are located within SCR 7, SCRs 5-12 and SCRs 19-20 of Factor H and overlap with those of the C3b binding sites. In some embodiments, the targeting moiety comprises a non-complement regulatory fragments of Factor H that retain the ability to bind to one or more fragments of C3, including C3b, iC3b and C3d or other tissue-associated fragments of C3. In some embodiments, the target moiety comprises SCR domains 5-8 and SCR domains 19-20 of factor H.

As used herein, the term "complement factor H," "factor H," or "FH" refers to complement factor H, a single polypeptide chain plasma glycoprotein, including homologs thereof. The protein is composed of 20 conserved short consensus repeat (SCR) domains of approximately 60 amino acids, arranged in a continuous fashion like a string of beads, separated by short linker sequences of 2-6 amino acids each. Factor H binds to C3b, accelerates the decay of the alternative pathway C3-convertase (C3bBb), and acts as a cofactor for the proteolytic inactivation of C3b. In the presence of factor H, proteolysis by factor I results in the cleavage and inactivation of C3b. Factor H has at least three distinct binding domains for C3b, which are located within SCRs 1-4, SCRs 5-8, and SCRs 19-20. Each site of factor H binds to a distinct region within the C3b protein: the N-terminal sites bind to native C3b; the second site, located in the middle region of factor H, binds to the C3c fragment and the site located within SCR19 and 20 binds to the C3d region. In addition, factor H also contains binding sites for heparin, which are located within SCR 7, SCRs 5-12, and SCR 20 of factor H and overlap with those of the C3b binding sites. Structural and functional analyses have shown that the domains for the complement inhibitory activity of factor H are located within the first four N-terminal SCR domains.

Antibodies to Inflammatory Neoepitopes.

In other preferred embodiments, the targeting moiety may comprise an antibody which binds to an inflammatory neoepitope, such as annexin IV, annexin A2, phospholipids, such as cardiolipin, and citrulline-modified protein. Suitable antibodies may include, for example, antibody B4, which binds to annexin IV; antibody C2, which binds to cardiolipin; and antibody D5, which binds to citrulline-modified protein (See Holers et al., WO 2007/112403; Thurman and Holers, WO 2010/034015); See also, Allison, U.S. Pat. Nos. 6,962,903; 7,407,475 (Annexin V); U.S. Pat. Nos. 7,635, 676; 7,635,678; 7,635,679; 7,635,680; and 7,645,739; proximal tubule targeting moiety, see Quigg et al., US 2005/0265995. As described above, functional fragments of antibodies such as ScFvs can be used as the targeting moiety. The complete nucleotide and amino acid sequences of the monoclonal antibodies produced by those hybridoma cell lines can easily be determined with standard methods such as, for example, the polymerase chain reaction (PCR) and automated sequencing.

Other Targeting Moieties.

The present invention also contemplates that other targeting moieties may be used. The targeting moiety should ideally bind to one or more of the fragments of C3 that bind to cells in areas of complement activation. This also includes targeting moieties that bind to one or more neoepitopes that are expressed on cells in areas of complement activation.

Inhibition of Complement Alternative Pathway

The compositions described herein in some embodiments comprise an active agent moiety that significantly or selectively inhibits the complement alternative pathway. By "significantly inhibiting the complement alternative pathway" it is meant that the active agent inhibits the complement alternative pathway with a potency or percent inhibition that measures at least 10%, preferably 20%, 30% or 40%, and more preferably at least about 50%, 60%, 80% or 90% of alternative complement activity in the absence of said active agent moiety. By "selectively inhibits the complement alternative pathway" it is meant that the active agent inhibits the complement alternative pathway with a potency or percent inhibition which measures at least two, three, four, five or ten times greater than that of the classical or lectin complement pathways. More preferably, the active agent will selectively inhibit the complement alternative pathway at a potency or percent inhibition of at least one, two or three orders of magnitude greater than that the classical or lectin complement pathways.

In preferred embodiments, active agent moiety comprises an inhibitor of the complement alternative pathway, or a biologically active fragment thereof, selected from the group consisting of Factor H protein, Crry, Decay Accelerating Factor (DAF), MCP, CR1, or biologically active fragments thereof. In some embodiments, the active moiety is an inhibitor of the amplification loop of the alternative complement pathway and will prevent the formation and activity of the amplification C3 convertase, as well as the downstream C5 convertase. In some embodiments, the active moiety will be able to inactivate the initiation C3 convertase once it is formed on the red blood cell surface, and may partially prevent formation of the initiation C3 convertase in the fluid phase.

In a particularly preferred embodiment, the active agent moiety comprises Factor H protein or a biologically active fragment thereof, which retains the ability to inhibit the complement alternative pathway. Suitable Factor H protein an biologically active fragments thereof include the first four N-terminal short consensus sequences (SCRs of Factor H, and are described in US 2008/0221011, Gilkeson et al, the disclosure of which is hereby specifically incorporated herein by reference.

Other complement inhibitors, and fragments thereof, which may be useful as the active agent moiety in the present invention are described, for example, in Tomlinson and Holers, US 2008/0267980. Suitable complement inhibitors, for example, may include complement receptor 1 (CR1); MCP; Crry; or DAF. The disclosure of Tomlinson and Holers is hereby specifically incorporated herein by reference. Other complement inhibitors, which may be useful as the active agent moiety include compstatin, see Janssen et al., J. Biol. Chem. 282:29241-7 (2007). In preferred embodiments, the complement inhibitor is an inhibitor of the amplification loop of the alternative complement pathway.

In certain embodiments, the active moiety comprises two or more complement inhibitors, for example, two or more biologically active fragments of factor H as in TT31; or an active fragment of factor H in combination with an active fragment of complement receptor 1, MCP; Crry; complement factor I; CD59 or DAF. In such embodiments, the active moiety may be provided in multiple forms, for example, when the active moiety comprises a combination of Factor H and CD59, the composition may include two or more of the following: CR2-FH-CD59; CR2-CD59-FH; antiC3d-FH-CD59 and antiC3d-CD59-FH.

As used herein, the term "biologically active" fragment of a complement inhibitor refers a fragment of the complement inhibitor which retains some or all of the inhibitory activity of the full-length complement inhibitory protein. For example, "biologically active" fragments of factor H include, but are not limited to, factor H fragments comprising SCRs 1-4, SCRs 1-5, SCRs 1-8, SCRs 1-18, SCRs 19-20, or any homolog of a naturally-occurring factor H or fragment thereof, as described in detail below. In certain embodiments, the biologically active fragment of factor H has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

It is contemplated that variants and modifications of the complement inhibitors described above may be used as the active agent moiety in certain embodiments of the present invention. For example, through deletion analysis, it may be possible to identify smaller fragments of some of the above complement inhibitors, which comprise the minimal sequence elements required for complement inhibition. In other embodiments, the complement inhibitors, or the minimal sequence elements thereof required for complement inhibition, may be modified in order to increase half-life, stability or potency of the active agent moiety as an inhibitor. For example, the active agent moiety may comprise the complement inhibitor, or active fragment thereof, tethered to a protein or non-protein scaffold which is intended to maintain the active agent moiety in a conformation capable of complement inhibition, while reducing susceptibility to proteases or otherwise extending the half-life, stability or potency of the active agent moiety.

The following description refers to methods and compositions in which the targeted therapeutic agent is a fusion protein comprising a targeting moiety derived from CR2 and an active agent derived from FH (CR2-FH fusion protein). This description is non-limiting, and one skilled in the art will be able to practice the invention with respect to other embodiments of the invention, including the alternative targeting moieties and alternative active moieties that are mentioned herein.

Also contemplated are inhibitors that inhibit the complement alternative pathway indirectly. For example, in some embodiments, the inhibitor inhibits two or more complement pathways. In some embodiments, the inhibitor inhibits the lectin complement pathway (for example, in some embodiments, the inhibitor is an anti-MASP antibody). In some embodiments, the inhibitor inhibits the classical pathway (for example, in some embodiments, the inhibitor is CR1). Other complement inhibitors are also contemplated.

In some embodiments, the targeted construct described herein comprises two or more complement inhibitors or fragments thereof. These two or more complement inhibitors or fragments thereof in each construct can be the same or different. The two or more complement inhibitors or fragments thereof in each construct can inhibit the same or different complement pathways.

Compositions:

The compositions described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection).

In some embodiments, the compositions are administered intravascularly, such as intravenously or intraarterially. In some embodiments (for example for the treatment of renal diseases), the compositions are administered directly into arteries (such as renal arteries). In preferred embodiments, the compositions are administered subcutaneously.

The optimal effective amount of the compositions can be determined empirically and will depend on the type and severity of the disease, route of administration, disease progression and health, mass and body area of the individual. Such determinations are within the skill of one in the art. The effective amount can also be determined based on in vitro complement activation assays. Examples of dosages of CR2-FH molecules which can be used for methods described herein include, but are not limited to, an effective amount within the dosage range of any of about 0.01 ug/kg to about 300 mg/kg, or within about 0.1 ug/kg to about 40 mg/kg, or with about 1 ug/kg to about 20 mg/kg, or within about 1 ug/kg to about 10 mg/kg, or within about 0.1 mg/kg to about 100 mg/kg, or within about 0.1 mg/kg to 50 mg/kg or within about 0.1 mg/kg to about 25 mg/kg, or within about 0.1 mg/kg to about 10 mg/kg. In some embodiments, the effective amount is about 0.1 mg/kg to about 10 mg/kg. In some embodiments, the effective amount is about 0.1 mg/kg to about 20 mg/kg. In some embodiments, the effective amount is about any one of 0.1, 0.5, 1, 2, 3, 4, 5, 6, 7, 8, 9, 10, 11, 12, 13, 14, 15, 16, 17, 18, 19 or 20 mg/kg. For example, when administered subcutaneously, the composition may be administered at low microgram ranges, including for example about 0.1 ug/kg or less, about 0.05 ug/kg or less, or 0.01 ug/kg or less. In some embodiments, the amount of CR2-FH administered to an individual is about 10 ug to about 500 mg per dose, including for example any of about 10 ug to about 50 ug, about 50 ug to about 100 ug, about 100 ug to about 200 ug, about 200 ug to about 300 ug, about 300 ug to about 500 ug, about 500 ug to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg, or about 900 mg to about 1000 mg per dose.

The CR2-FH compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implanted in various locations in the body.

In some embodiments, the composition (such as TT30) is provided in water or saline at a concentration of about 1, 2, 3, 4, 5, 6, 7, 8, 9, or 10 mg/ml.

In certain embodiments of the invention, the dosing of CR2-FH fusion protein is titrated such that the dose is sufficient to reduce or prevent red blood cell lysis, and may fully or partially inhibit or block the formation and activity of the amplification C3 convertase (C3bBb) on the red blood cell surface; but at a low enough concentration such that C3 coating of abnormal cells is still observed systemically, such that the C3 is able to form initiation C3 convertase (C31Bb) in the fluid phase.

Gene Therapy

The CR2-FH molecules can also be delivered by expression of the CR2-FH fusion protein in vivo, which is often referred to as "gene therapy." For example, cells may be engineered with a polynucleotide (DNA or RNA) encoding for the fusion protein ex vivo, the engineered cells are then provided to an individual to be treated with the fusion protein. Such methods are well-known in the art. For example, cells may be engineered by procedures known in the art by use of a retroviral particle containing RNA encoding for the fusion protein of the present invention. Local delivery of the fusion proteins of the present invention using gene therapy may provide the therapeutic agent to a localized target area.

Methods of gene delivery are known in the art. These methods include, but are not limited to, direct DNA transfer, see, e.g., Wolff et al. (1990) Science 247: 1465-1468; 2) Liposome-mediated DNA transfer, see, e.g., Caplen et al. (1995) Nature Med. 3:39-46; Crystal (1995) Nature Med. 1:15-17; Gao and Huang (1991) Biochem. Biophys. Res. Comm. 179:280-285; 3) Retrovirus-mediated DNA transfer, see, e.g., Kay et al. (1993) Science 262:117-119; Anderson (1992) Science 256:808-813; 4) DNA Virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al. (1994) Gene Therapy 1:367-384; U.S. Pat. No. 4,797,368, incorporated herein by reference, and U.S. Pat. No. 5,139,941.

Retroviruses from which the retroviral plasmid vectors hereinabove mentioned may be derived include, but are not limited to, Moloney Mouse Leukemia Virus, spleen necrosis virus, retroviruses such as Rotis Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Mouse Leukemia Virus.

Adenoviruses have the advantage that they have a broad host range, can infect quiescent or terminally differentiated cells, such as neurons or hepatocytes, and appear essentially non-oncogenic. See, e.g., Ali et al. (1994), supra, p. 367. Adenoviruses do not appear to integrate into the host genome. Because they exist extrachromosomally, the risk of insertional mutagenesis is greatly reduced. Ali et al. (1994), supra, p. 373.

Adeno-associated viruses exhibit similar advantages as adenoviral-based vectors. However, AAVs exhibit site-specific integration on human chromosome 19 (Ali et al. (1994), supra, p. 377).

The gene therapy vectors may include one or more promoters. In some embodiments, the vector has a promoter that drives expression in multiple cell types. In some embodiments, the vector has a promoter that drives expression in specific cell types (such as cells of retina or cells in the kidney). Suitable promoters which may be employed include, but are not limited to, the retroviral LTR; the SV40 promoter; and the human cytomegalovirus (CVM) promoter described in Miller et al. (1989) Biotechniques 7(9):980-990, or any other promoter (e.g., cellular promoters such as eukaryotic cellular promoters including, but not limited to, the histone, pol III, and .beta.-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding a CR2-FH fusion protein is preferably under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoA1 promoter; human globin promoters; viral thymidine kinase promoters, such as the Herpes Simplex thymidine kinase promoter; retroviral LTRs (including the modified retroviral LTRs hereinabove described); the .beta.-actin promoter; and human growth hormone promoter.

Retroviral plasmid vectors can be employed to transduce packaging cell lines to form producer cell lines. Examples of packaging cells which maybe transfected are described in Miller (1990) Human Gene Therapy 1:5-14. The vectors may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

In some embodiments, the complement activation is inhibited by contacting a body fluid with a composition comprising a CR2-FH molecule ex vivo under conditions that permit the CR2-FH molecule to function to inhibit complement activation. Suitable body fluids include those that can be returned to the individual, such as blood, plasma, or lymph. Affinity adsorption apheresis is described generally in Nilsson et al. (1988) Blood 58(1):38-44; Christie et al. (1993) Transfusion 33:234-242; Richter et al. (1997) ASAIO J. 43(1):53-59; Suzuki et al. (1994) Autoimmunity 19: 105-112; U.S. Pat. No. 5,733,254; Richter et al. (1993) Metabol. Clin. Exp. 42:888-894; and Wallukat et al. (1996) Int'l J. Card. 54:1910195.

Accordingly, the invention includes methods of treating one or more diseases described herein in an individual comprising treating the individual's blood extracoporeally (i.e., outside the body or ex vivo) with a composition comprising a CR2-FH molecule under conditions that permit the molecule to function to inhibit complement activation, and returning the blood to the individual.

Unit Dosages, Articles of Manufacture, and Kit

Also provided are unit dosage forms of CR2-FH molecule compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the CR2-FH molecule. In some embodiments, the unit dosage forms of CR2-FH molecule composition comprises about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 5.0 mg-15 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg CR2-FH molecule. In some embodiments, the unit dosage form comprises about 0.25 mg CH2-FH molecule. In other embodiments, the unit dosage form comprises about 10 mg CH2-FH molecule. The term "unit dosage form" refers to a physically discrete unit suitable as unitatry dosages for an individual, each unit containing a predetermined quantity of active material calculated to produce the desired therapeutic effect, in association with a suitable pharmaceutical carrier, diluent, or excipient. These unit dosage forms can be stored in a suitable packaging in single or multiple unit dosages and may also be further sterilized and sealed.

In some embodiments, the composition (such as TT30) is provided in water or saline at a concentration of about 1, 2, 3, 4, 5, 6, 7, 8, 9, or 10 mg/ml.

Also provided are articles of manufacture comprising the compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions (or unit dosages forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

The compositions and formulations of the present invention are useful for the treatment of conditions associated with complement activation, preferably those which involve the complement alternative pathway, which is largely unaffected by terminal complement inhibitors [e.g., inhibitors of steps of the complement pathway subsequent to the activation of C3].

In the foregoing specification and in the examples below, the invention has been described with specific embodiments thereof. However, it will be evident to those skilled in the art that various modifications and changes may be made thereto without departing from the broader scope of the invention.

All publications that are cited herein are hereby specifically incorporated herein by reference into the disclosure for the teachings for which they are cited.

EXAMPLES

Example 1. Demonstration of Possible Mechanism of Protection of Red Blood Cells from Hemolytic Lysis in Paroxysmal Nocturnal Hemoglobinuria (PNH)

This example uses TT30 (SEQ ID NO:3) and PNH as an example to demonstrate a possible mechanism under which TT30 can protect red blood cells from hemolytic lysis.

Figure 20:
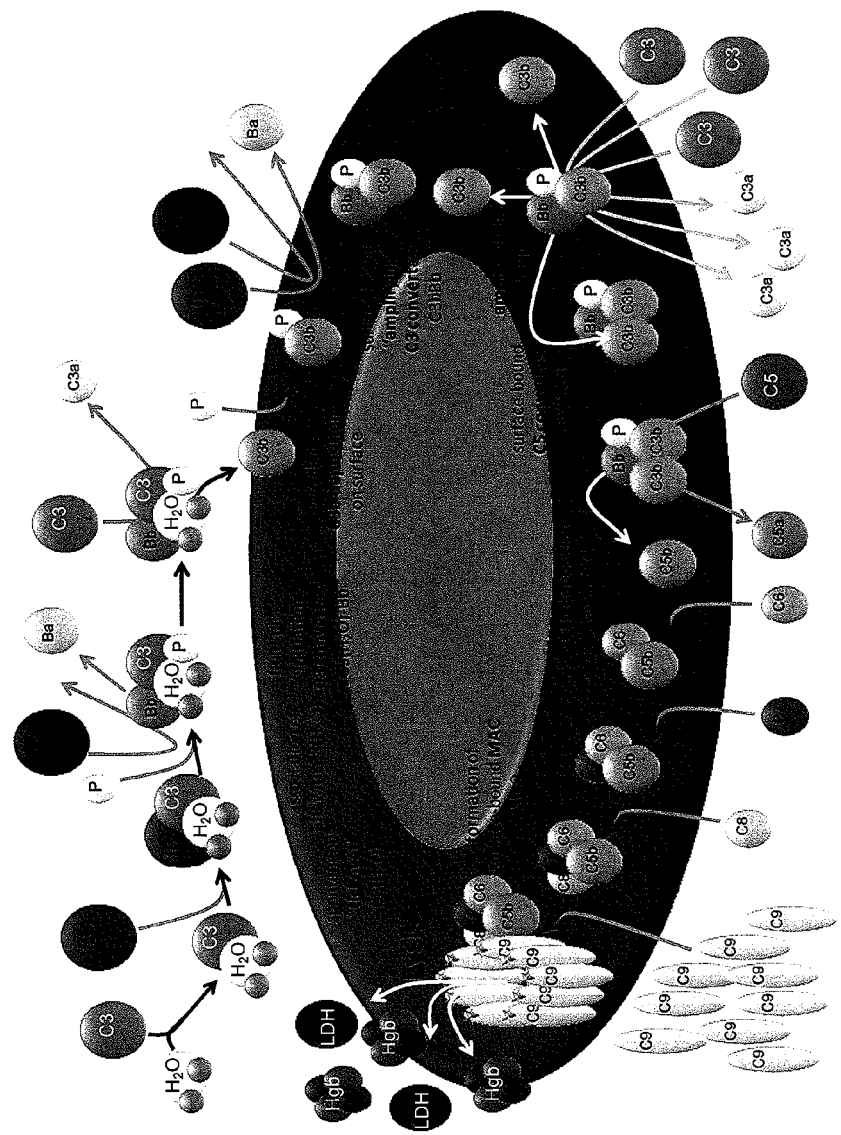
FIG. 20 illustrates the sequence of complement alternative pathway activation on a red blood cell in the absence of protection.

PNH RBCs lack the ability to control C3 convertase via CD55 and C5 convertase-mediated formation of the membrane attack complex (MAC) via CD59. In the absence of local complement alternative pathway (CAP) control (see FIG. 20), spontaneous tickover generates fluid-phase $C3(H_2O)$ that associates with factor B (fB) and properdin (P) in the presence of factor D (fD) to form the fluid-phase initiation C3 convertase, which cleaves C3 to release C3a and deposit covalently-bound C3b on the RBC surface. Association of C3b with fB and P in the presence of fD generates the surface-bound amplifying C3 convertase. The CAP amplification loop generates additional C3b and C3 convertase, and by adding C3b to C3 convertase, forms surface-bound C5 convertase. C5 convertase cleaves C5 to release C5a and deposit C5b, leading to rapid addition of C6, C7, C8 and poly-C9 to form the MAC, resulting in lysis and release of hemoglobin (Hgb) and lactate dehydrogenase (LDH).

Figure 21:
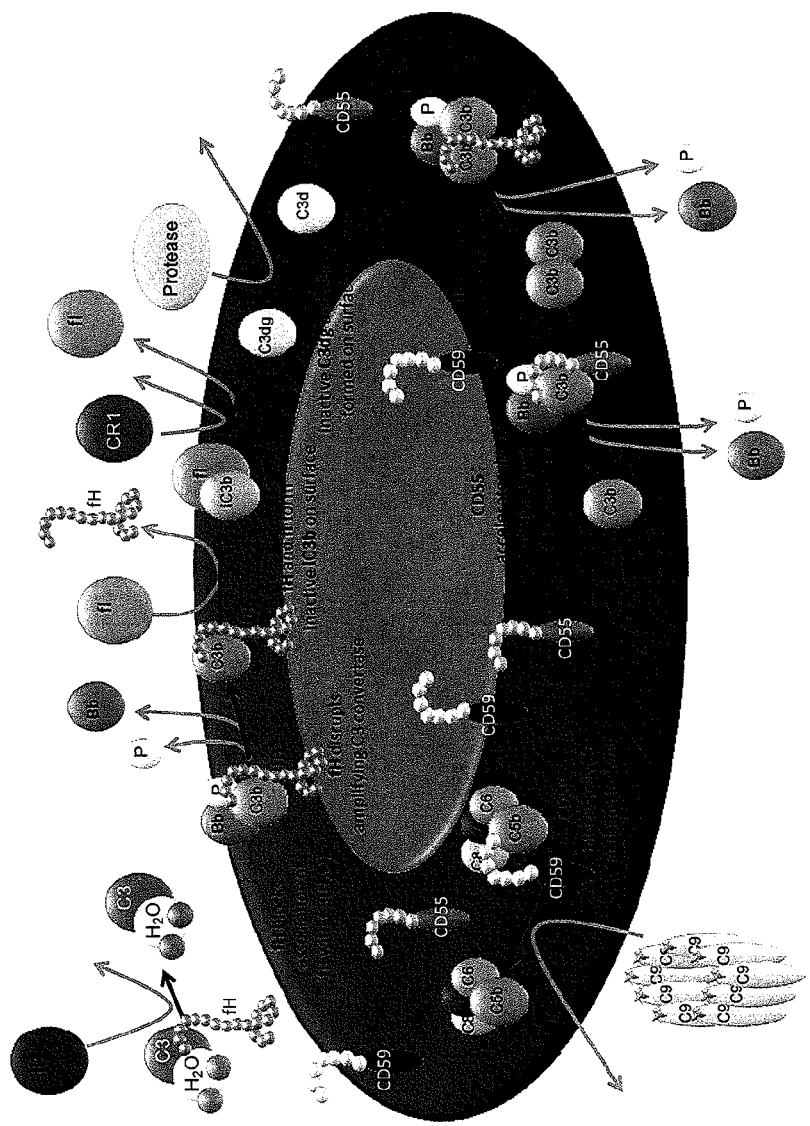
FIG. 21 illustrates the sequence of normal protection of a red blood cell from complement alternative pathway activation.

The primary negative regulator of spontaneous CAP initiation is fH. In the fluid phase, fH blocks the association of $C3(H_2O)$ with fB. On the cell surface, fH also disrupts the amplifying C3 convertase and, in association with the protease Factor I (fI), converts C3b to inactive iC3b on the cell surface, which is subsequently converted to C3dg by fI and complement receptor 1 (CR1), and then to C3d by poorly characterized serum proteases. fH also disrupts the C5 convertase. These fH activities occur on normal and PNH RBCs, but contribute only partially to the complete control of complement activation that is necessary on RBCs. Most importantly, on normal RBCs (see FIG. 21), C3 convertase undergoes accelerated decay due to CD55 (DAF), while MAC formation is disrupted by CD59 at the C9 binding steps. Thus, in the presence of normal protective mechanisms, spontaneous CAP activation is held in check. While fH activity is not compromised in PNH, in the absence of CD55 and CD59 function, fH cannot control CAP activation sufficiently on the RBC surface (see FIG. 20), and hemolysis results.

Figure 22:
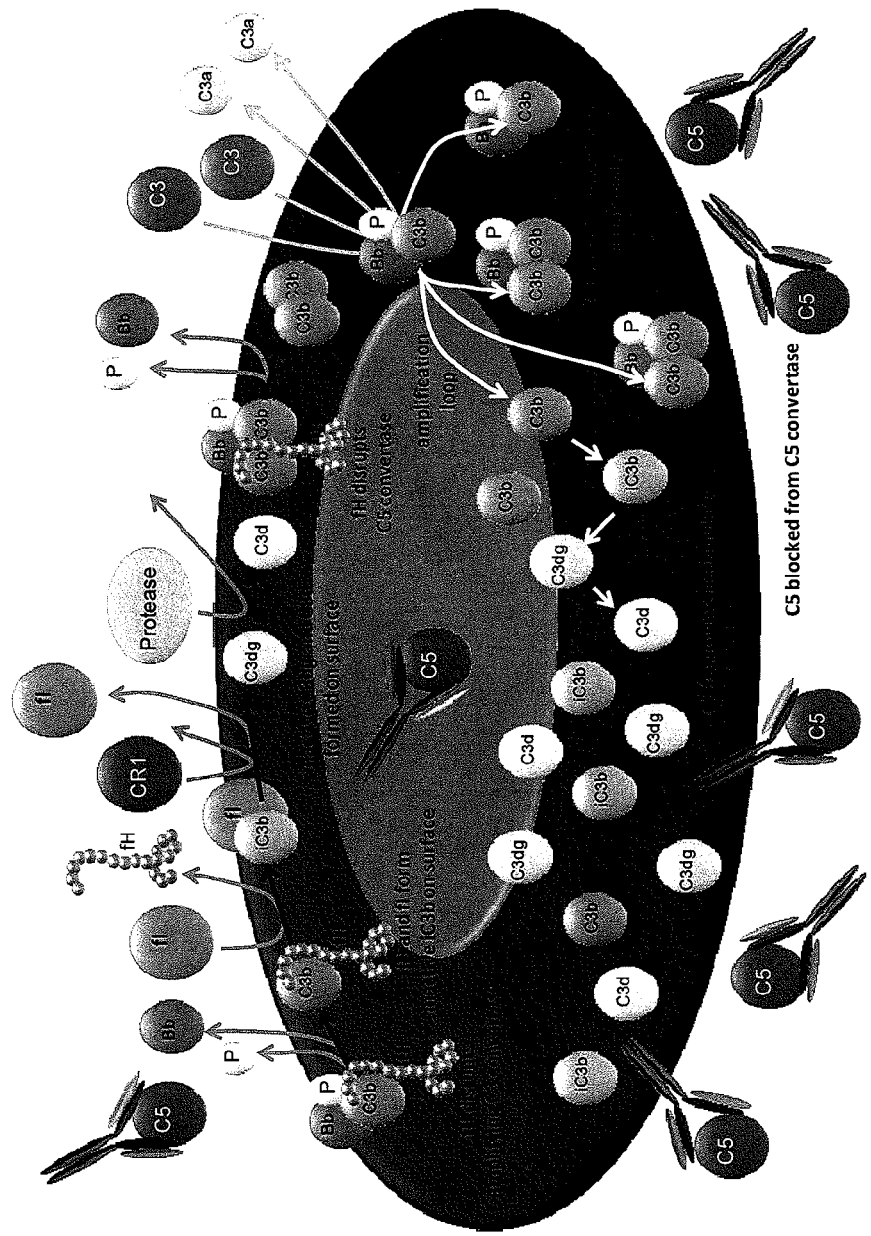
FIG. 22 illustrates the sequence of protection of a red blood cell with an anti-C5 monoclonal antibody.

One way to protect PNH RBCs from intravascular hemolysis (IVH) is to prevent formation of the MAC, which can be accomplished by blocking C5 participation with an anti-C5 monoclonal antibody, such as eculizumab (see FIG. 22). In this setting, fH function is unchanged. However, fH alone cannot prevent all amplifying C3 convertase function, so that PNH RBCs gradually become "coated" with C3 fragments. Risitano et al., Blood, 113: 4094-100 (2009). This leads to removal of these C3 fragment-coated PNH RBCs within the liver and the spleen, a process known as extravascular hemolysis (EVH). In addition to accumulating C3 fragments, continuous activity of the amplifying C3 convertase will likely result in increased formation of C3 and C5 convertases on the PNH RBC surface. This condition would render PNH RBCs vulnerable to lysis if unblocked C5 were to become available, and may explain why eculizumab is not able to prevent hemolysis of PNH RBCs in vitro. Risitano et al., Blood, 114:71 (2009; Abstract No. 158; Accessed at: http://ash.confex.com/ash/2009/webprogram/Paper19102.html).

Figure 23:
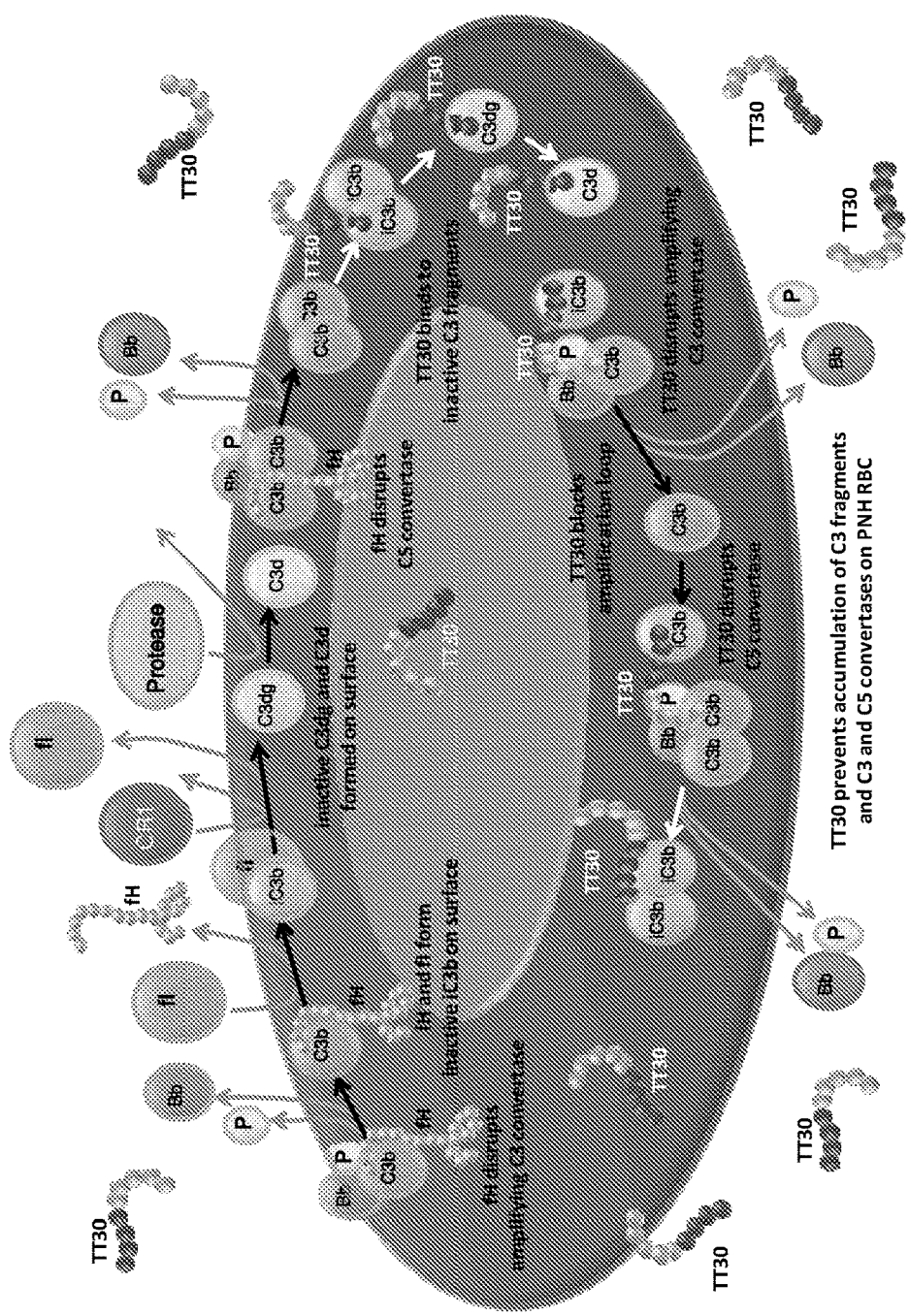
FIG. 23 illustrates the sequence of inhibition of complement alternative pathway activation on a red blood cell as achieved by the targeted CAP inhibitors of the present invention.

Without being bound by theory, it is hypothesized that TT30 (targeted fH) will bind to C3 fragments deposited on the RBC surface via spontaneous tickover, and will prevent formation of the C3 and C5 convertases and the MAC, thus preventing IVH. Prevention of hemolysis should result in a decrease in serum LDH concentrations and an increase in hematocrit. In addition, TT30 may to prevent the accumulation of C3 fragments associated with EVH (FIG. 23).

Example 2. In Vitro Model of Complement-Mediated Hemolysis of PNH RBCs; Effect of Different Complement Inhibitors PNH is a hematological disorder characterized by complement (C)-mediated intravascular hemolysis (IVH) due to a lack of C inhibitors CD55 and CD59 on affected red blood cells (RBCs). Normal, spontaneous activation of the complement alternative pathway, when uncontrolled by CD55, may lead to deposition of C3 on PNH RBCs which is not detectable in untreated PNH, generation of C3 and C5 convertases and, due to lack of CD59, to formation of the membrane attack complex (MAC) and lysis.

TT30 is a 65 kDa recombinant chimeric human fusion protein of the present invention. TT30 comprises the iC3b/C3d-binding region of C receptor 2 and the functional domains of the CAP regulator factor H (fH), which acts like CD55 to block CAP C3 convertase formation and activity on the surface of RBCs. RBCs were obtained from 5 PNH subjects (2 untreated and 3 on Ecu). Sera were obtained from the same subjects and from ABO-matched healthy subjects. Sera from PNH subjects on Ecu were collected immediately after Ecu infusion, at an estimated peak concentration of ~200 µg/mL.

The Ham acid hemolysis test is a diagnostic method to assess, in vitro, the increased susceptibility of PNH RBCs to IVH upon Complement activation after a brief incubation in acidified serum. Ham and Dingle, J. Clin. Invest., 18:657 (1939). The main principle of the Ham Test is to challenge PNH RBCs (which are, by definition, sensitive to complement activation due to the lack of CD55 and CD59) in fresh normal human sera, after in vitro activation of the complement cascade by acidification. As part of the present invention, the present inventors developed a Ham Test modified to delay hemolysis and allow serial evaluations to assess the susceptibility of PNH RBCs to the subsequent hemolysis (resulting from terminal-complement activation) and to pre-hemolytic complement activation (as assessed by initial C3 deposition in double color [C3-FITC vs CD59-PE] flow cytometry). Hemolysis was measured by classical spectrometry of the supernatant and also quantified by flow cytometry of RBCs (Ferreira and Pangburn, Blood 2007). Thus, the modified Ham Test allowed the evaluation of the effects of various C regulators on hemolysis of PNH RBCs, as well as on the initial C3 activation and deposition through the CAP.

C3-bound RBCs have been shown to develop during treatment with the terminal complement inhibitor eculizumab (Ecu) in PNH and are a possible cause of extravascular hemolysis (EVH) in these subjects (Risitano et al, Blood 2009); in this modified Ham test, C3 deposition was quantified by double color flow cytometry. The complement inhibitor TT30 (Taligen Therapeutics, Cambridge, Mass.) was evaluated. TT30 is a targeted inhibitor of C3 convertase, comprising a targeting moiety isolated from CR2 and a complement inhibiting moiety isolated from Factor H.

RBCs were obtained were obtained from PNH subjects both untreated and on eculizumab. Sera were obtained from ABO-matched healthy individuals. In brief, fresh normal sera were supplemented with MgCl, and pre-incubated with the complement inhibitor (TT30). After 15 minutes, HCl was added to acidify the sera and activate the complement cascade. PNH were added (1:20 of a 50% suspension) to sera, and incubated at 37° C. Hemolysis and C3 deposition were measured at different intervals, to assess the effect of the complement inhibitor. Details of materials and experimental methods are described below.

In this modified Ham test, delayed lysis of RBCs was observed that originated from untreated PNH subjects; lysis was partial after 1 h (50-70%), and became almost complete at 72 h. Results were expressed as survival of initial PNH RBCs: after 1, 6, 24 and 72 h, survival was ~65, 40, 20 and <10%, respectively. Hemolysis was observed at the same rate in PNH RBCs from subjects receiving Ecu, when they were incubated with ABO-matched sera. TT30 was able to significantly inhibit hemolysis of RBCs from untreated PNH subjects. TT30 demonstrated concentration and time dependent inhibition of hemolysis. TT30 concentrations of 3-100 nM (1000 nM=65 μg/ml) did not improve PNH RBC survival even at 1 h. In contrast, 300 nM TT30 resulted in temporary inhibition (surviving PNH RBCs ~70%) at 1 h, which was not sustained (surviving PNH RBCs were ~50 and 20% at 6 and 24 h). Higher concentration of TT30 (3000 nM, equal to 195 μg/mL) resulted in complete inhibition of hemolysis as long as at 24 h, though hemolysis was evident with longer incubation (surviving PNH RBCs were ~90, 90, 90 and 50% at 1, 6, 24 and 72 h, respectively).

When washed RBCs from PNH subjects on Ecu were utilized, TT30 resulted in inhibition of hemolysis as on untreated PNH RBCs. Finally, the modified Ham test to investigate the effect of complement inhibitors on C3 activation and deposition on PNH RBCs. Consistent with the mechanism of local RBC surface inhibition of C3 convertase activity, TT30 exposition did not result in any C3 deposition on PNH RBCs, throughout a 120 h incubation. In addition, when PNH RBCs from PNH subjects on Ecu were utilized, TT30 did not allow further C3 binding on PNH RBCs, even if pre-existing C3+ RBCs remained unchanged.

In this model, TT30 demonstrated concentration and time dependent inhibition of hemolysis. TT30 concentrations of 3-100 nM (1000 nM=65 μg/ml) did not improve PNH RBC survival even at 1 h. In contrast, 300 nM TT30 resulted in an substantial inhibition (surviving PNH RBCs ~70%) at 1 h, which was not sustained longer (surviving PNH RBCs were ~50 and 20% at 6 and 24 h). Higher concentrations of TT30 (3000 nM, equal to 195 μg/mL) resulted in complete inhibition of hemolysis as long as at 24 h, though hemolysis was evident with longer incubation (surviving PNH RBCs were ~90, 90, 90 and 50% at 1, 6, 24 and 72 h, respectively). A modified Ham test was conducted to investigate the effect of C inhibitors on C3 activation and deposition on PNH RBCs. Consistent with the mechanism of local RBC surface inhibition of C3 convertase activity, exposure to TT30 did not result in any C3 deposition on PNH RBCs, throughout a 120 h incubation. Our data show that modulation of the CAP using TT30 inhibits hemolysis of PNH RBCs in vitro. TT30 also inhibits the C3 activation and deposition on surviving PNH RBCs, which has been recently described as a primary cause of residual hemolysis and anemia in PNH subjects receiving the terminal complement inhibitor eculizumab. These findings provide the rationale for a potential new mechanism for treating both IVH and EVH associated with PNH by targeting and inhibiting the CAP.

In conclusion, the "modified Ham test" described herein was developed to assess in vitro the efficacy of C inhibitors on PNH RBCs. Data from this test show that modulation of the CAP using TT30 inhibit hemolysis of PNH RBCs in vitro. However, unlike Ecu, TT30 also inhibits the C3 activation and deposition on surviving PNH RBCs. These findings provide evidence of efficacy for a potential new mechanism for treating both IVH and EVH associated with PNH by targeting and inhibiting the CAP.

Materials and Experimental Methods.

Fresh sera was obtained from ABO-matched donors. Fresh red blood cells were prepared from PNH subjects, by washing thrice by NaCl 0.9%; use a 50% or 25% resuspension for experiments (1:20 and 1:10 to serum, respectively). A 50% RBC resuspension should be about $5\times10^6$ RBCs/μL.

The following solutions and reagents were prepared:

$MgCl_2$ (hexahydratate, MW 203) prepare a 100 mM stocking solution (2.03 g in distilled water 10 mL); prepare a 30 mM working solution (1:3.3 from stocking solution), to be used 1:20 to serum in final experiments.

HCl Start from available 37% solution (=12M); prepare a 1M=1N solution (8.1 mL in 100 mL of distilled water); prepare 0.4 or 0.2 working solution (to be used 1:20 and 1:10 to serum, respectively).

TT30 (MW 65 kDa)—Start from 118 μM solution (7.71 mg/mL); prepare two working solutions; 6 μM (1:20 from stocking solution); 0.6 μM (1:10 from working solution A). Use the appropriate amount according to dilution curve (final range 3-3000 nM).

Preparations were made according to TABLE 1. 500 μL (10 parts; 1 part equal to 50 μL) of serum (or water, as appropriate) was added to all tubes. 25 μL (0.5 parts) of 30 mM MgCl solution was added in the appropriate tubes. The appropriate concentration of inhibitor, as indicated in TABLE 1, was added and incubated for 15 minutes. HCl was added to acidify the serum.

TABLE 1

TUBES AND CONTENTS

| | CONDITIONS | | INHIBITOR |
|---|---|---|---|
| 1 | Water | PNH RBCs | |
| 2 | NaCl 0.9% | PNH RBCs | |
| 3 | Serum | PNH RBCs | MgCl |
| 4 | Acidified Serum | PNH RBCs | MgCl |
| 5 | Acidified Serum | PNH RBCs | MgCl TT30 3000 nM (15 μL of 120 μM) |
| 6 | Acidified Serum | PNH RBCs | MgCl TT30 1000 nM (5 μL of 120 μM) |
| 7 | Acidified Serum | PNH RBCs | MgCl TT30 300 nM (30 μL of 6 μM) |
| 8 | Acidified Serum | PNH RBCs | MgCl TT30 100 nM (10 μL of 6 μM) |
| 9 | Acidified Serum | PNH RBCs | MgCl TT30 30 nM (30 μL of 0.6 μM) |
| 10 | Acidified Serum | PNH RBCs | MgCl TT30 10 nM (10 μL of 0.6 μM) |
| 11 | Acidified Serum | PNH RBCs | MgCl TT30 3 nM (3 μL of 0.6 μM) |

50 μL (1 part) of 0.2 M HCl were added to each tube. RBC resuspension was added to all tubes, as 25 μL (0.5 parts) of 50% RBC suspension, about $5\times10^6$/uL; 25 uL of 50% RBC suspension for each tube) was used. The tubes were incubated at 37° C. (for at least 72 h). Check for hemolysis and C3 coating (at 1 h, 6 h, 24 h and 72 h): RBC pellet by CD59/C3 flow cytometry staining.

1 μL of RBC pellet (about $10^7$ RBCs) was diluted 1:1000; 50 uL of a $10^4$/uL*RBC resuspension in NaCl was incubated with 1 uL of the anti-C3 polyclonal antibody and 5 uL of the anti-CD59 monoclonal antibody. Samples were incubated 1 h at room temperature; and analyzed by flow cytometry after addition of 250-500 uL of NaCl, without additional washing (Risitano et al, Blood 113:4094-4100 (2009)).

Survival of PNH RBCs was calculated as follows: (Ferreira and Pangburn, Blood, 110:2190-2192 (2007)): % survival=(% PNH post/% N post)×(% N pre/% PNH pre)

Lysis of PNH RBCs was calculated as follows: % lysis=100−(% survival).

Example 2A: In Vitro Model of Complement-Mediated Hemolysis of PNH RBCs; Effect of Different Complement Inhibitors An in vitro model was developed to allow evaluation of the comparative efficacy of TT30 and eculizumab. This in vitro model is a modified Ham test, in which PNH RBCs are exposed to ABO-matched acidified normal serum (ANS), which results in spontaneous CAP activation (Pascariello et al., *European Hematologic Association* (*EHA*), Barcelona, Jun. 10-13, (2010)). When PNH RBCs from untreated patients were incubated with ANS for 24 hours, 74±16% of the PNH RBCs were lysed, with RBC ghosts staining for the presence of C3 fragments (C3frag). In contrast, incubation with 1 or 3 µM (65 or 195 µg/ml) TT30 resulted in hemolysis of only 14±26% or 5±7% of the PNH RBCs and surviving PNH RBCs were C3frag-negative on their surface. Equimolar concentrations of human fH produced much less inhibition of hemolysis (about 50% lysis), supporting the notion that TT30 is cell-targeted. The targeted fH supplementation by TT30 was confirmed by demonstration of bound TT30 on PNH RBC surface, using an anti-fH mAb by flow cytometry. Thus, TT30 prevented hemolysis representative of that observed with IVH, as well as C3frag accumulation as occurs with EVH in eculizumab-treated PNH patients.

The efficacy of TT30 has been directly compared to that of eculizumab in this model (Risitano et al., *Biologics: Targets & Therapy*, 2: 205-22 (2008), Risitano et al., *Blood*, 113: 4094-100 (2009)). PNH RBCs were obtained from 5 PNH patients (2 untreated and 3 on eculizumab); sera were obtained from the same patients and from ABO-matched healthy subjects. Sera from PNH patients on eculizumab were collected immediately after eculizumab infusion, at an estimated peak concentration of ~200 µg/mL. TT30 was spiked into serum to final concentrations ranging from 0.195 to 195 µg/mL (0.003 to 3 µM). PNH RBCs were incubated in sera, with or without eculizumab or TT30, and evaluated at various timepoints.

Figure 31:
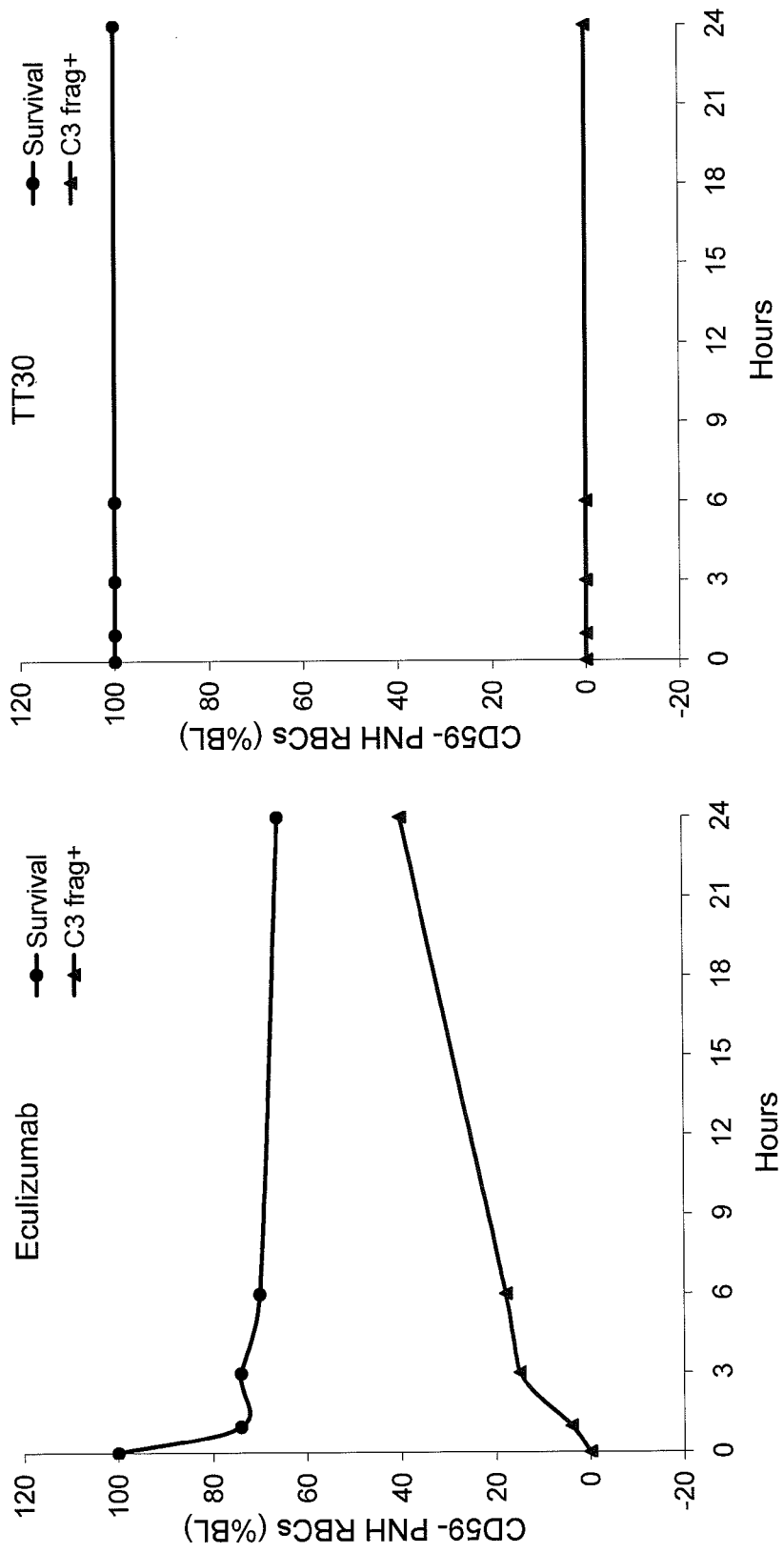
FIG. 31 shows the comparison of C3 fragment accumulation and survival of CD59− PNH RBCs incubated with eculizumab or TTT30 in an in vitro hemolysis assay. The percentage of CD59− PNH RBCs surviving and becoming coated with C3 fragments (C3frag+) when incubated in serum from a patient treated with eculizumab (left; estimated concentration ~200 µg/mL) or serum spiked with TT30 (right; 195 µg/mL) are depicted.

After 1 hour, up to ~70% of PNH RBCs were lysed by ABO-matched serum. Eculizumab significantly reduced hemolysis (to only ~25% at 1 hour), but could not provide complete protection and was associated with the progressive accumulation of C3frag+ PNH RBCs (FIG. 31). In PNH patients, the recommended minimum plasma eculizumab concentration to be maintained for prevention of hemolysis is 35 µg/mL (Risitano et al., *Biologics: Targets & Therapy*, 2: 205-22 (2008)). Therefore, this in vitro hemolysis assay may overestimate the effective concentrations for prevention of hemolysis in PNH.

TT30 prevented hemolysis of PNH RBCs in a concentration-dependent manner. Complete (~100%) inhibition of hemolysis was achieved at 65 µg/mL. At 195 µg/mL, TT30 completely prevented C3 fragment accumulation and hemolysis through 24 hours (FIG. 31). The effect of TT30 on PNH RBC survival across a range of concentrations was evaluated at each timepoint (FIG. 32) and $IC_{10}$ and $IC_{90}$ values were calculated (Table 1A). After incubation for 1 hour, the $IC_{10}$ and $IC_{90}$ values for inhibition of CAP-mediated hemolysis of PNH RBCs were 4.3 and 87.9 µg/mL, respectively.

TABLE 1A $IC_{10}$ and $IC_{90}$ Values for TT30 Inhibition of CAP-mediated Hemolysis of $CD59^-$ PNH RBCs in an In Vitro Hemolysis Assay

| Time (hr) | $IC_{10}$ (µg/mL) | $IC_{90}$ (µg/mL) |
| --- | --- | --- |
| 1 | 4.3 | 87.9 |
| 3 | 5.9 | 57.5 |
| 6 | 11.4 | 30.3 |
| 24 | 16.5 | 55.9 |

Figure 32:
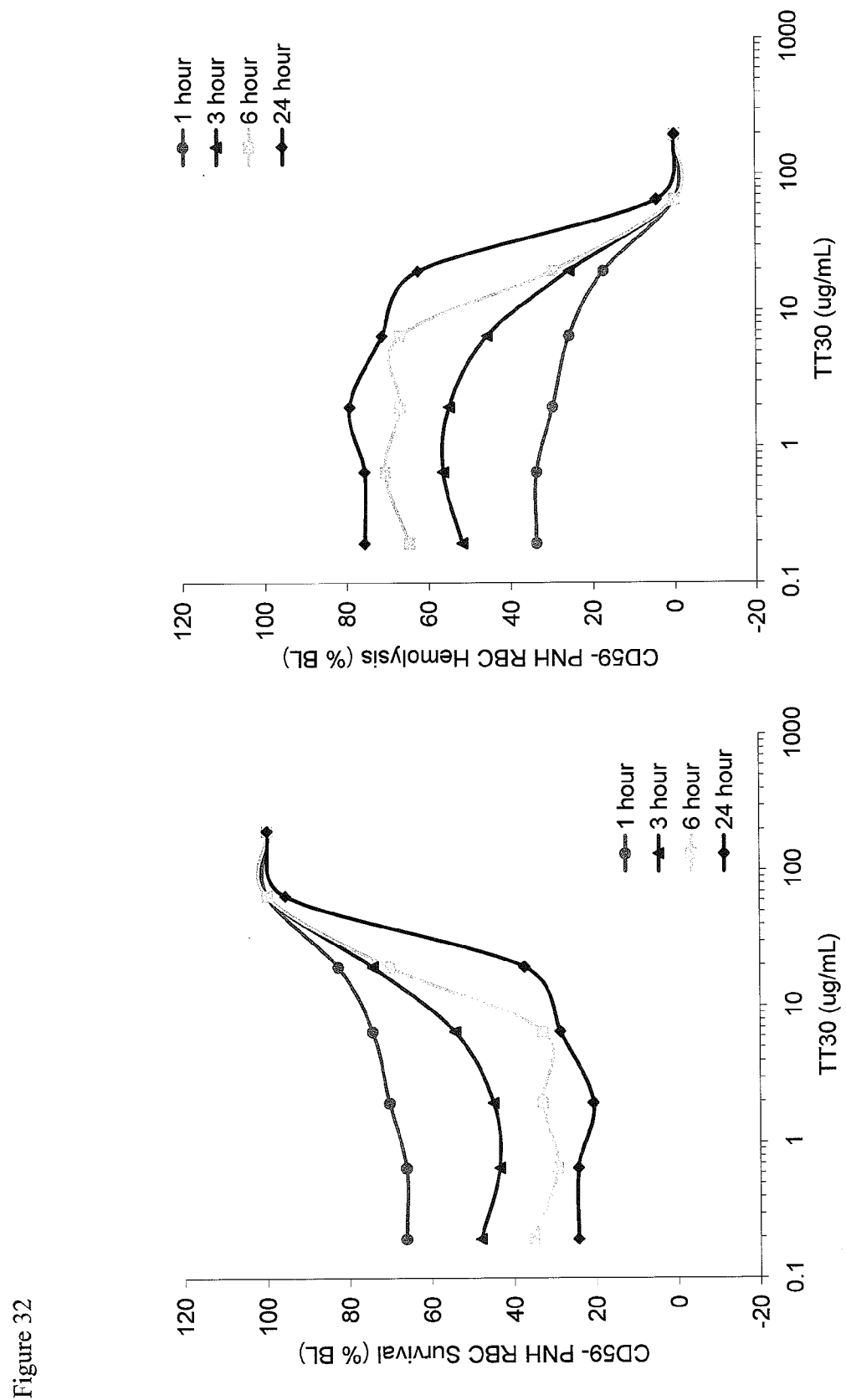
FIG. 32 shows the effect of TT30 on CD59− PNH RBC survival or hemolysis in an in vitro hemolysis assay. The percentage of CD59− PNH RBCs surviving (left) or undergoing hemolysis (right) after incubation for various times at TT30 concentrations ranging from 0.195 to 195 µg/mL are depicted. Data were from a single individual but are representative of results for multiple individuals.

$IC_{10}$ and $IC_{90}$ values calculated using data illustrated in FIG. 32.

In addition, when C3frag+ PNH RBCs from PNH patients on eculizumab were utilized, TT30 did not allow further C3frag accumulation and TT30 could be demonstrated to be bound to the surface of these protected PNH RBCs. These results suggest that modulation of the CAP with TT30 is more effective than inhibition of C5 with eculizumab at preventing hemolysis of PNH RBCs, and that, unlike eculizumab, TT30 also inhibits the C3 activation and deposition on surviving PNH RBCs. It is thus hypothesized that the in vitro hemolysis of RBCs from PNH patients on eculizumab despite the presence of protective concentrations of eculizumab may be related to increased susceptibility to lysis of C3frag+ RBCs. An alternative explanation might be that, in addition to being coated with C3frag, the PNH RBCs become coated by C3 and C5 convertases and that some small amount of C5 is released by eculizumab and cleaved by the C5 convertases, leading to MAC formation and lysis.

Example 3: Biological Mechanism of Residual Anemia in PNH Subjects Treated with Anti-05 Antibodies The following experiment was conducted to investigate the biological mechanisms underlying residual anemia in some PNH subjects on eculizumab, looking for a possible role of the early steps of the complement cascade. The results have been published in Risitano et al., Blood, 113: 4094-4100 (2009), the disclosure of which is hereby incorporated herein by reference.

A total of 56 PNH subjects were examined. Of these, 41 had previously received eculizumab treatment; and 15 did not receive eculizumab treatment. All subjects receiving eculizamab were treated according to a standard procedure: (900 mg every 14±2 days, after a loading phase of 600 mg every 7±1 days for 4 doses). Thirteen subjects were analyzed before and during treatment. Ten healthy volunteers were examined as negative controls; and 5 subjects with cold agglutinin disease (CAD) were examined as positive controls.

Figure 2:
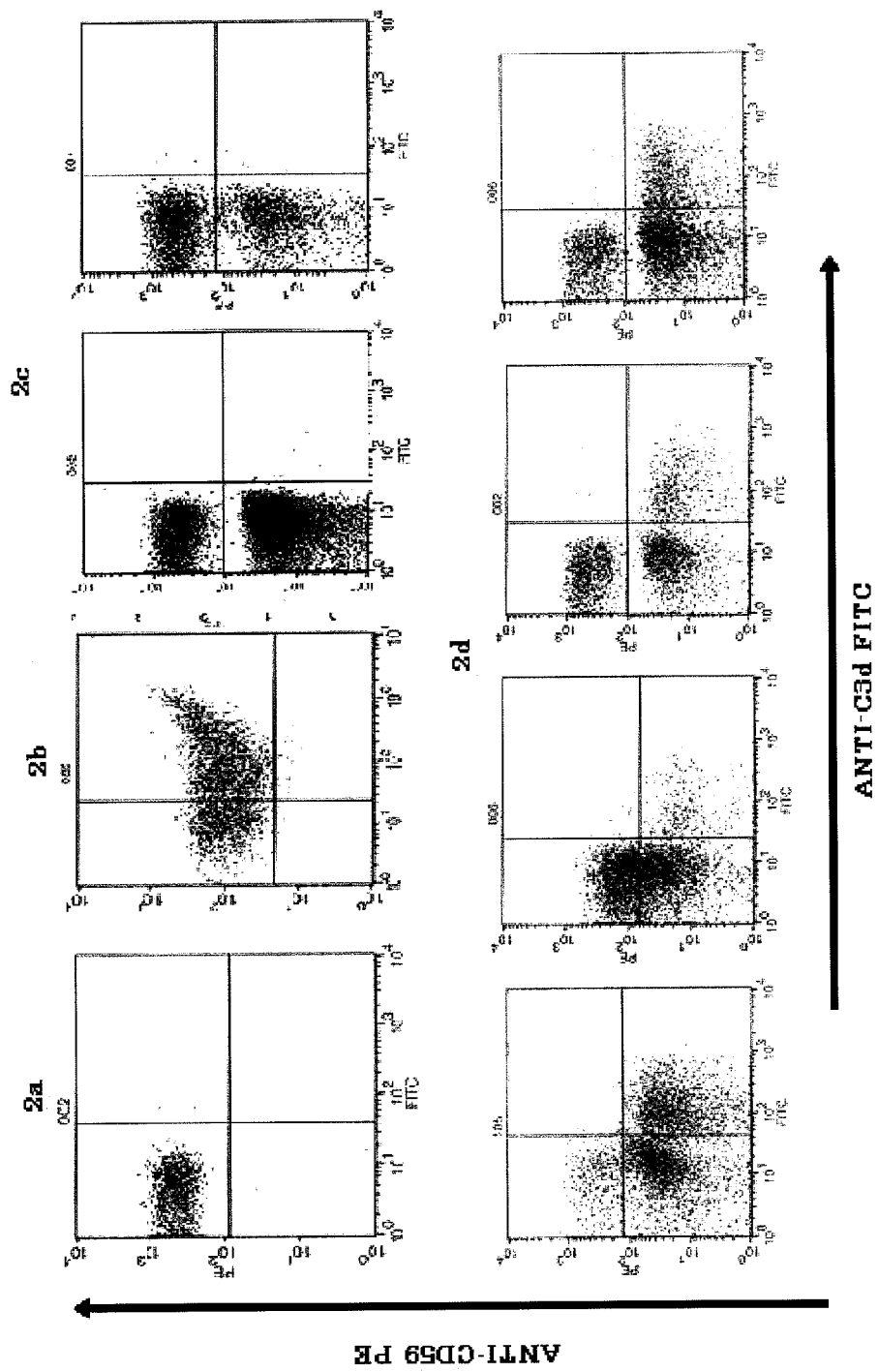
FIG. 2 illustrates the results of double color flow cytometry measuring C3 binding on RBCs in PNH subjects who have previously been treated with eculizumab. Along the Y axis are plotted the number of red blood cells which are CD59+ [normal]; or CD59− [PNH]. Along the X axis are plotted the number of cells which are C3+ [coated with C3]; or C3− [uncoated]. The upper left quadrant represents CD59+/C3− cells, i.e., normal red blood cells. The upper right quadrant represents CD59+/C3+ cells, i.e., normal red blood cells coated by C3. The lower left quadrant represents CD59−/C3− cells, i.e., PNH red blood cells, uncoated by C3. The lower right quadrant represents CD59−/C3+ cells; i.e., PNH red blood cells coated by C3.
Figure 3:
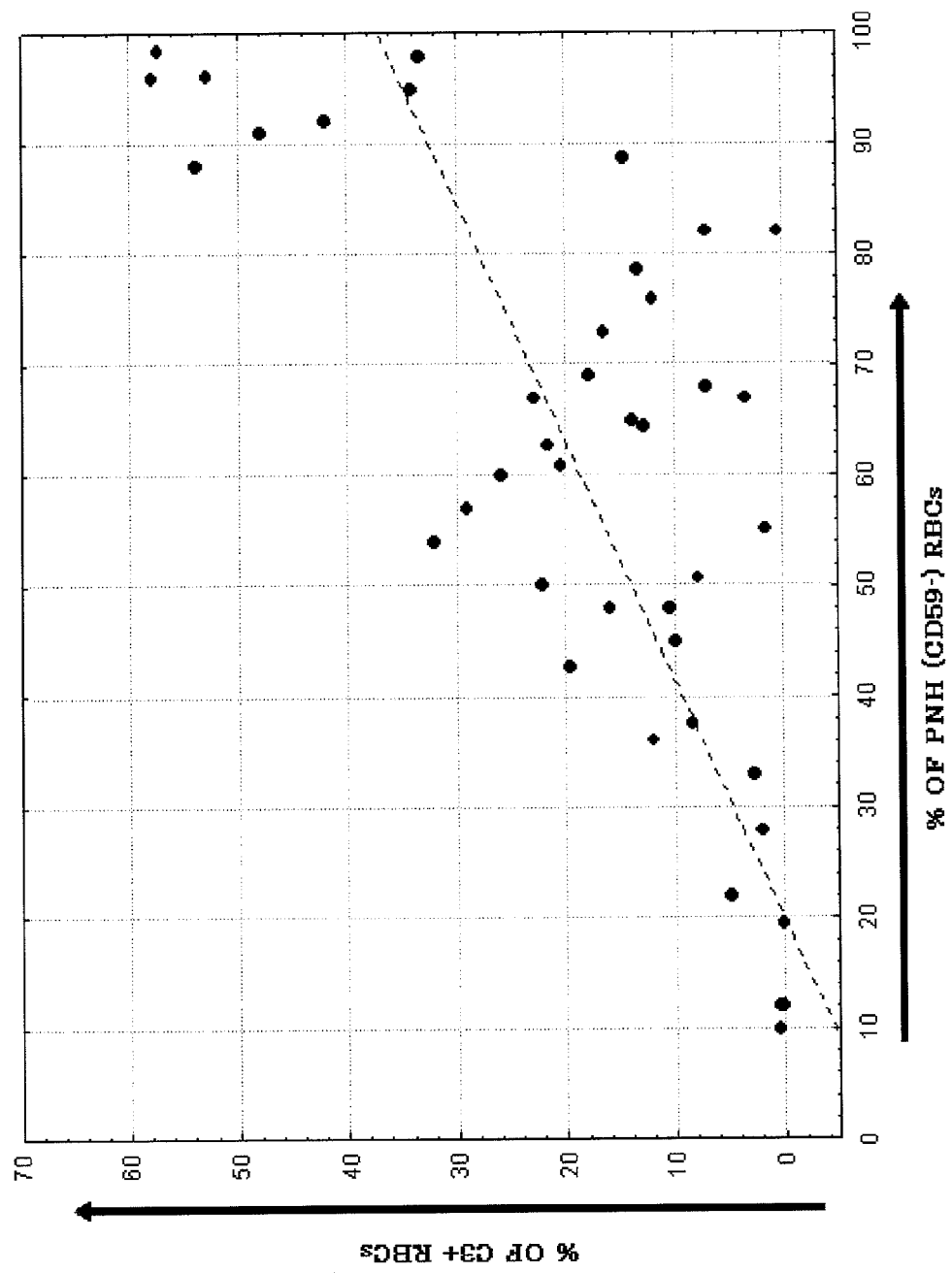
FIG. 3 illustrates the correlation of C3 binding on red blood cells in PNH subjects (Y axis), and the percent of total RBCs which are PNH (CD59−)(X axis). It can be noted that the percent of C3-coated RBCs correlates with the PNH RBC population size.
Figure 4:
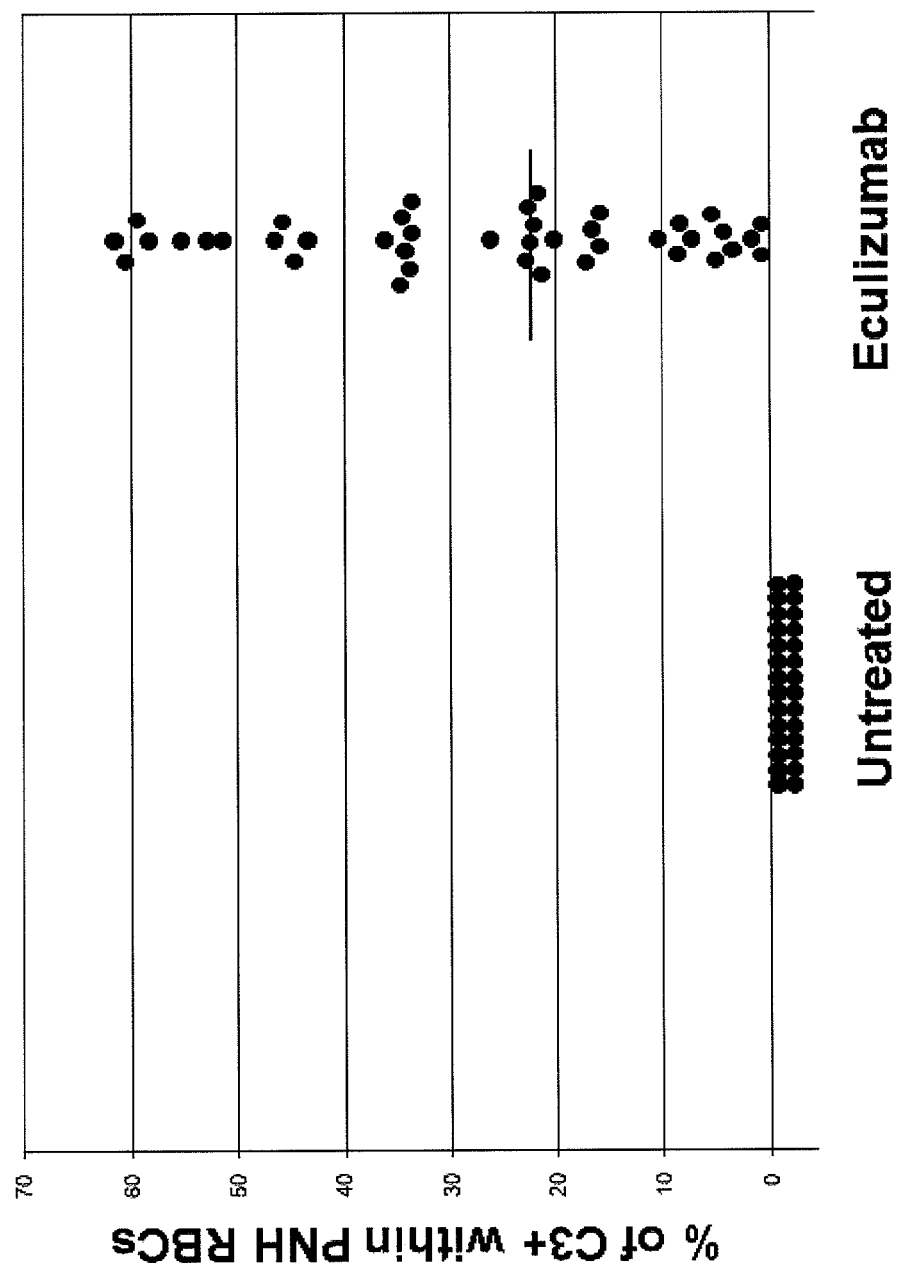
FIG. 4 illustrates the percentage of C3+ RBCs within the PNH population in patients who either have not been treated, or have been previously treated with Ecu. It can be noted that C3 is bound on PNH RBCs only in those subjects receiving the terminal complement inhibitor eculizumab, an antibody to C5, with broad heterogeneity among such subjects.

As shown in TABLE 2, decoration of red blood cells with C3d was observed in 8 out of 8 subjects after treatment with anti-C5 antibody when evaluated in a Direct Antiglobulin Test. Further, as shown in FIG. 4, while untreated subjects did not exhibit C3 fragment binding within PNH red blood cells, subjects treated with anti-C5 antibody showed broad heterogeneity with respect to the percent age of C3+ red blood cells within the PNH population. As shown in FIG. 2A, C3 fragment binding appears a few weeks after starting anti-C5 antibody treatment and remains largely stable over a long term period of two years.

TABLE 2

C3 BINDING ON RBCs IN PNH SUBJECTS ON ANTI-C5 ANTIBODY (DIRECT ANTIGLOBULIN TEST)

| Subject | Pre-Treatment | During Treatment |
|---|---|---|
| 1 | − | + |
| 2 | − | + |
| 3 | − | + |
| 4 | − | +/− |
| 5 | − | +/− |
| 6 | + (IgG)* | +/− |
| 7 | − | + |
| 8 | − | +/− |

*= Polytransfused; ANA + ve
+/− = Mixed Fields

For the purpose of the study, hematological improvement in subjects having taken Eculizamab was classified according to the categories listed in TABLE 3:

TABLE 3

CLINICAL RESPONSE TO ANTI-C5 ANTIBODY

| CLASS | CRITERIA | NUMBER |
|---|---|---|
| Optimal Responders | Transfusion independence, Hb stably >11 | N = 15 (37%) |
| Major Responders | Transfusion independence, Hb stably >8 | N = 18 (44%) |
| Partial Responders | Reduction >50% of transfusion need | N = 5 (12%) |
| Minor Responders | Transfusion need reduced <50% or unchanged* | N = 3 (7%) |

*= likely due to associated aplastic anemia

Figure 6:
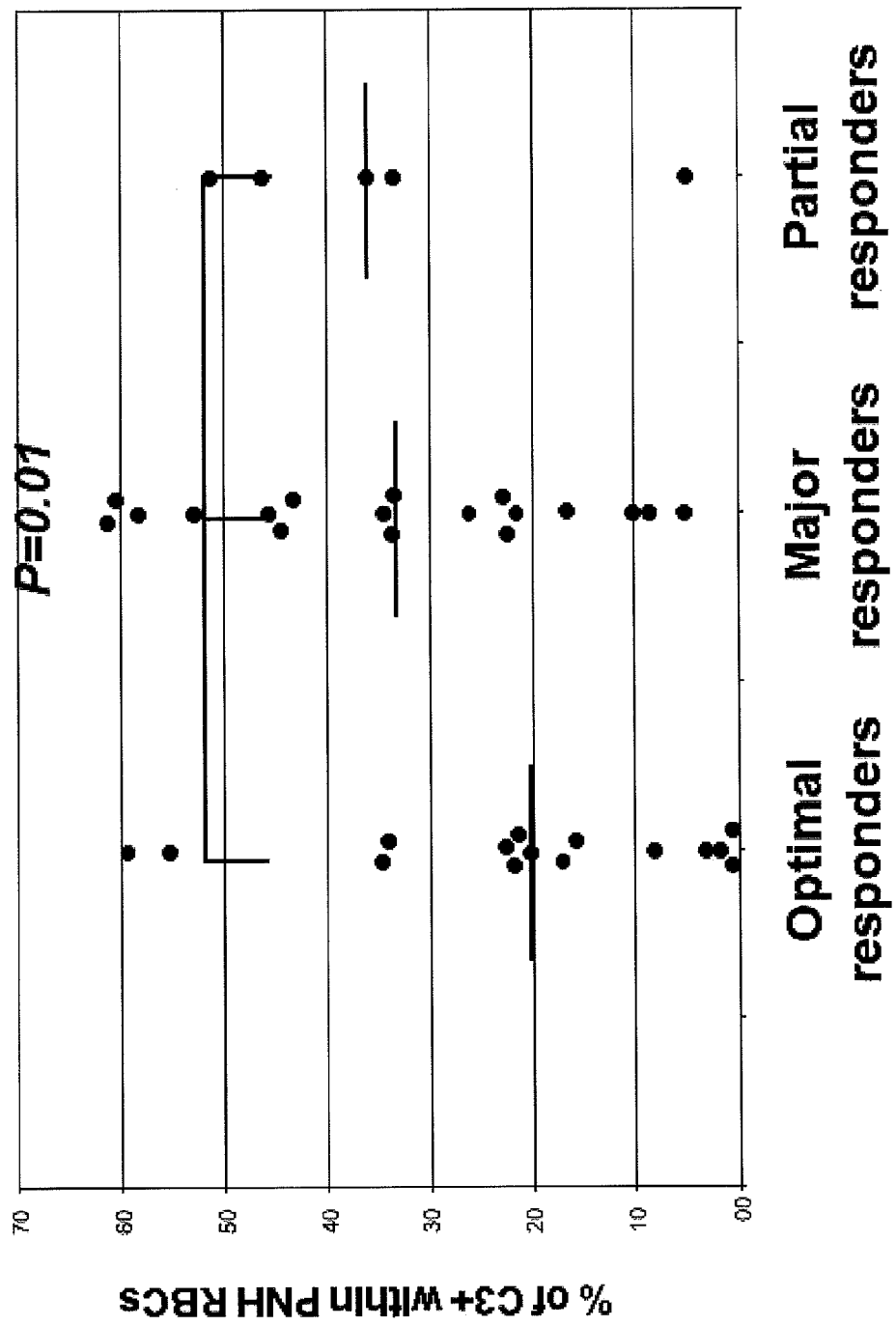
FIG. 6 illustrates the correlation of C3 binding on PNH RBCs with the hematological response of the PNH subjects who have previously been treated with the terminal complement inhibitor eculizumab, an antibody to C5. It can be noted that subjects who achieved the best hematological response to eculizumab have less C3-bound RBCs.

As shown in FIG. 6, C3 binding on PNH RBCs exhibited a strong correlation with hematological response. Subjects achieving the best hematological response had lower percentages of C3-bound red blood cells.

Supported by the data in this application, including in vivo RBC survival, the inventors theorized that this hemolysis in subjects treated with anti-C5 antibody is the result of C3-mediated extravascular hemolysis (EVH). This C3 binding is restricted to C59 negative red blood cells. The C3 binding is largely due to C3 convertase activation, an early phase of the complement cascade, which is not affected by anti-C5 antibody and remains uncontrolled given the lack of CD55 on PNH cells. The extent of C3 binding is higher in subjects not achieving an optimal hematological response and correlates with measures of ongoing hemolysis, such as reticulocyte count. Some paradigmatic subjects with a high percentage of C3-coated RBCs showed decreased RBC half-life by in vivo 51-Cr survival study, with excess counts on spleen and liver The presence of C3-mediated residual extravascular hemolysis is consistent with the observation of persistent reticulocytosis and raised unconjugated bilirubin in most PNH subjects on eculizumab (with normal LDH). Low-level extravascular hemolysis may be the rule rather than the exception in PNH subjects treated with anti-C5 antibody. It is not clear whether this is activated by anti-C5 antibody, or if it existed prior to treatment. However, prior to treatment, this phenomenon was subclinical and difficult to detect in the absence of C5-blockade. The reasons why such novel mechanism of disease has variable clinical consequences in different subjects are not fully understood, and are currently under investigation.

Figure 7:
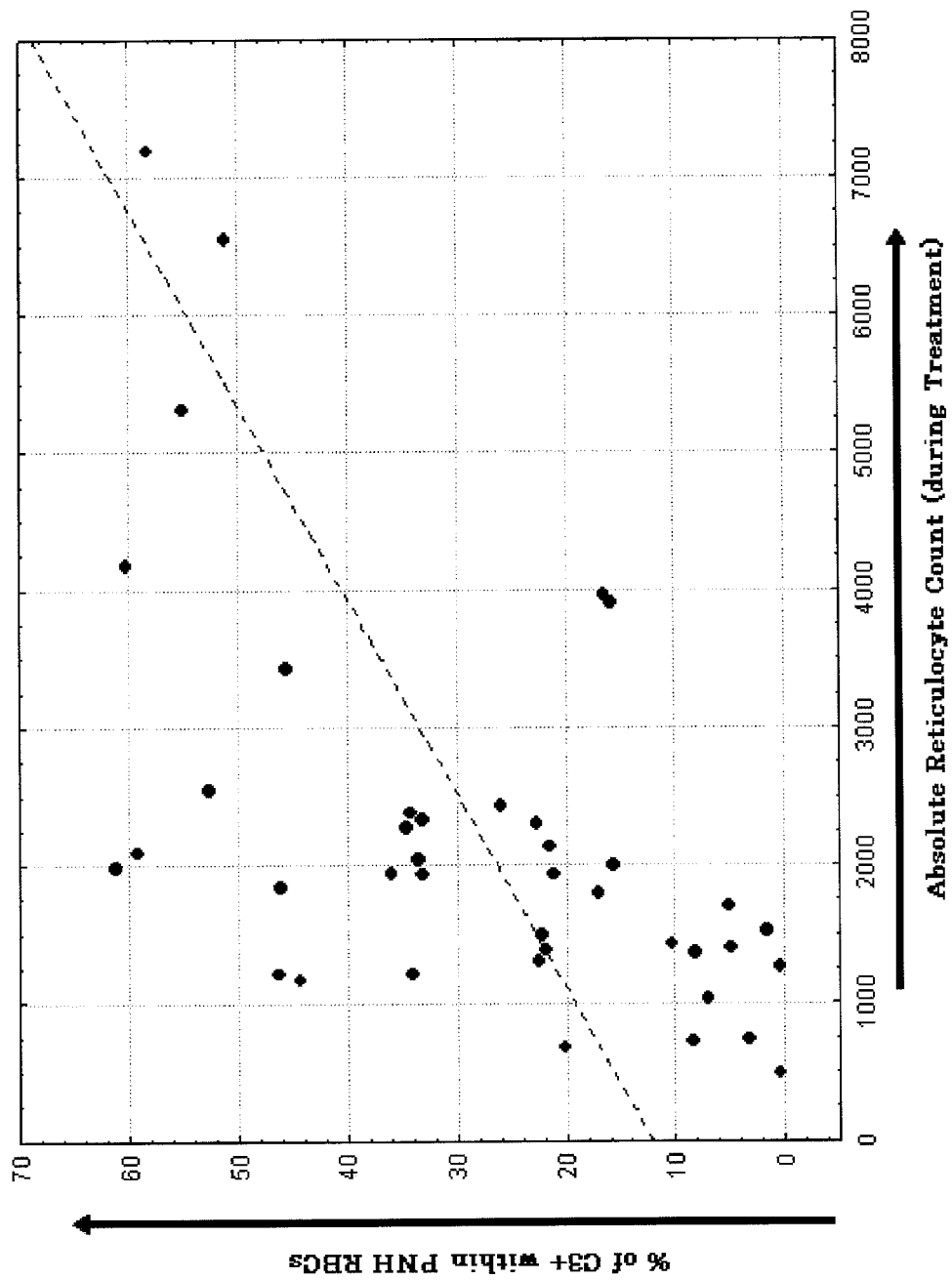
FIG. 7 illustrates the correlation of C3 binding on PNH RBCs (Y axis) with absolute reticulocyte count (ARC)(X axis). It can be noted that C3 binding correlates with measures of persisting hemolysis, such as ARC, but not with LDH. Accordingly, it is theorized that the persisting hemolysis is in significant part due to complement-mediated extravascular hemolysis, and therefore is largely unaffected by the terminal complement inhibitor.

The percentage of C3+ binding was found to increase with the absolute reticulocyte count (ARC) during treatment with terminal complement inhibitor. FIG. 7 illustrates the correlation of C3 binding on PNH RBCs with measures of ongoing hemolysis, such as ARC, but not with LDH. This correlation is consistent with the hypothesis that the C3+ binding relates to continued extravascular hemolysis in subjects treated with terminal complement inhibitors.

Figure 8:
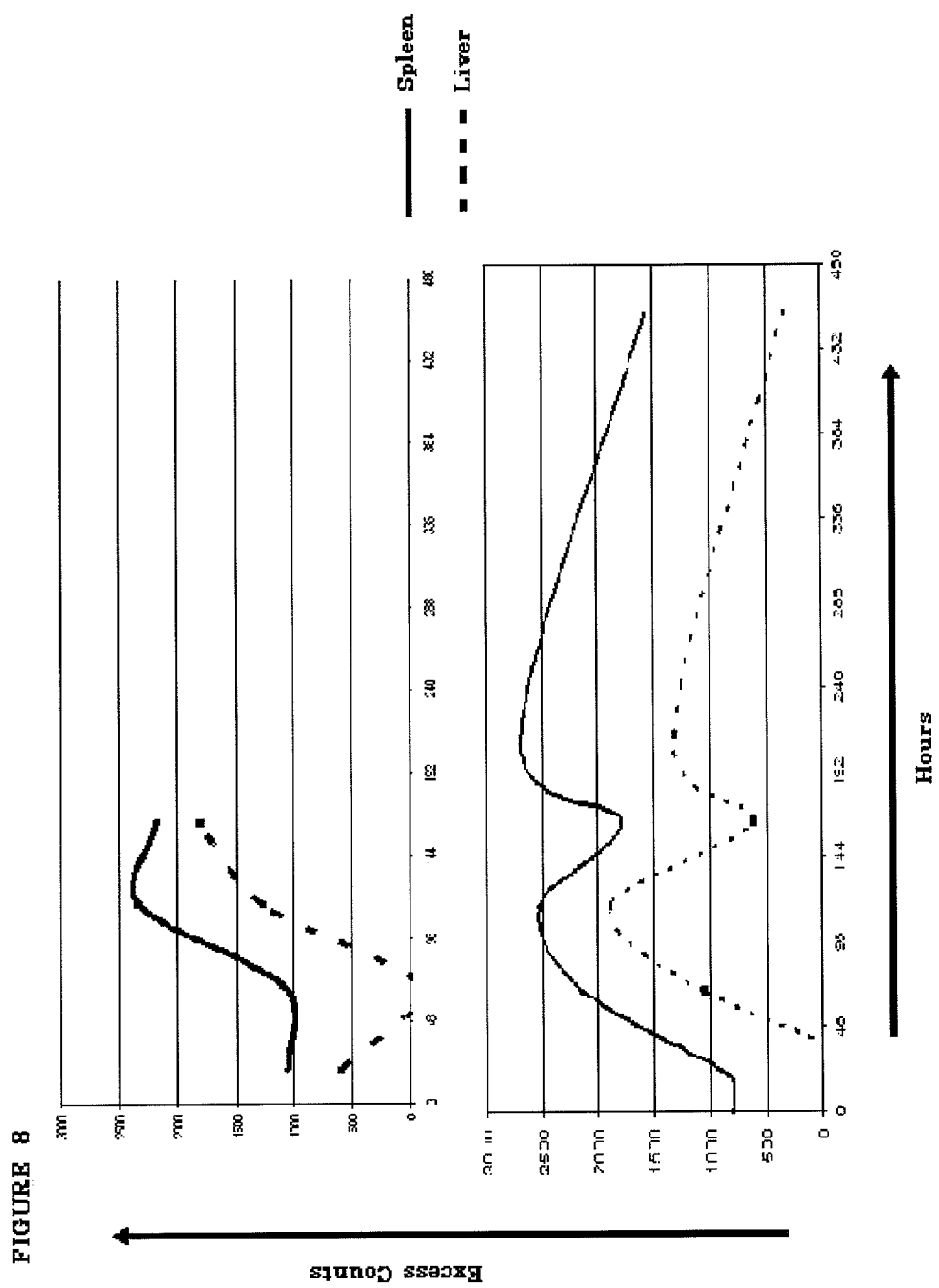
FIG. 8 illustrates the in vivo survival of 51Cr labeled red blood cells and their uptake in spleen (solid line) and liver (dotted line) from two subjects. In the first subject (FIG. 8a), measurements were taken for seven days. In the second subject, measurements were taken for twenty days (FIG. 8b). Excess counts refers to excess over control. It should also be noted that increased entrapment of RBCs in spleen and liver was detected in all subjects studied.
Figure 9:
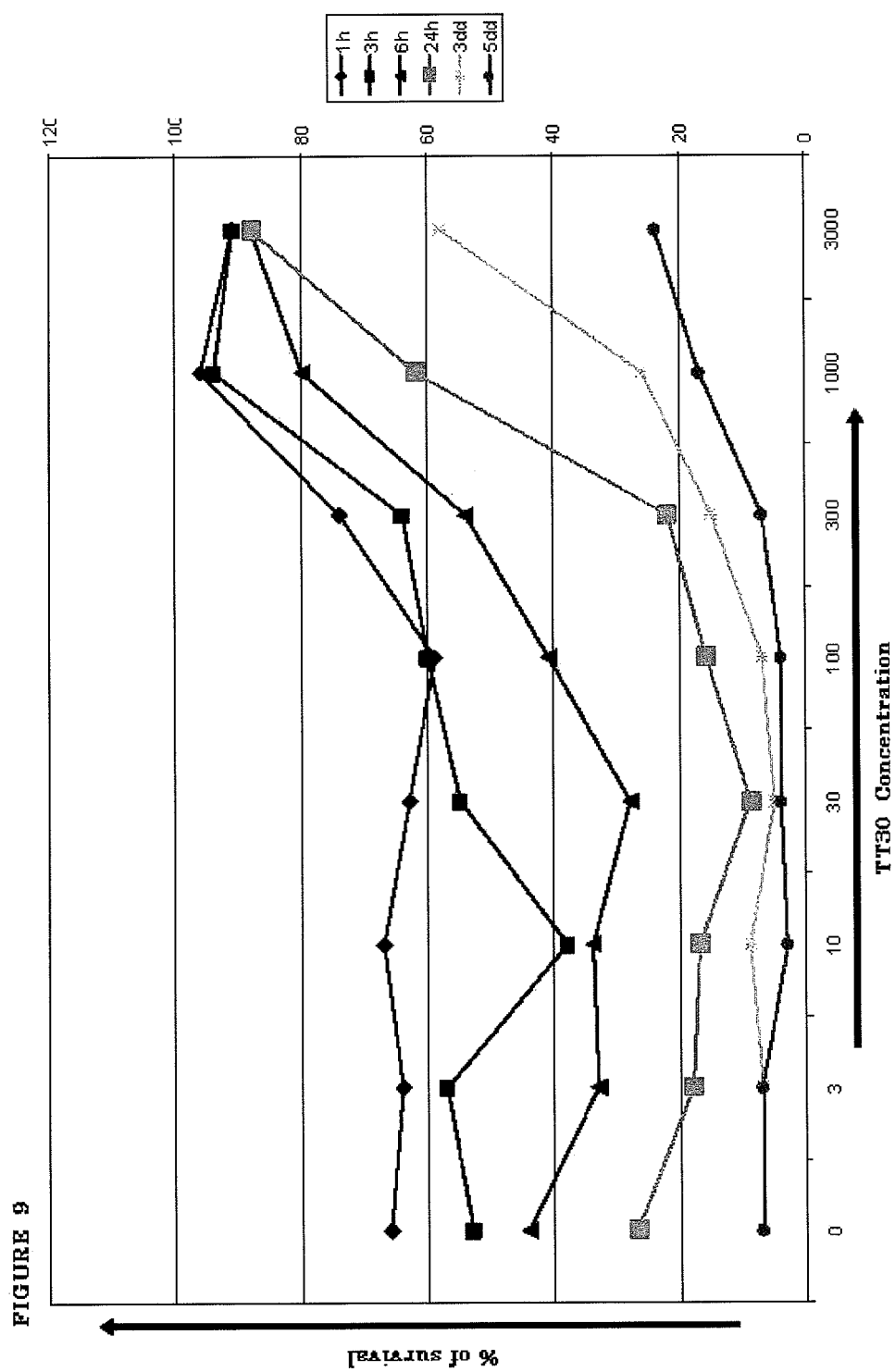
FIG. 9 illustrates the complement-mediated hemolysis of PNH RBCs from a previously untreated subject, and in particular the survival of PNH RBCs treated with various concentrations of TT30, a potent inhibitor of C3 convertase. Data represent the percent of RBCs surviving at various time points versus the concentration of TT30 administered. It can be noted that there is greater survival of PNH RBCs with higher doses of TT30.
Figure 10:
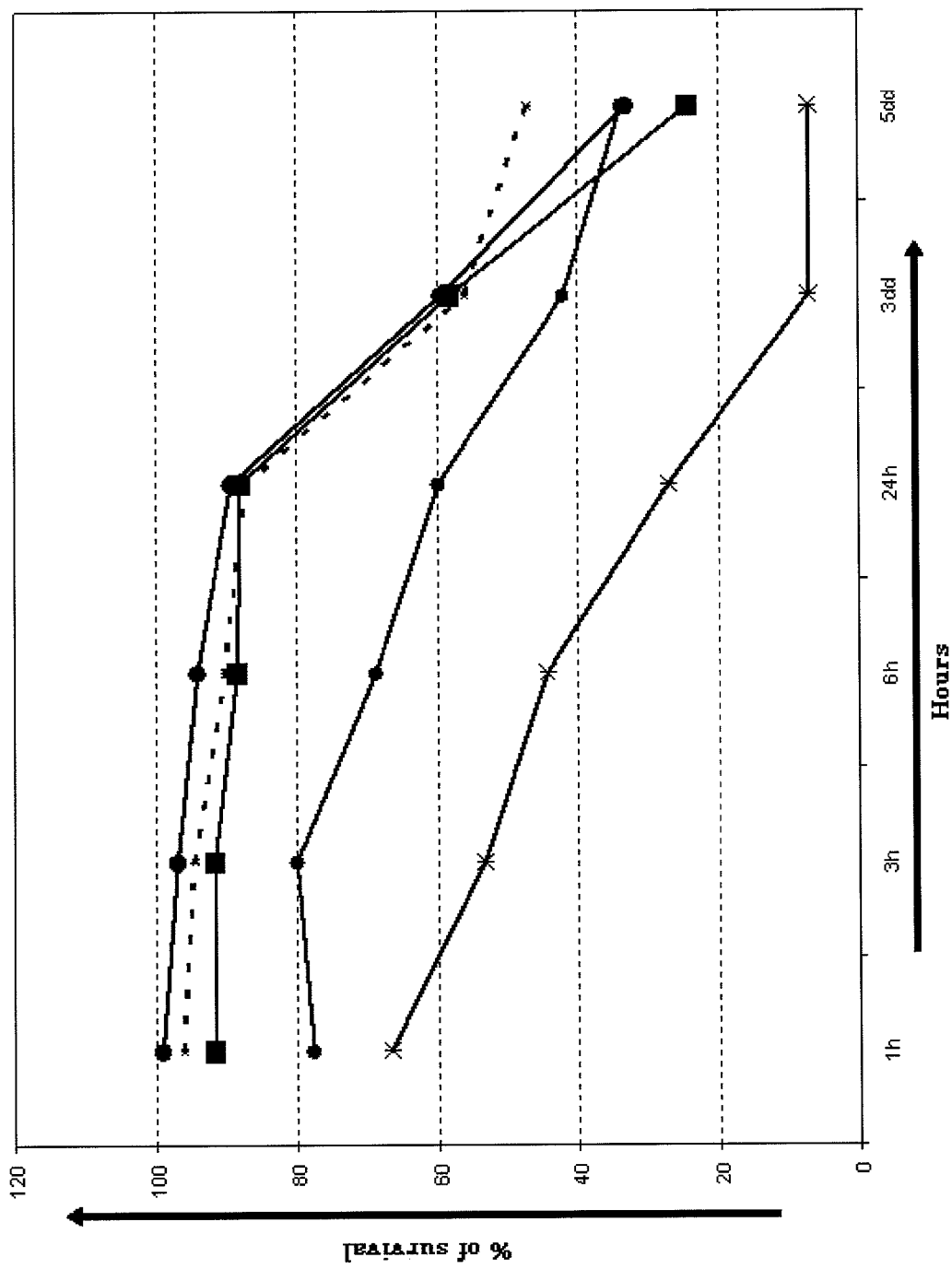
FIG. 10 illustrates the survival of PNH RBCs from a previously untreated subject, with various treatments over the course of five days. Data represents the percent of PNH RBCs surviving in cells treated with acidified serum+magnesium (AcS+Mg) (a) with no inhibitors; (b) with TT30 (TT) at 3000 nM; and (c) with TT30 (TT) at 4500 nM.
Figure 11:
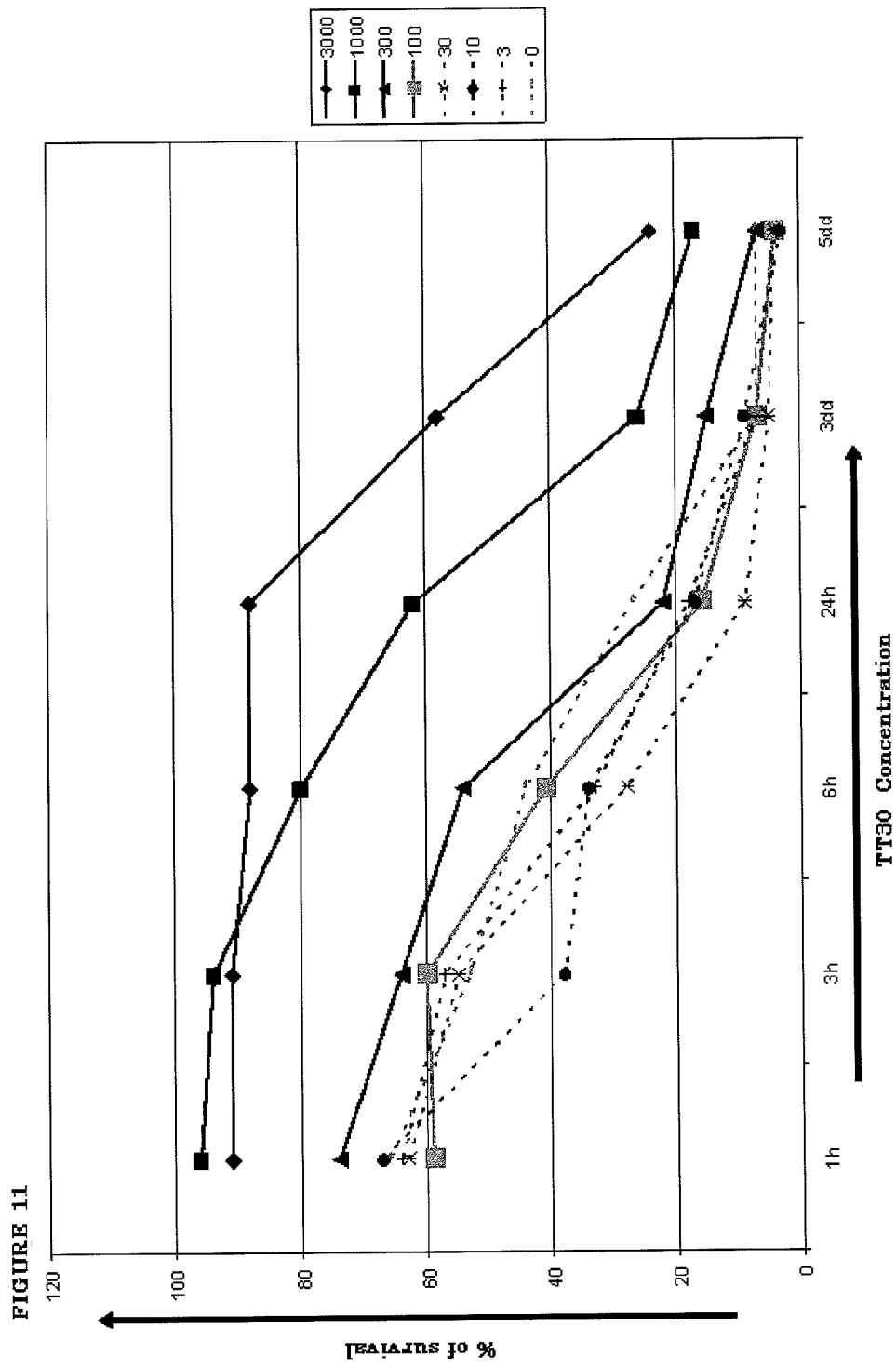
FIG. 11 illustrates the survival of PNH RBCs from a previously untreated subject, for treatment with various concentrations of TT30 over 5 days. Data represents the percent of surviving PNH RBCs with various concentrations of TT30 vs time of treatment. It can be noted that the percent of surviving PNH RBCs increases with higher doses of TT30.
Figure 12:
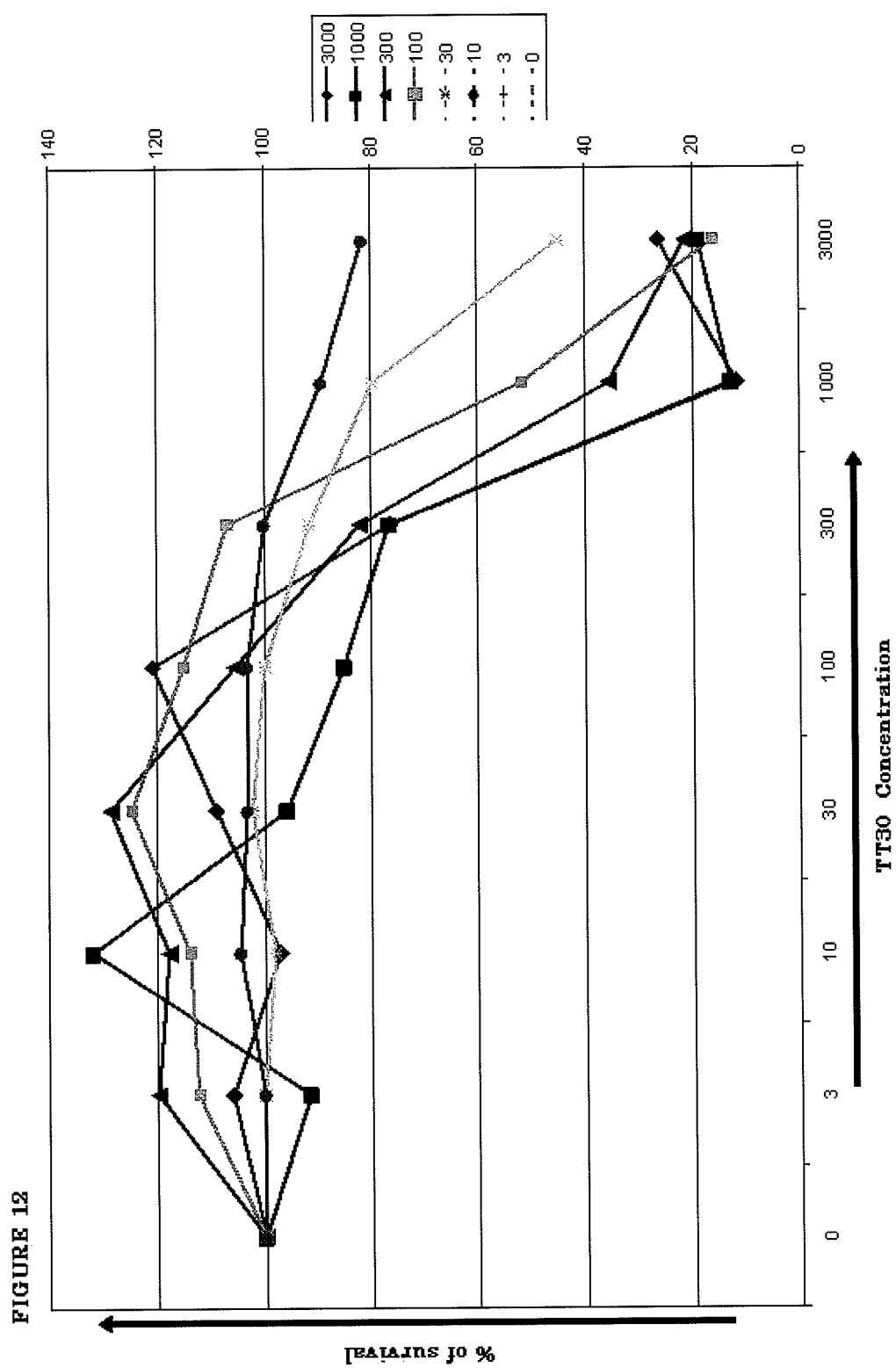
FIG. 12 illustrates the complement-mediated hemolysis of PNH RBCs from a previously untreated subject, and in particular the survival of PNH RBCs treated with TT30, a potent inhibitor of C3 convertase. Data represents the percent of RBCs lysed at various time points versus the concentration of TT30 administered compared with the RBCs lysed by acidified serum. It can be noted that the percent of PNH RBCs that are lysed decreases with higher doses of TT30.
Figure 13:
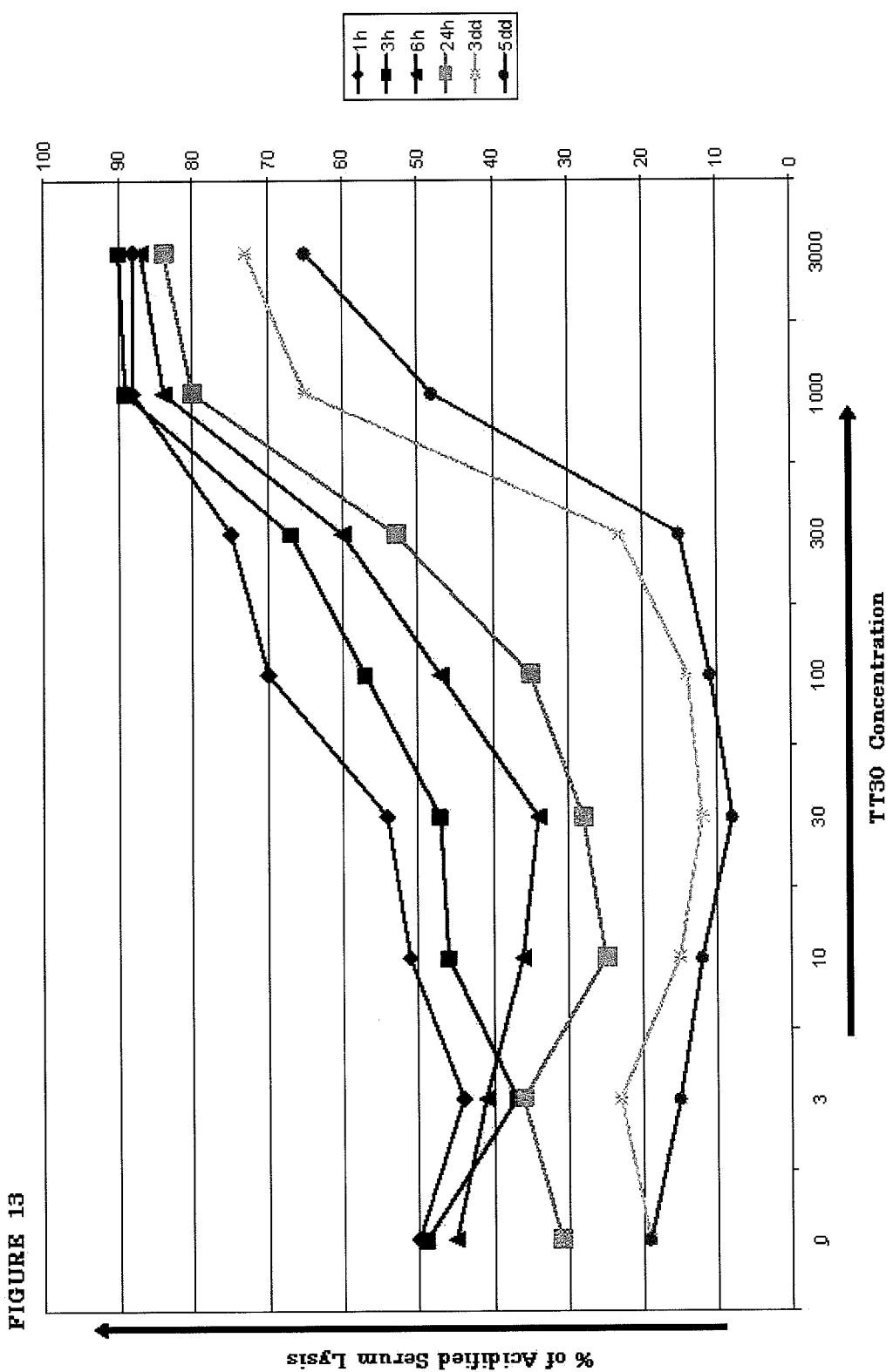
FIG. 13 illustrates the survival of PNH RBCs from a subject who had been previously treated with eculizumab, with various treatments over the course of five days. Data represents the percent of PNH RBCs surviving in cells treated with acidified serum+magnesium (AcS+Mg) (a) with no inhibitors; (b) with TT30 (TT) at 3000 nM; and (c) with TT30 (TT) at 4500 nM
Figure 14:
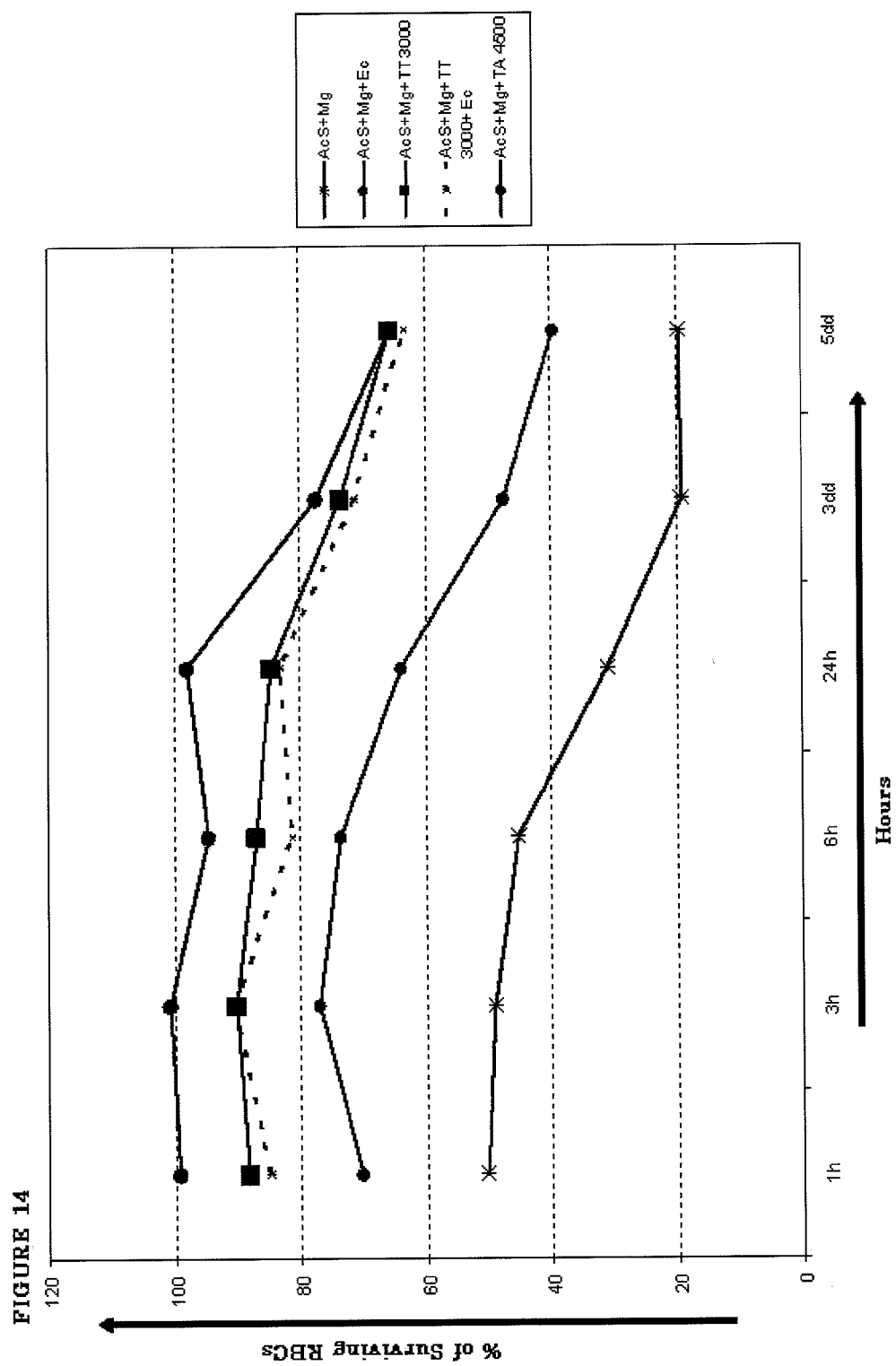
FIG. 14 illustrates the survival of PNH RBCs from a subject who had been previously treated with eculizumab, for treatment with various concentrations of TT30 over 5 days. Data represents the percent of surviving PNH RBCs with various concentrations of TT30 vs time of treatment. It can be noted that the percent of surviving PNH RBCs increases with higher doses of TT30.
Figure 15:
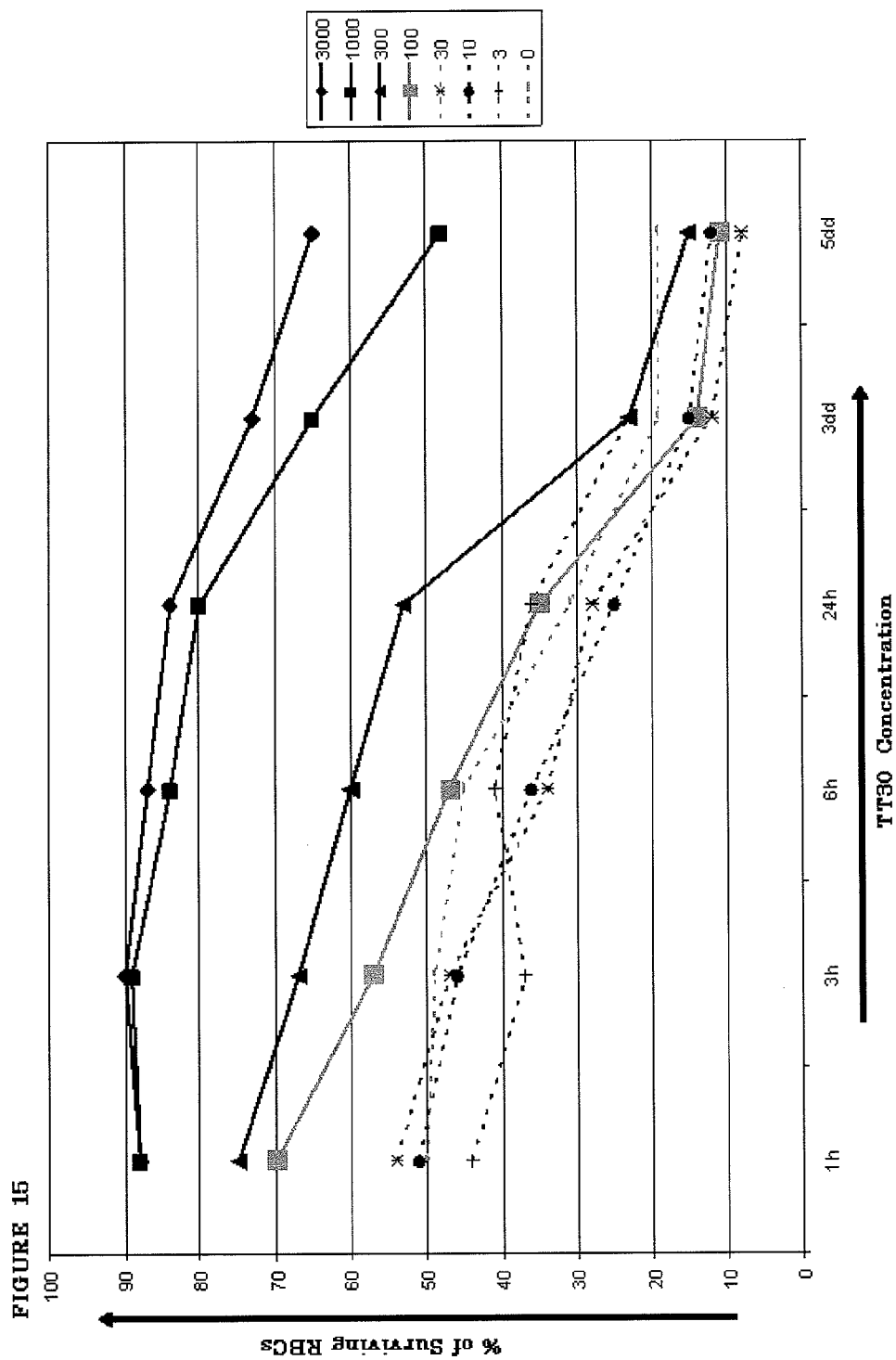
FIG. 15 illustrates the complement-mediated hemolysis of PNH RBCs from a subject who had been previously treated with eculizumab, and in particular the survival of PNH RBCs treated with TT30, a potent inhibitor of C3 convertase. Data represents the percent of RBC lysis at various time points versus the concentration of TT30 administered compared with RBC lysis by acidified serum. It can be noted that the percent of PNH RBCs that are lysed decreases with higher doses of TT30.
Figure 16:
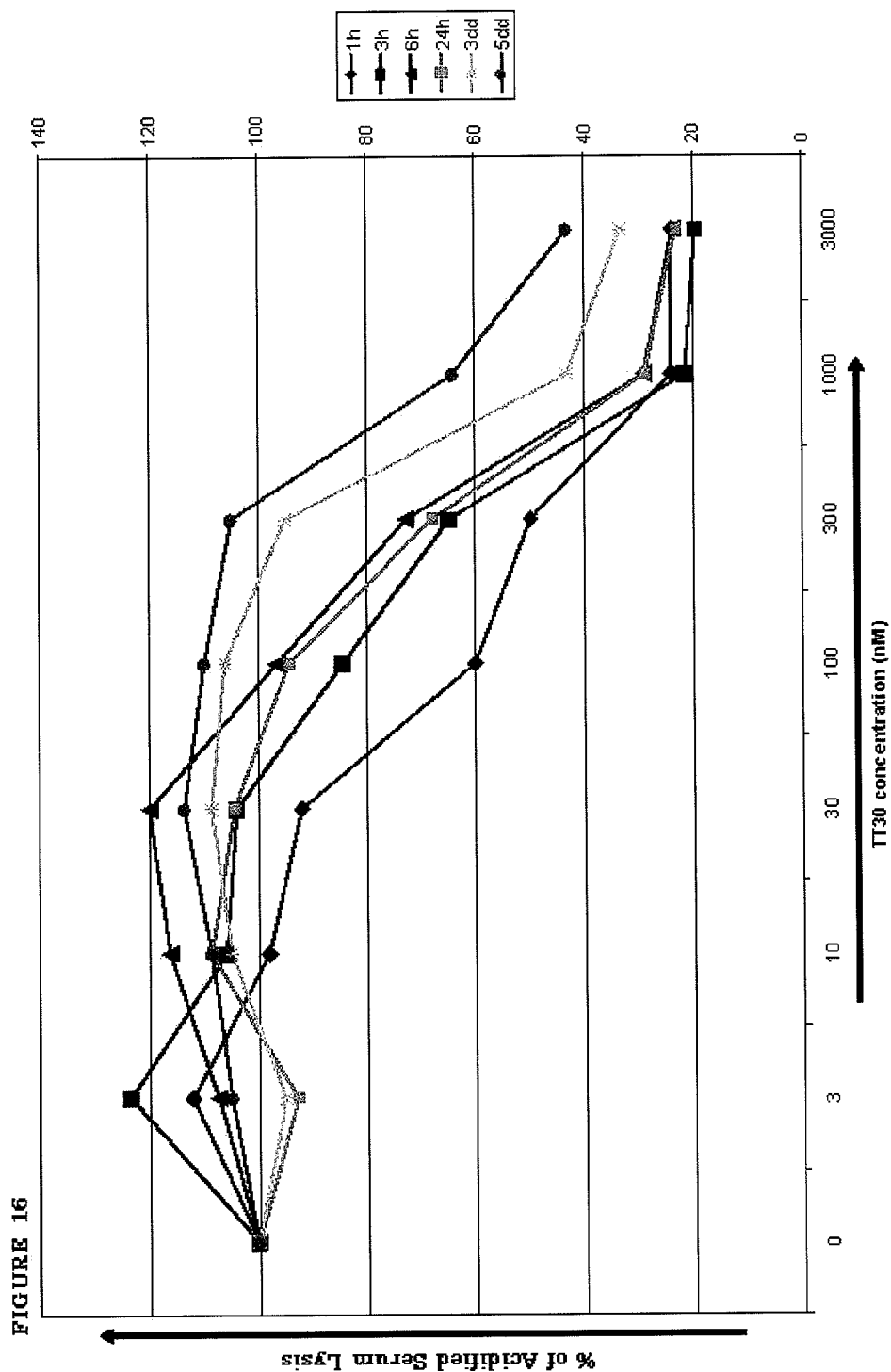
FIG. 16 illustrates the percent inhibition of hemolysis of PNH RBCs at 24 hours after treatment with varying concentrations of TT30. The results are pooled from seven independent experiments from a total of four subjects.

Several subjects were studied for survival of red blood cells in the spleen and liver during treatment with anti-C5 antibody. As exemplified in FIG. 8, increased entrapment of red blood cells in both spleen and liver was detected in all three subjects studied.

RBCs from subjects with PNH were then treated with varying doses of TT30, a potent inhibitor of C3 convertase. As demonstrated in FIGS. 9 through 16, PNH RBC survival increased with TT30 treatment in a dose dependent fashion. It was found that TT30 strongly inhibited hemolysis of PNH RBCs in acidified serum. The protection was dose and time dependent. TT30 inhibited C3 binding on PNH RBCs taken from subjects who had been previously untreated, as well as PNH RBCs taken from subjects who had been previously treated with the terminal complement inhibitor eculizumab.

Figure 17:
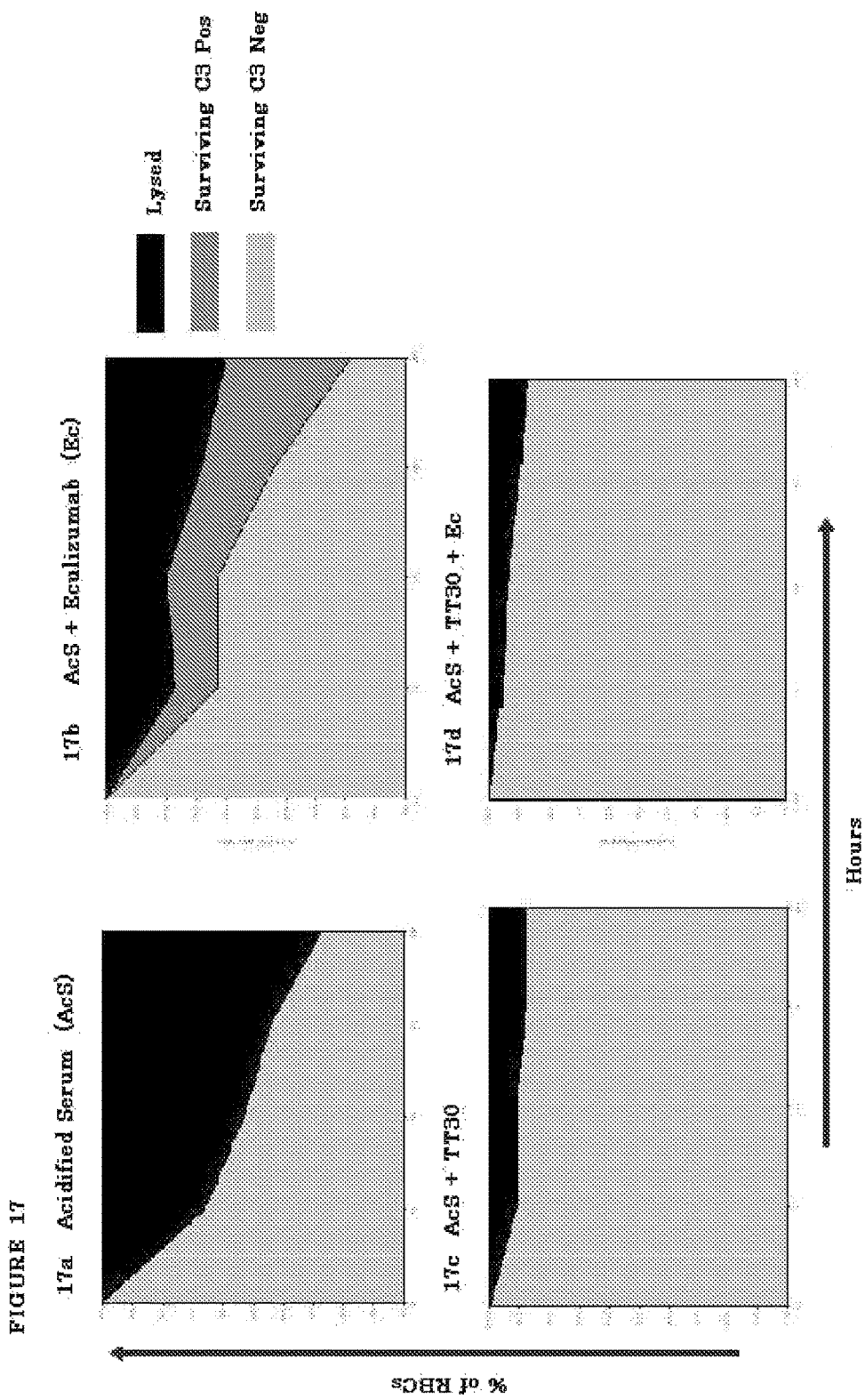
FIG. 17 illustrates the fate of PNH RBCs from a previously untreated subject after various timepoints. Measurements were taken over a 24 hour period. The treatments were (FIG. 17a): and acidified serum (AcS)
Figure 18:
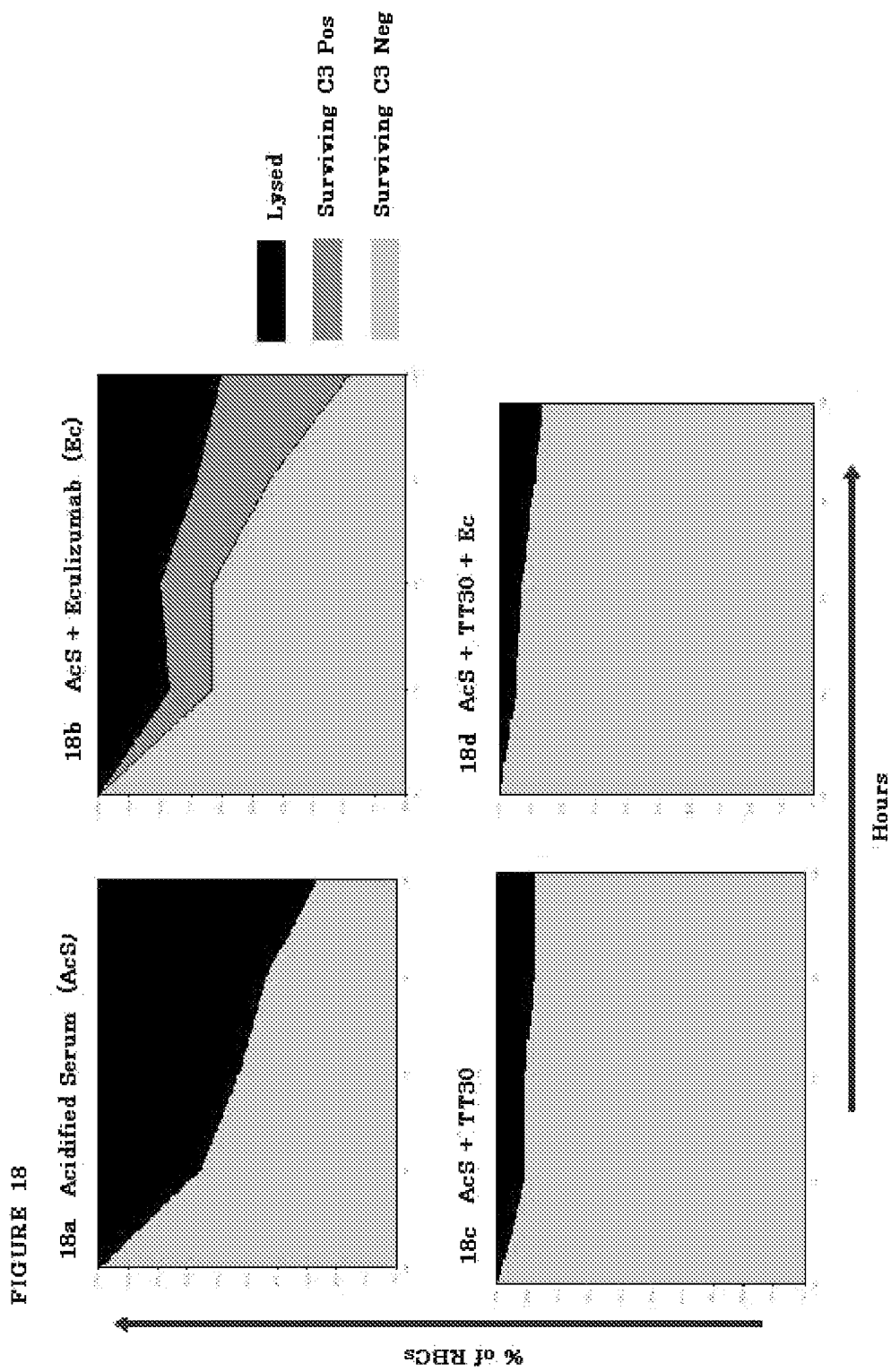
FIG. 18 illustrates the fate of PNH RBCs from a second previously untreated subject after various timepoints. Measurements were taken over a 24 hour period. The treatments were (FIG. 18a): acidified serum (AcS)
Figure 19:
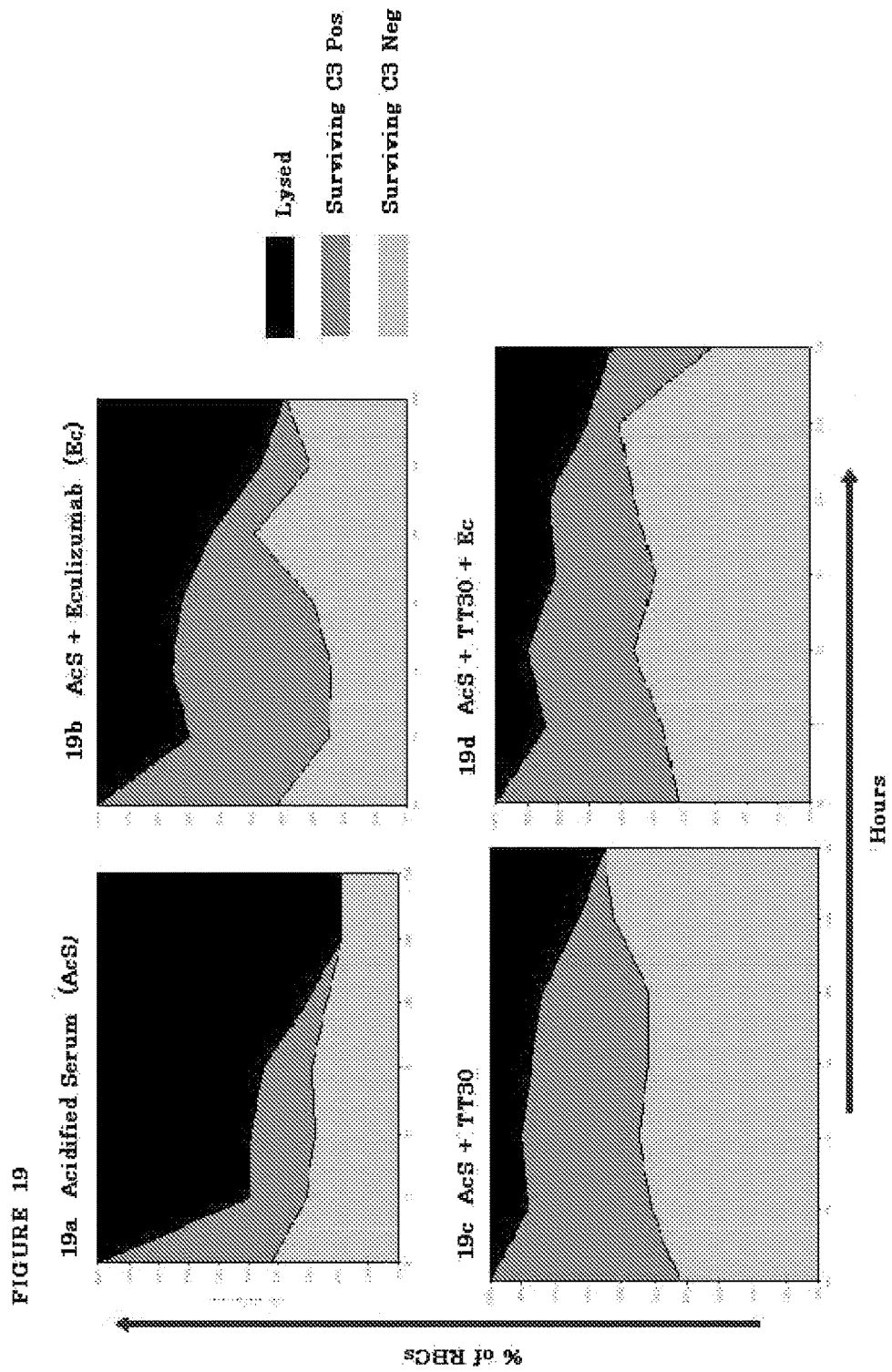
FIG. 19 illustrates the fate of PNH RBCs from a subject who has previously untreated been treated with eculizumab, after various timepoints. Measurements were taken over a 24 hour period. The treatments were (FIG. 19a): Acidified serum (AcS)

FIGS. 17 through 19 illustrate the results of the modified Ham test, in which red blood cells from subjects who had not been previously treated (FIG. 17 and FIG. 18), and from a subject who had previously been treated with the terminal complement inhibitor eculizumab (FIG. 19), were placed in acidified serum and subjected to various treatments over a 24 hour period, including (a) Acidified serum (AcS) without additional treatment; (b): AcS+3000 nM TT30. As can be seen from these figures, surviving C3-positive cells were seen in subjects who had been pretreated with eculizumab. However, subjects who had not been treated with eculizumab did not exhibit C3-positive RBCs.

Example 4: Treatment of Subjects Exhibiting Complement-Mediated Hemolytic Disorders with Targeted CAP Inhibitor TT30

Subjects exhibiting a complement-mediated hemolytic disorder, such as PNH, who have not previously been treated are dosed with TT30. Treatment lasts for a duration of 3 months, during which LDH, Hemoglobin gain and C3 binding was monitored at regular intervals.

Example 5: Treatment of Residual Anemia in PNH Subjects Previously Treated with Anti-05 Antibodies Subjects exhibiting PNH who have previously been treated with anti-C5 antibody, but who exhibit at least one characteristic of complement-mediated extravascular hemolysis are dosed with TT30. Treatment with both anti-C5 antibody and TT30 lasts for a duration of 3 months, during which LDH, Hemoglobin gain and C3 binding are monitored at regular intervals.

Example 6: Treatment of Subjects Exhibiting Complement-Mediated Hemolytic Disorders with Other Complement Alternative Pathway Inhibitors Subjects exhibiting a complement-mediated hemolytic disorder, such as PNH, are dosed with at least one targeted inhibitor of the complement alternative pathway, from the following:

(a) TT30 (CR2-targeted Factor H);
(b) TT32 (CR2-targeted CR1)
(c) Anti-Factor B antibody; (for example, TA106);

(d) TT31 (CR2-targeted double-Factor H);
(e) DAF
(f) Anti-properdin antibody;
(g) Anti-Factor D antibody;
(h) Complement Factor I;
(i) Compstatin;
(j) CR2-targeted Anti-Factor B antibody;
(k) CR2-targeted DAF;
(l) CR2-targeted Anti-Properdin antibody
(m) CR2-targeted Anti-Factor D antibody;
(n) CR2-targeted Complement Factor I;
(o) CR2-targeted Compstatin;
(p) MCP;
(q) CR2-targeted MCP
(r) Factor H
(s) CR1
(t) MAP1;
(u) CR2-targeted MAP1;
(v) Anti-MASP1 antibody;
(w) CR2-targeted Anti-MASP1 antibody.

Treatment with the above complement inhibitors may last for a duration of 3 months, during which LDH, Hemoglobin gain and C3 binding are monitored at regular intervals in order to determine the subjects' response to each of the complement alternative pathway inhibitors.

Example 8: Binding of TT30 to Asthmatic Human and Cynomolgus Monkey Lungs

Figure 24:
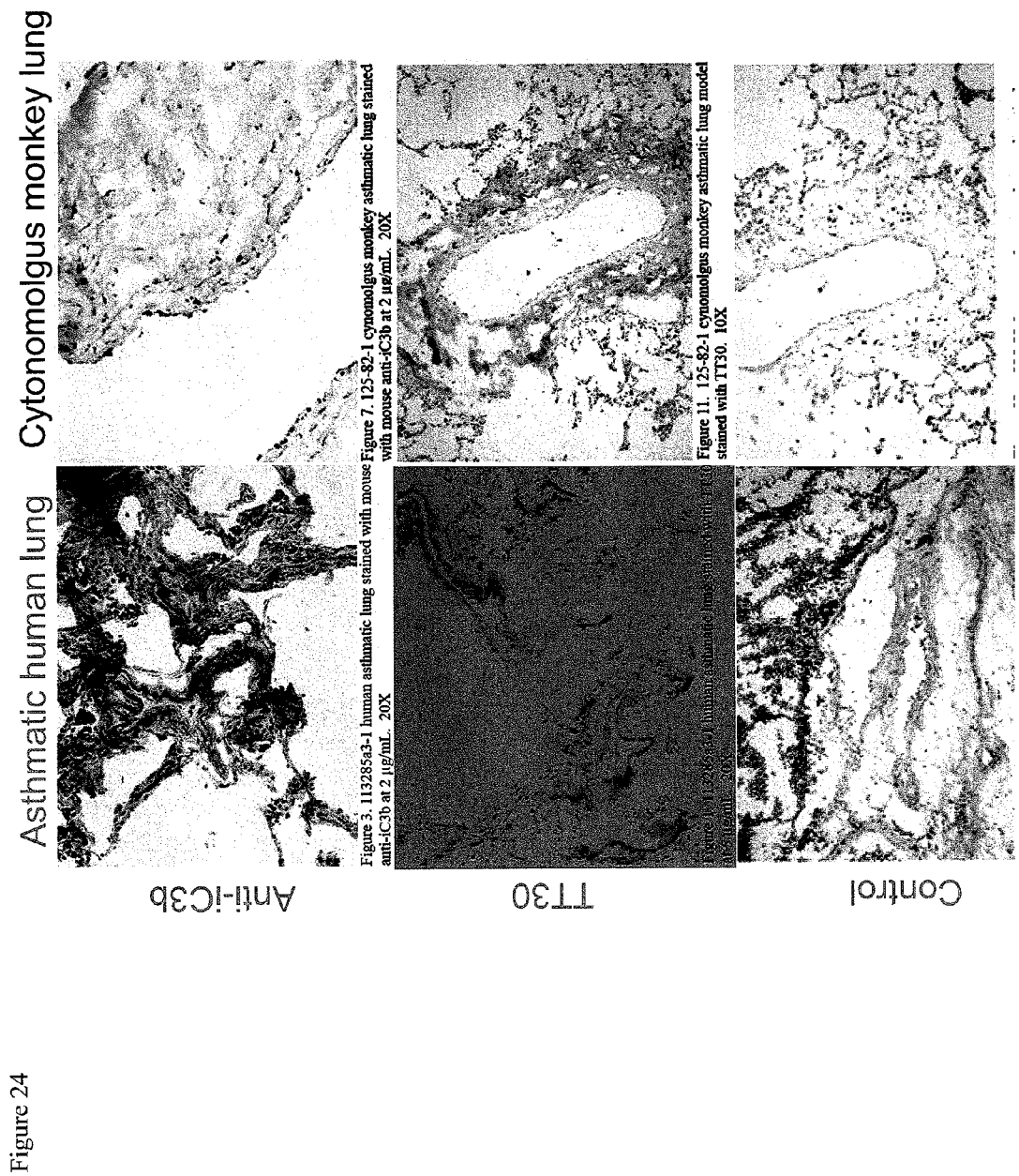
FIG. 24 illustrates the binding of TT30 and anti-C3b monoclonal antibody to asthmatic human and cynomolgus monkey.

Asthmatic human and cynomolgus lung tissue samples were prepared and were stained with TT30 and with Anti-iC3b monoclonal antibody, respectively. Both TT30 and Anti-iC3b monoclonal antibody showed similar staining patterns, as shown in FIG. 24. Later experiments demonstrated that TT30 staining of asthmatic lung tissue can be blocked by anti-C3b monoclonal antibody. Additional experiments demonstrated that TT30 staining of asthmatic lung tissue can also be blocked with anti-CR2 monoclonal antibodies. These results indicate that TT30 may be used as an immunostaining reagent. These results further support a conclusion that TT30 binds to asthmatic lung tissue via binding of the CR2 portion of TT30 to C3 fragments present on the tissue.

Example 9: Rabbit Red Blood Cells (RBC) Hemolysis Assay

An assay was developed at Taligen Therapeutics to measure CAP-mediated hemolysis of rabbit RBCs by human serum. This assay measures the release of hemoglobin from rabbit RBCs lysed upon exposure to human serum. Water and EDTA were used as positive and negative controls for the assay, respectively. The reported values for serum CAP-mediated hemolysis of rabbit RBCs are expressed as percent (%) of lysis observed with water (100%). This assay can be used for the purpose of assessing TT30 activity, i.e., the extent to which TT30 inhibits CAP-mediated hemolysis of rabbit RBCs. As serum C3 is activated and C3 activation fragments (iC3b, C3dg and C3d) are deposited on rabbit RBCs, TT30 binds to these fragments via CR2 SCR1-4 and inhibits CAP-mediated C5b-9 formation via fH SCR 1-5. In the presence of TT30, serum CAP activity will be reduced (inhibited) in a concentration-dependent manner. TT30 activity can therefore be expressed as the relative (%) inhibition of CAP-mediated rabbit RBC hemolysis, as compared to a serum sample without TT30 (e.g., baseline samples).

Rabbit RBC (Bioreclamation, Liverpool, N.Y.) were washed, adjusted to $2.9 \times 10^9$ erythrocytes/mL and incubated with human complement-preserved serum containing serial dilutions of TT30 under experimental conditions promoting CAP activity (MgEGTA) and subsequent hemolysis. After 30 minutes at 37° C., 25 mM EDTA was added to stop the reaction, followed by centrifugation and removal of the supernatant to a new plate that was read at 415 nm. Percent lysis was calculated as $(A415_{ser\ x} - A415_{ser\ x\ bkgd})/(A415_{water})*100$. RBCs protected from hemolysis assay were stained with anti-C3 fragment antibodies and TT30-detection reagents as described under Flow Cytometry.

Figure 25:
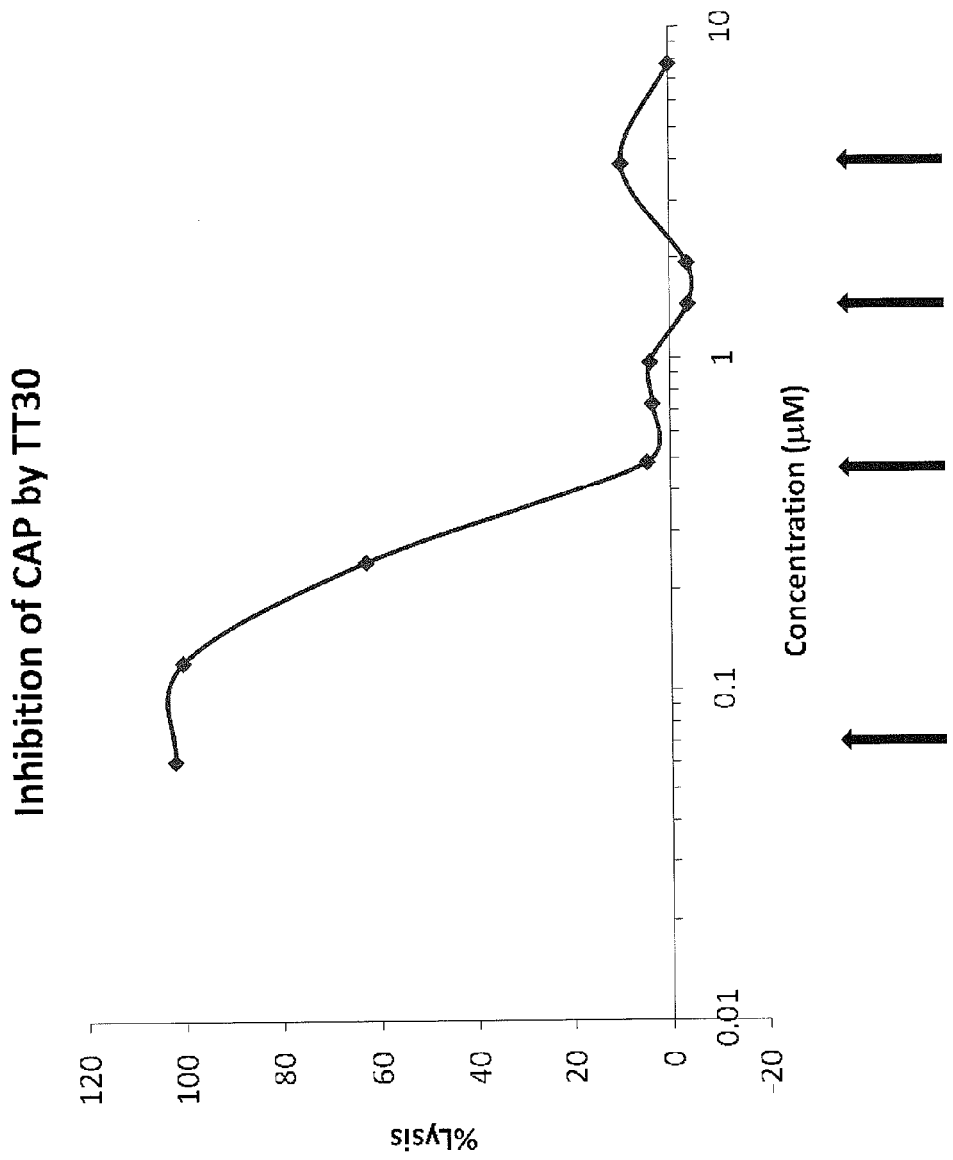
FIG. 25 illustrates the concentration-dependent inhibition of RBC lysis by TT30 in a rabbit red blood cell hemolysis assay.

FIG. 25 illustrates that TT30 exhibited a concentration-dependent inhibition of RBC lysis. At a concentration of 0.46 uM, TT30 exhibits greater than 80% inhibition of hemolysis of RBCs in this assay.

Flow Cytometry

RBCs protected from hemolysis were pooled, centrifuged to remove residual serum and resuspended in PBS/0.1% BSA for flow cytometric staining. RBC were stained with biotinylated monoclonal anti-human C3d (Quidel Corp., San Diego, Calif.) for 30 minutes at ambient temperature, followed by incubation with streptavidin-conjugated APC (BD Biosciences, San Jose, Calif.) and FITC-conjugated HB5 (Santa Cruz Biotechnology, Santa Cruz, Calif.) for additional 30 minutes at ambient temperature. Isotype-matched controls were from BD Biosciences. Cells were analyzed on Accuri® C6 cytometer (Accuri Cytometers Inc., Ann Arbor, Mich.).

Figure 26:
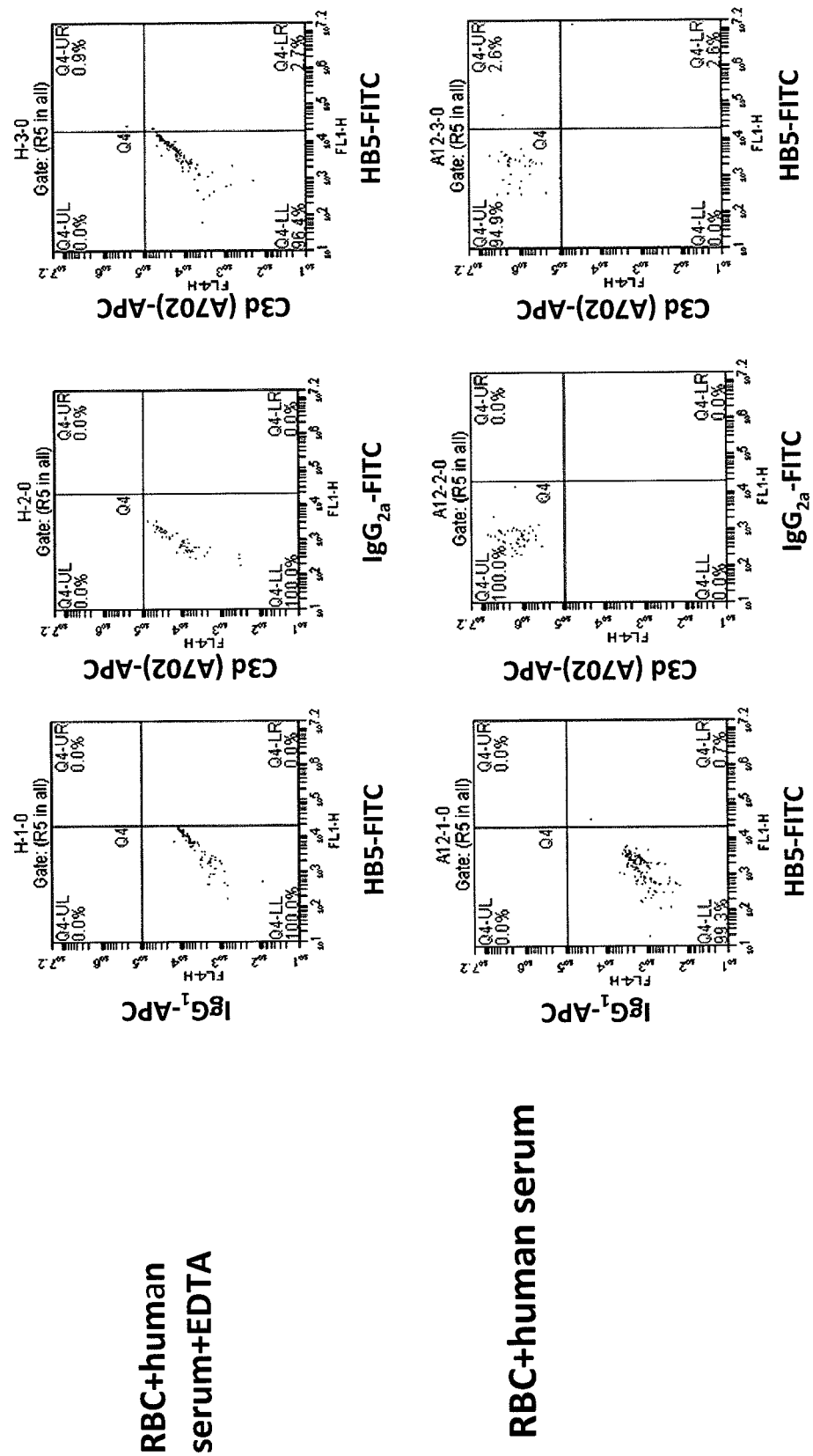
FIG. 26 illustrates that human serum effectively lyses rabbit RBCs in the absence of EDTA. Cell counts indicate that approximately 95% of detected cells stain positively for the presence of C3d fragments in rabbit RBCs in the absence of EDTA.

FIG. 26 illustrates that human serum effectively lyses rabbit RBCs in the absence of EDTA (bottom row). Cell counts indicate that approximately 95% of cells detected stain positively for the presence of C3d fragments.

Figure 27:
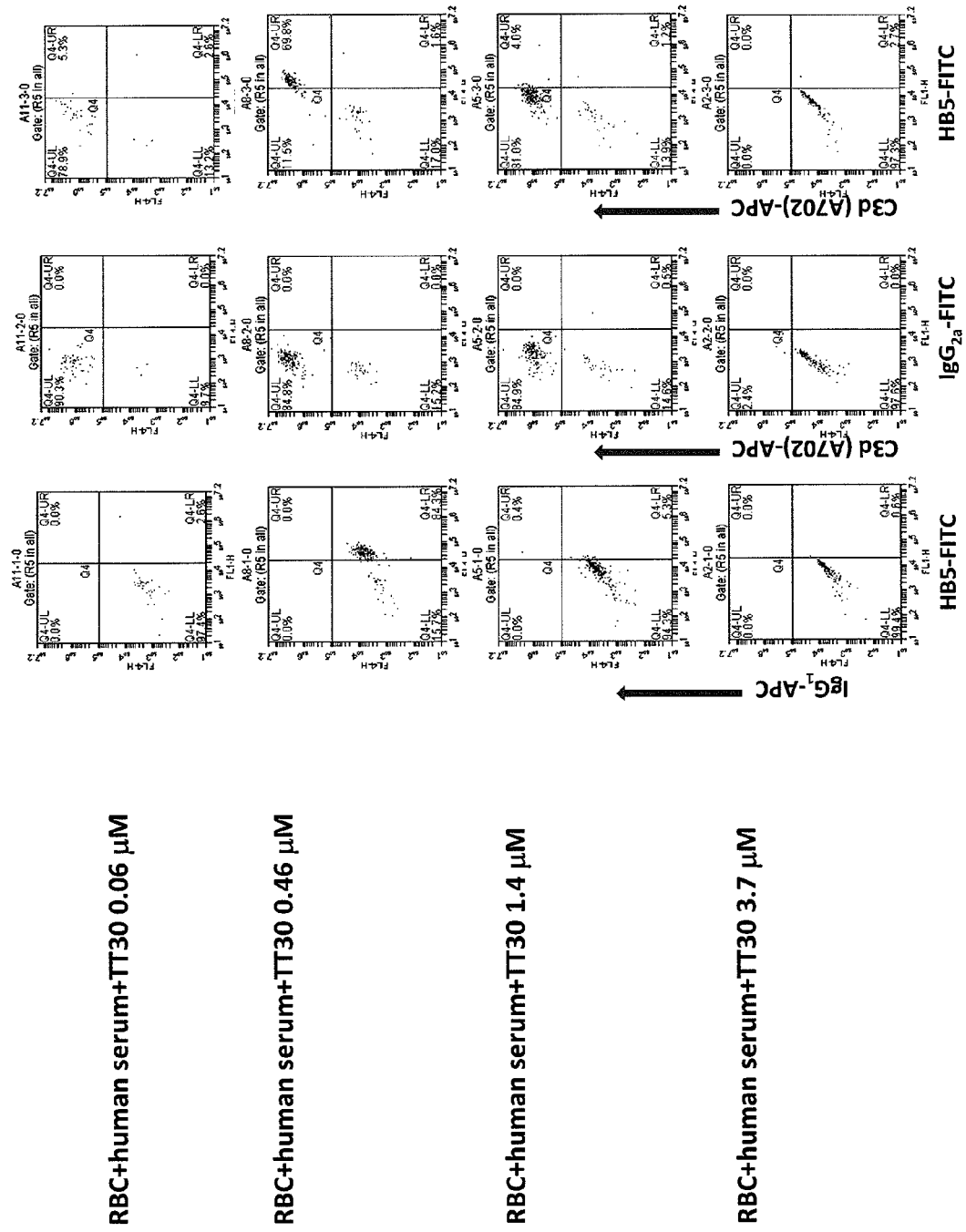
FIG. 27 illustrates that, with addition of increasing concentrations of TT30, at a TT30 concentration of 0.46 uM, TT30 is bound to approximately 70% of the detected cells (upper right quadrant).

FIG. 27 illustrates that, with addition of increasing concentrations of TT30, at a TT30 concentration of 0.46 uM, TT30 bound to the cells is detected in approximately 70% of the stained cells (upper right quadrant). At a TT30 concentration of 1.4 uM, which is shown to inhibit hemolysis, approximately 90-95% of detected cells stain positively for the presence of C3 fragments. Since the RBCs have not been lysed, this most likely indicates the presence of inactive C3 fragments. Very little TT30 is observed, indicating that TT30 is no longer bound to the cells, but is most likely in the fluid phase. At a TT30 concentration of 3.7 uM, no C3 fragments or TT30 is detected on the RBC surface. This indicates that the concentration of TT30 is most likely present in an amount sufficient to prevent binding of C3 fragments to the RBCs, most likely by TT30 binding of C3 fragments in the fluid phase.

Figure 28:
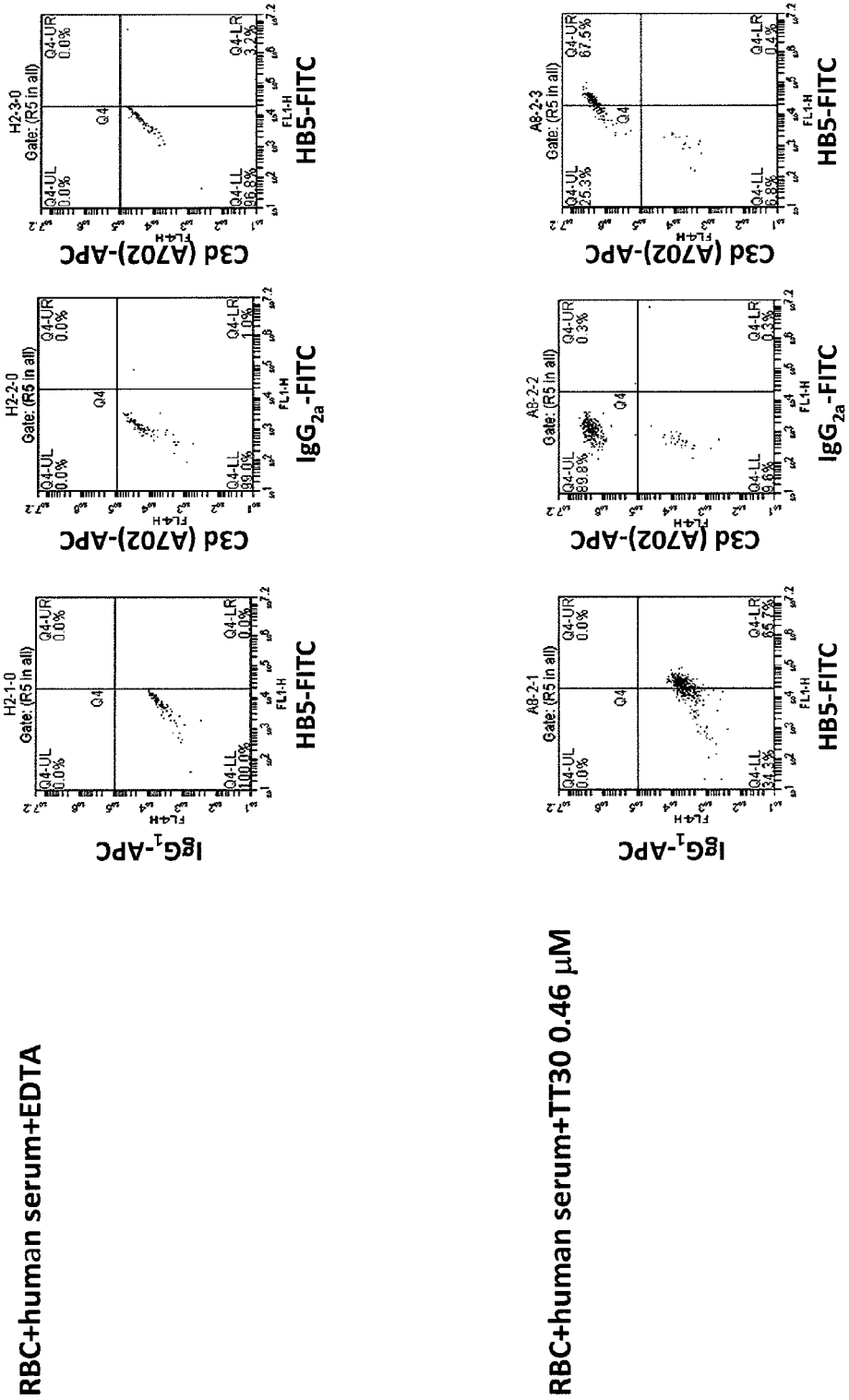
FIGS. 28 through 30 illustrate that the TT30 is present on the surface of 70% of detected RBCs at T=0, and that significant numbers of RBCs continue to stain positively for TT30 after 24 hours.
Figure 29:
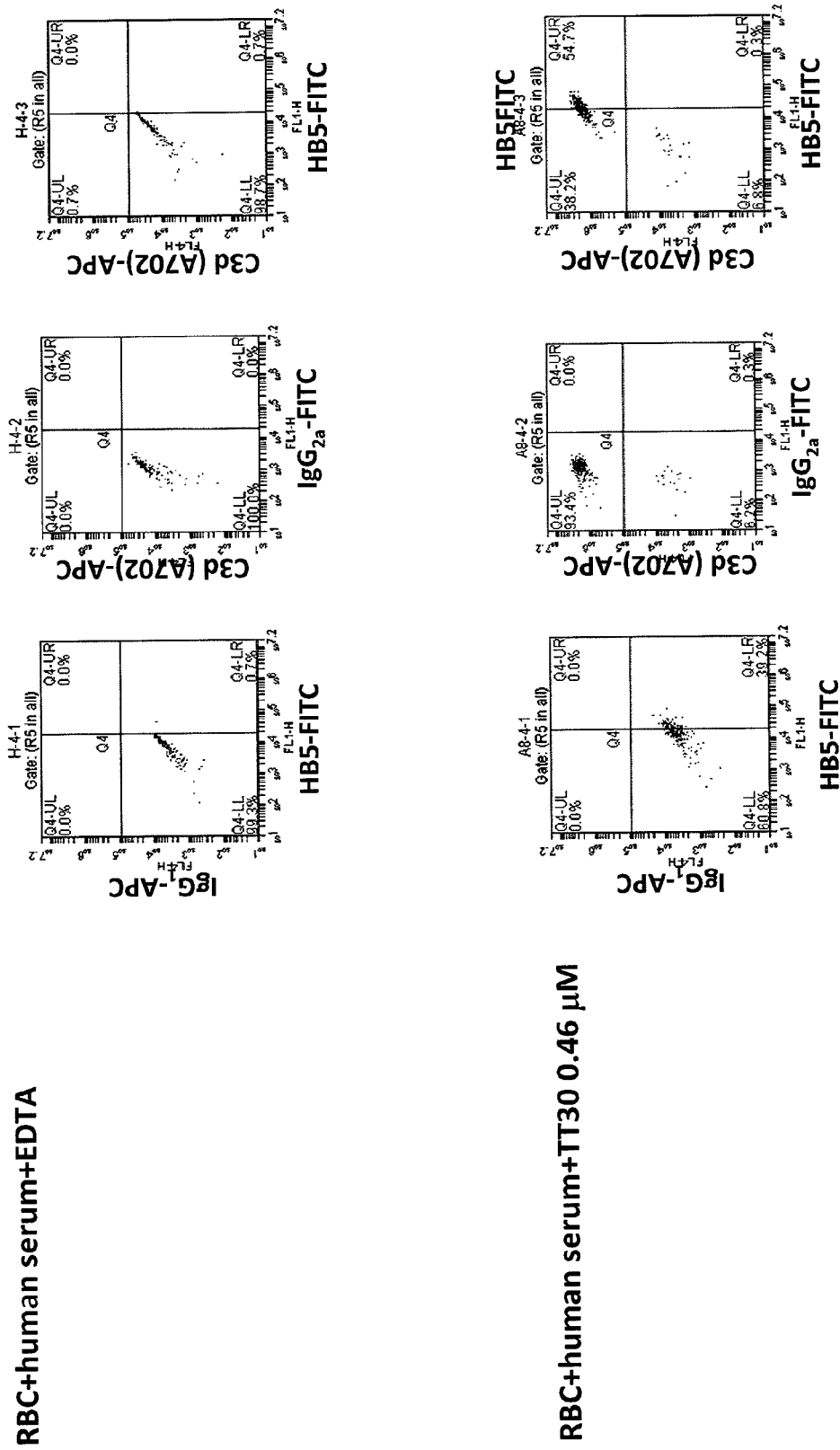
Figure 30:
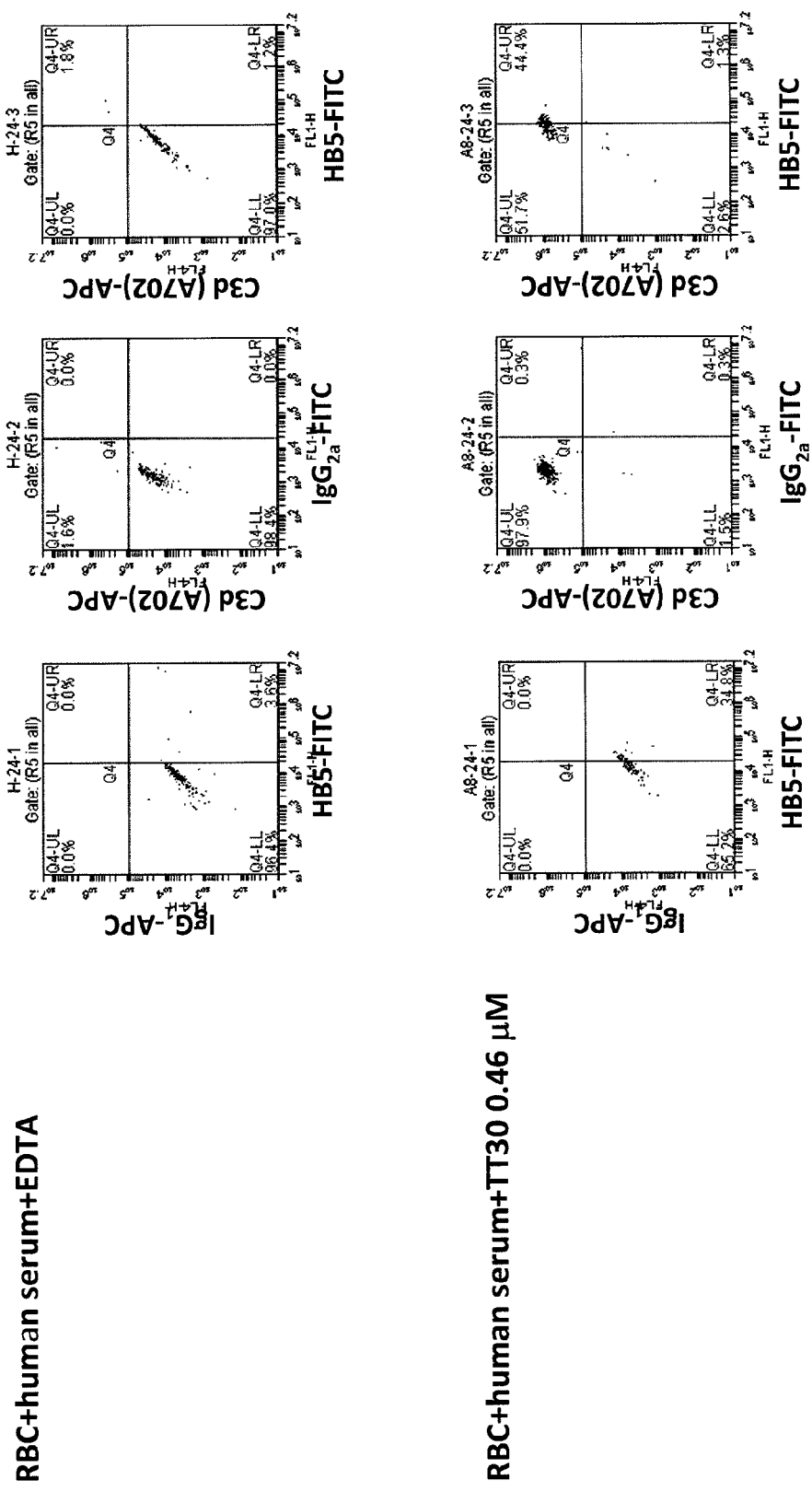

FIGS. 28 through 30 illustrate that the TT30 which is detected on the surface of 70% of RBCs at T=0, with a TT30 concentration of 0.46 uM remains present at 2 hours after addition of TT30 (67.5%). Significant numbers of RBCs continue to stain positively for TT30 at T=4 hours (54.7%) and T=24 hours (44.4%).

Sequences

SEQ ID NO: 1 [complete amino acid sequence of human complement receptor 2 (CR2)]:

```
MGAAGLLGVF LALVAPGVLG ISCGSPPPIL NGRISYYSTP

IAVGTVIRYS CSGTFRLIGE KSLLCITKDK VDGTWDKPAP

KCEYFNKYSS CPEPIVPGGY KIRGSTPYRH GDSVTFACKT

NFSMNGNKSV WCQANNMWGP TRLPTCVSVF PLECPALPMI
```

-continued

```
HNGHHTSENV GSIAPGLSVT YSCESGYLLV GEKIINCLSS

GKWSAVPPTC EEARCKSLGR FPNGKVKEPP ILRVGVTANF

FCDEGYRLQG PPSSRCVIAG QGVAWTKMPV CEEIFCPSPP

PILNGRHIGN SLANVSYGSI VTYTCDPDPE EGVNFILIGE

STLRCTVDSQ KTGTWSGPAP RCELSTSAVQ CPHPQILRGR

MVSGQKDRYT YNDTVIFACM FGFTLKGSKQ IRCNAQGTWE

PSAPVCEKEC QAPPNILNGQ KEDRHMVRFD PGTSIKYSCN

PGYVLVGEES IQCTSEGVWT PPVPQCKVAA CEATGRQLLT

KPQHQFVRPD VNSSCGEGYK LSGSVYQECQ GTIPWFMEIR

LCKEITCPPP PVIYNGAHTG SSLEDFPYGT TVTYTCNPGP

ERGVEFSLIG ESTIRCTSND QERGTWSGPA PLCKLSLLAV

QCSHVHIANG YKISGKEAPY FYNDTVTFKC YSGFTLKGSS

QIRCKRDNTW DPEIPVCEKG CQPPPGLHHG RHTGGNTVFF

VSGMTVDYTC DPGYLLVGNK SIHCMPSGNW SPSAPRCEET

CQHVRQSLQE LPAGSRVELV NTSCQDGYQL TGHAYQMCQD

AENGIWFKKI PLCKVIHCHP PPVIVNGKHT GMMAENFLYG

NEVSYECDQG FYLLGEKNCS AEVILKAWIL ERAFPQCLRS

LCPNPEVKHG YKLNKTHSAY SHNDIVYVDC NPGFIMNGSR

VIRCHTDNTW VPGVPTCIKK AFIGCPPPPK TPNGNHTGGN

IARFSPGMSI LYSCDQGYLV VGEPLLLCTH EGTWSQPAPH

CKEVNCSSPA DMDGIQKGLE PRKMYQYGAV VTLECEDGYM

LEGSPQSQCQ SDHQWNPPLA VCRSRSLAPV LCGIAAGLIL

LTFLIVITLY VISKHRERNY YTDTSQKEAF HLEAREVYSV

DPYNPAS
```

SEQ ID NO: 2 [amino acid sequence of short consensus repeat (SCR) domains 1 and 2 of human CR2]:

```
ISCGSPPPIL NGRISYYSTP IAVGTVIRYS CSGTFRLIGE

KSLLCITKDK VDGTWDKPAP KCEYFNKYSS CPEPIVPGGY

KIRGSTPYRH GDSVTFACKT NFSMNGNKSV WCQANNMWGP

TRLPTCVS
```

---

The invention claimed is:

1. A method of treating a subject with paroxysmal nocturnal hemoglobinuria (PNH) comprising administering to said subject a terminal complement inhibitor and, subsequent to administration of the terminal complement inhibitor, administering an inhibitor of the complement alternative pathway to the subject once the subject has been determined to be non-responsive or partially responsive to the terminal complement inhibitor based on an assessment of at least one hemolytic marker of the subject, wherein said inhibitor of the complement alternative pathway is a complement receptor 2 ("CR2")-Factor H ("FH") molecule comprising:
   a) a CR2 portion comprising a CR2 or a fragment thereof; and
   b) a FH portion comprising a FH or a fragment thereof, wherein said CR2 portion of the CR2-FH molecule is capable of binding to a CR2 ligand, wherein said FH portion of the CR2-FH molecule is capable of inhibiting complement activation of the alternative pathway.

2. The method of claim 1, wherein said PNH results in a symptom selected from the group consisting of: residual anemia and incomplete control of intravascular hemolysis (IVH).

3. The method of claim 1, wherein said at least one hemolytic marker is selected from the group consisting of:
   a) continued loss of red blood cells by ongoing or intermittent intravascular hemolysis and/or extravascular hemolysis;
   b) red blood cells opsonized by fragments of C3;
   c) a need for periodic blood transfusions to said subject;
   d) low normal or below normal levels of hemoglobin;
   e) low normal or below normal levels of platelets;
   f) high normal or above normal reticulocytes;
   g) high normal or above normal bilirubin; and
   h) iron overload or risk of iron overload.

4. The method of claim 3, wherein said symptom is a need for periodic blood transfusions to said subject.

5. The method of claim 3, wherein said symptom is below normal levels of hemoglobin.

6. The method of claim 1, wherein said subject was initially responsive to the treatment of said terminal complement inhibitor but is experiencing recurrence of said PNH prior to administration of CR2-FH molecule.

7. The method of claim 1, wherein said subject is rendered transfusion independent after administering said CR2-FH molecule.

8. The method of claim 1, wherein said terminal complement inhibitor inhibits the formation of the Membrane Attack Complex (MAC).

9. The method of claim 1, wherein said terminal complement inhibitor inhibits complement component C5 (C5) cleavage.

10. The method of claim 1, wherein said terminal complement inhibitor is an anti-C5 antibody or antigen-binding fragment thereof.

11. The method of claim 10, wherein said terminal complement inhibitor is eculizumab or pexelizumab.

12. The method of claim 1, wherein said CR2-FH molecule prevents or reduces opsonization of C3 fragments on red blood cells (RBCs) in said subject.

13. The method of claim 1, wherein said CR2-FH molecule reduces hemolytic lysis of RBCs in said subject.

14. The method of claim 13, wherein said hemolytic lysis is extravascular hemolysis (EVH).

15. The method of claim 1, wherein said CR2-FH molecule improves RBC survival in said subject.

16. The method of claim 1, wherein said CR2 portion comprises the first two N-terminal short consensus repeat (SCR) domains of CR2.

17. The method of claim 1, wherein said CR2 portion comprises the first four N-terminal SCR domains of CR2.

18. The method of claim 1, wherein said FH portion comprises the first four N-terminal SCR domains of FH.

19. The method of claim 1, wherein said FH portion comprises the first five N-terminal SCR domains of FH.

20. The method of claim 1, wherein said CR2 portion comprises the first two N-terminal SCR domains of CR2 and said FH portion comprises the first four N-terminal SCR domains of FH.

21. The method of claim 1, wherein said CR2 portion comprises the first four N-terminal SCR domains of CR2 and said FH portion comprises the first five N-terminal SCR domains of FH.

22. The method of claim 1, wherein said CR2 portion comprises amino acids 23 to 271 of SEQ ID NO: 1.

23. The method of claim 1, wherein said CR2-FH molecule comprises the amino acid sequence of SEQ ID NO: 3.

24. The method of claim 1, wherein said CR2-FH molecule comprises two or more FH portions, wherein each of said two or more FH portions comprises a FH or a fragment thereof that is capable of inhibiting complement activation of the alternative pathway.

25. The method of claim 1, wherein said CR2 portion and the FH portion is fused with or without a linker.

26. The method of claim 1, wherein said CR2-FH molecule is administered to the subject by intravenous, intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational, mucosal, subcutaneous, transdermal, gastrointestinal, intraarticular, intracisternal, intraventricular, rectal, vaginal, intracranial, intraurethral, intrahepatic, or intratumoral administration.

27. The method of claim 1, wherein said CR2-FH molecule is administered intravenously to said subject.

28. The method of claim 1, wherein said subject is a human.

29. The method of claim 1, wherein said terminal complement inhibitor is eculizumab, and wherein said CR2 portion comprises the first two N-terminal SCR domains of CR2 and said FH portion comprises the first four N-terminal SCR domains of FH.

30. The method of claim 1, wherein the CR2-FH molecule is administered at a dosage that provides a serum concentration of the CR2-FH molecule in the range of 0.003 µM to 3 µM.

31. The method of claim 1, wherein said subject is administered said CR2-FH molecule 1 day to 8 weeks after administration of said terminal complement inhibitor.

32. The method of claim 1, wherein said subject is administered said CR2-FH molecule at least 1 week after the administration of said terminal complement inhibitor.

33. The method of claim 1, wherein said subject is administered said CR2-FH molecule at least 2 weeks after the administration of said terminal complement inhibitor.

* * * * *

SEQUENCE LISTING

<160> NUMBER OF SEQ ID NOS: 3

<210> SEQ ID NO 1
<211> LENGTH: 1087
<212> TYPE: PRT
<213> ORGANISM: Homo sapiens

<400> SEQUENCE: 1

```
Met Gly Ala Ala Gly Leu Leu Gly Val Phe Leu Ala Leu Val Ala Pro
1               5                   10                  15

Gly Val Leu Gly Ile Ser Cys Gly Ser Pro Pro Pro Ile Leu Asn Gly
            20                  25                  30

Arg Ile Ser Tyr Tyr Ser Thr Pro Ile Ala Val Gly Thr Val Ile Arg
        35                  40                  45

Tyr Ser Cys Ser Gly Thr Phe Arg Leu Ile Gly Glu Lys Ser Leu Leu
    50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
        115                 120                 125

Ser Val Trp Cys Gln Ala Asn Asn Met Trp Gly Pro Thr Arg Leu Pro
    130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175

Leu Ser Val Thr Tyr Ser Cys Glu Ser Gly Tyr Leu Leu Val Gly Glu
```

-continued

```
                180                 185                 190
Lys Ile Ile Asn Cys Leu Ser Ser Gly Lys Trp Ser Ala Val Pro Pro
            195                 200                 205
Thr Cys Glu Glu Ala Arg Cys Lys Ser Leu Gly Arg Phe Pro Asn Gly
        210                 215                 220
Lys Val Lys Glu Pro Pro Ile Leu Arg Val Gly Val Thr Ala Asn Phe
225                 230                 235                 240
Phe Cys Asp Glu Gly Tyr Arg Leu Gln Gly Pro Pro Ser Ser Arg Cys
                245                 250                 255
Val Ile Ala Gly Gln Gly Val Ala Trp Thr Lys Met Pro Val Cys Glu
            260                 265                 270
Glu Ile Phe Cys Pro Ser Pro Pro Ile Leu Asn Gly Arg His Ile
        275                 280                 285
Gly Asn Ser Leu Ala Asn Val Ser Tyr Gly Ser Ile Val Thr Tyr Thr
        290                 295                 300
Cys Asp Pro Asp Pro Glu Glu Gly Val Asn Phe Ile Leu Ile Gly Glu
305                 310                 315                 320
Ser Thr Leu Arg Cys Thr Val Asp Ser Gln Lys Thr Gly Thr Trp Ser
                325                 330                 335
Gly Pro Ala Pro Arg Cys Glu Leu Ser Thr Ser Ala Val Gln Cys Pro
            340                 345                 350
His Pro Gln Ile Leu Arg Gly Arg Met Val Ser Gly Gln Lys Asp Arg
        355                 360                 365
Tyr Thr Tyr Asn Asp Thr Val Ile Phe Ala Cys Met Phe Gly Phe Thr
    370                 375                 380
Leu Lys Gly Ser Lys Gln Ile Arg Cys Asn Ala Gln Gly Thr Trp Glu
385                 390                 395                 400
Pro Ser Ala Pro Val Cys Glu Lys Glu Cys Gln Ala Pro Pro Asn Ile
                405                 410                 415
Leu Asn Gly Gln Lys Glu Asp Arg His Met Val Arg Phe Asp Pro Gly
            420                 425                 430
Thr Ser Ile Lys Tyr Ser Cys Asn Pro Gly Tyr Val Leu Val Gly Glu
        435                 440                 445
Glu Ser Ile Gln Cys Thr Ser Glu Gly Val Trp Thr Pro Pro Val Pro
    450                 455                 460
Gln Cys Lys Val Ala Ala Cys Glu Ala Thr Gly Arg Gln Leu Leu Thr
465                 470                 475                 480
Lys Pro Gln His Gln Phe Val Arg Pro Asp Val Asn Ser Ser Cys Gly
                485                 490                 495
Glu Gly Tyr Lys Leu Ser Gly Ser Val Tyr Gln Glu Cys Gln Gly Thr
            500                 505                 510
Ile Pro Trp Phe Met Glu Ile Arg Leu Cys Lys Glu Ile Thr Cys Pro
        515                 520                 525
Pro Pro Pro Val Ile Tyr Asn Gly Ala His Thr Gly Ser Ser Leu Glu
    530                 535                 540
Asp Phe Pro Tyr Gly Thr Thr Val Thr Tyr Thr Cys Asn Pro Gly Pro
545                 550                 555                 560
Glu Arg Gly Val Glu Phe Ser Leu Ile Gly Glu Ser Thr Ile Arg Cys
                565                 570                 575
Thr Ser Asn Asp Gln Glu Arg Gly Thr Trp Ser Gly Pro Ala Pro Leu
            580                 585                 590
Cys Lys Leu Ser Leu Leu Ala Val Gln Cys Ser His Val His Ile Ala
        595                 600                 605
```

```
-continued

Asn Gly Tyr Lys Ile Ser Gly Lys Glu Ala Pro Tyr Phe Tyr Asn Asp
            610                 615                 620

Thr Val Thr Phe Lys Cys Tyr Ser Gly Phe Thr Leu Lys Gly Ser Ser
625                 630                 635                 640

Gln Ile Arg Cys Lys Arg Asp Asn Thr Trp Asp Pro Glu Ile Pro Val
                645                 650                 655

Cys Glu Lys Gly Cys Gln Pro Pro Gly Leu His His Gly Arg His
                660             665                 670

Thr Gly Gly Asn Thr Val Phe Phe Val Ser Gly Met Thr Val Asp Tyr
            675                 680                 685

Thr Cys Asp Pro Gly Tyr Leu Leu Val Gly Asn Lys Ser Ile His Cys
    690                 695                 700

Met Pro Ser Gly Asn Trp Ser Pro Ser Ala Pro Arg Cys Glu Thr
705                 710                 715                 720

Cys Gln His Val Arg Gln Ser Leu Gln Glu Leu Pro Ala Gly Ser Arg
                725                 730                 735

Val Glu Leu Val Asn Thr Ser Cys Gln Asp Gly Tyr Gln Leu Thr Gly
                740                 745                 750

His Ala Tyr Gln Met Cys Gln Asp Ala Glu Asn Gly Ile Trp Phe Lys
            755                 760                 765

Lys Ile Pro Leu Cys Lys Val Ile His Cys His Pro Pro Pro Val Ile
770                 775                 780

Val Asn Gly Lys His Thr Gly Met Met Ala Glu Asn Phe Leu Tyr Gly
785                 790                 795                 800

Asn Glu Val Ser Tyr Glu Cys Asp Gln Gly Phe Tyr Leu Leu Gly Glu
                805                 810                 815

Lys Asn Cys Ser Ala Glu Val Ile Leu Lys Ala Trp Ile Leu Glu Arg
                820                 825                 830

Ala Phe Pro Gln Cys Leu Arg Ser Leu Cys Pro Asn Pro Glu Val Lys
            835                 840                 845

His Gly Tyr Lys Leu Asn Lys Thr His Ser Ala Tyr Ser His Asn Asp
    850                 855                 860

Ile Val Tyr Val Asp Cys Asn Pro Gly Phe Ile Met Asn Gly Ser Arg
865                 870                 875                 880

Val Ile Arg Cys His Thr Asp Asn Thr Trp Val Pro Gly Val Pro Thr
                885                 890                 895

Cys Ile Lys Lys Ala Phe Ile Gly Cys Pro Pro Pro Lys Thr Pro
            900                 905                 910

Asn Gly Asn His Thr Gly Gly Asn Ile Ala Arg Phe Ser Pro Gly Met
            915                 920                 925

Ser Ile Leu Tyr Ser Cys Asp Gln Gly Tyr Leu Val Val Gly Glu Pro
    930                 935                 940

Leu Leu Leu Cys Thr His Glu Gly Thr Trp Ser Gln Pro Ala Pro His
945                 950                 955                 960

Cys Lys Glu Val Asn Cys Ser Ser Pro Ala Asp Met Asp Gly Ile Gln
                965                 970                 975

Lys Gly Leu Glu Pro Arg Lys Met Tyr Gln Tyr Gly Ala Val Val Thr
            980                 985                 990

Leu Glu Cys Glu Asp Gly Tyr Met Leu Glu Gly Ser Pro Gln Ser Gln
        995                 1000                1005

Cys Gln Ser Asp His Gln Trp Asn Pro Pro Leu Ala Val Cys Arg
    1010                1015                1020
```

```
Ser Arg Ser Leu Ala Pro Val Leu Cys Gly Ile Ala Ala Gly Leu
    1025                1030                1035

Ile Leu Leu Thr Phe Leu Ile Val Ile Thr Leu Tyr Val Ile Ser
    1040                1045                1050

Lys His Arg Glu Arg Asn Tyr Tyr Thr Asp Thr Ser Gln Lys Glu
    1055                1060                1065

Ala Phe His Leu Glu Ala Arg Glu Val Tyr Ser Val Asp Pro Tyr
    1070                1075                1080

Asn Pro Ala Ser
    1085

<210> SEQ ID NO 2
<211> LENGTH: 128
<212> TYPE: PRT
<213> ORGANISM: Homo sapiens

<400> SEQUENCE: 2

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
                20                  25                  30

Gly Thr Phe Arg Leu Ile Gly Glu Lys Ser Leu Leu Cys Ile Thr Lys
                35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                    85                  90                  95

Ala Cys Lys Thr Asn Phe Ser Met Asn Gly Asn Lys Ser Val Trp Cys
                100                 105                 110

Gln Ala Asn Asn Met Trp Gly Pro Thr Arg Leu Pro Thr Cys Val Ser
            115                 120                 125

<210> SEQ ID NO 3
<211> LENGTH: 560
<212> TYPE: PRT
<213> ORGANISM: Homo sapiens

<400> SEQUENCE: 3

Ile Ser Cys Gly Ser Pro Pro Ile Leu Asn Gly Arg Ile Ser Tyr
1               5                   10                  15

Tyr Ser Thr Pro Ile Ala Val Gly Thr Val Ile Arg Tyr Ser Cys Ser
                20                  25                  30

Gly Thr Phe Arg Leu Ile Gly Glu Lys Ser Leu Leu Cys Ile Thr Lys
                35                  40                  45

Asp Lys Val Asp Gly Thr Trp Asp Lys Pro Ala Pro Lys Cys Glu Tyr
    50                  55                  60

Phe Asn Lys Tyr Ser Ser Cys Pro Glu Pro Ile Val Pro Gly Gly Tyr
65                  70                  75                  80

Lys Ile Arg Gly Ser Thr Pro Tyr Arg His Gly Asp Ser Val Thr Phe
                    85                  90                  95

Ala Cys Lys Thr Asn Phe Ser Met Asn Gly Asn Lys Ser Val Trp Cys
                100                 105                 110

Gln Ala Asn Asn Met Trp Gly Pro Thr Arg Leu Pro Thr Cys Val Ser
            115                 120                 125
```

Val Phe Pro Leu Glu Cys Pro Ala Leu Pro Met Ile His Asn Gly His
130                 135                 140

His Thr Ser Glu Asn Val Gly Ser Ile Ala Pro Gly Leu Ser Val Thr
145                 150                 155                 160

Tyr Ser Cys Glu Ser Gly Tyr Leu Leu Val Gly Glu Lys Ile Ile Asn
            165                 170                 175

Cys Leu Ser Ser Gly Lys Trp Ser Ala Val Pro Pro Thr Cys Glu Glu
            180                 185                 190

Ala Arg Cys Lys Ser Leu Gly Arg Phe Pro Asn Gly Lys Val Lys Glu
        195                 200                 205

Pro Pro Ile Leu Arg Val Gly Val Thr Ala Asn Phe Phe Cys Asp Glu
210                 215                 220

Gly Tyr Arg Leu Gln Gly Pro Pro Ser Ser Arg Cys Val Ile Ala Gly
225                 230                 235                 240

Gln Gly Val Ala Trp Thr Lys Met Pro Val Cys Glu Glu Ile Phe Glu
                245                 250                 255

Asp Cys Asn Glu Leu Pro Pro Arg Arg Asn Thr Glu Ile Leu Thr Gly
            260                 265                 270

Ser Trp Ser Asp Gln Thr Tyr Pro Glu Gly Thr Gln Ala Ile Tyr Lys
    275                 280                 285

Cys Arg Pro Gly Tyr Arg Ser Leu Gly Asn Val Ile Met Val Cys Arg
290                 295                 300

Lys Gly Glu Trp Val Ala Leu Asn Pro Leu Arg Lys Cys Gln Lys Arg
305                 310                 315                 320

Pro Cys Gly His Pro Gly Asp Thr Pro Phe Gly Thr Phe Thr Leu Thr
                325                 330                 335

Gly Gly Asn Val Phe Glu Tyr Gly Val Lys Ala Val Tyr Thr Cys Asn
            340                 345                 350

Glu Gly Tyr Gln Leu Leu Gly Glu Ile Asn Tyr Arg Glu Cys Asp Thr
        355                 360                 365

Asp Gly Trp Thr Asn Asp Ile Pro Ile Cys Glu Val Val Lys Cys Leu
370                 375                 380

Pro Val Thr Ala Pro Glu Asn Gly Lys Ile Val Ser Ser Ala Met Glu
385                 390                 395                 400

Pro Asp Arg Glu Tyr His Phe Gly Gln Ala Val Arg Phe Val Cys Asn
                405                 410                 415

Ser Gly Tyr Lys Ile Glu Gly Asp Glu Glu Met His Cys Ser Asp Asp
            420                 425                 430

Gly Phe Trp Ser Lys Glu Lys Pro Lys Cys Val Glu Ile Ser Cys Lys
        435                 440                 445

Ser Pro Asp Val Ile Asn Gly Ser Pro Ile Ser Gln Lys Ile Ile Tyr
450                 455                 460

Lys Glu Asn Glu Arg Phe Gln Tyr Lys Cys Asn Met Gly Tyr Glu Tyr
465                 470                 475                 480

Ser Glu Arg Gly Asp Ala Val Cys Thr Glu Ser Gly Trp Arg Pro Leu
                485                 490                 495

Pro Ser Cys Glu Glu Lys Ser Cys Asp Asn Pro Tyr Ile Pro Asn Gly
            500                 505                 510

Asp Tyr Ser Pro Leu Arg Ile Lys His Arg Thr Gly Asp Glu Ile Thr
        515                 520                 525

Tyr Gln Cys Arg Asn Gly Phe Tyr Pro Ala Thr Arg Gly Asn Thr Ala
530                 535                 540

```
Lys Cys Thr Ser Thr Gly Trp Ile Pro Ala Pro Arg Cys Thr Leu Lys
545                 550                 555                 560
```